United States Patent
Alabugin et al.

(10) Patent No.: US 8,927,728 B2
(45) Date of Patent: Jan. 6, 2015

(54) DIPEPTIDE ACETYLENE CONJUGATES AND A METHOD FOR PHOTOCLEAVAGE OF DOUBLE STRAND DNA BY DIPEPTIDE ACETYLENE CONJUGATES

(75) Inventors: Igor Alabugin, Tallahassee, FL (US);
Wang-Yong Yang, Tallahassee, FL (US);
Saumya Roy, Tallahassee, FL (US);
Kemal Kaya, Tallahassee, FL (US);
Qing-Xiang Sang, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 153 days.

(21) Appl. No.: 13/465,529

(22) Filed: May 7, 2012

(65) Prior Publication Data
US 2012/0288940 A1 Nov. 15, 2012

Related U.S. Application Data

(60) Provisional application No. 61/484,359, filed on May 10, 2011.

(51) Int. Cl.
| | | |
|---|---|---|
| C07D 213/16 | (2006.01) | |
| C07D 213/56 | (2006.01) | |
| C07D 213/61 | (2006.01) | |
| C07K 5/062 | (2006.01) | |
| C07K 5/065 | (2006.01) | |
| C07K 5/068 | (2006.01) | |

(52) U.S. Cl.
CPC .......... *C07D 213/61* (2013.01); *C07K 5/06026* (2013.01); *C07K 5/06078* (2013.01); *C07K 5/06086* (2013.01)
USPC .......................................... 546/265; 546/337

(58) Field of Classification Search
CPC ............ C07D 213/61; C07D 5/06026; C07K 5/06086
USPC ................... 435/441; 546/265, 337; 536/25.3
See application file for complete search history.

(56) References Cited

U.S. PATENT DOCUMENTS 7,695,912 B1    4/2010 Alabugin et al.

OTHER PUBLICATIONS

Breiner B, Schlatterer JC, Kovalenko SV, Greenbaum NL, and Alabugin IV. Protected 32P-Labels in Deoxyribonucleotides: Investigation of Sequence Selectivity of DNA Photocleavage by Enediyne—, Fulvene—, and Acetylene—Lysine Conjugates. Angew. Chem. Int. Ed. 2006, 45:3666-3670.*

Yang et al ("C-Lysine Conjugates: pH-Controlled Light-Activated Reagents for Efficient Double-Stranded DNA Cleavage with Implications for Cancer Therapy." J Am Chem Soc. 2009, 131:11458-11470).*

Kovalenko SV and Alabugin IV. Lysine-enediyne conjugates as photochemically triggered DNA doublestrand cleavage agents. 2005, 1444-1446.*

Mahon et al ("Tunable DNA Cleavage by Intercalating Peptidoconjugates." ChemBioChem 2006, 7:766-773).*

(Continued)

*Primary Examiner* — Marcos Sznaidman
*Assistant Examiner* — Rayna B Rodriguez
(74) *Attorney, Agent, or Firm* — Armstrong Teasdale LLP

(57) ABSTRACT

Photoreactive DNA cleaving conjugate compounds are provided comprising a DNA cleaving moiety which comprises an aryl alkyne group and a polyfunctional pH-regulated DNA-binding moiety which comprises at least one or two amino groups.

8 Claims, 17 Drawing Sheets

(56) References Cited

OTHER PUBLICATIONS

Palmer et al ("Molecular Energy Levels of Azines; ab initio Calculations and Correlation with Photoelectron Spectroscopy." J Chem Soc, 1974; 2:778-784).*

Pang et al ("Amplification of DNA-binding affinities of protoberberine alkaloids by appended polyamines." Bioorganic & Medicinal Chemistry Letters, 2007; 17:1018-1021).*

Kim et al ("Induction of Topoisomerase II-Mediated DNA Cleavage by a Protoberberine Alkaloid, Berberrubine." Biochemistry, 1998; 37:16316-16324).*

Yang, Wang-Yong, et al., Engineering pH-Gated Transitions for Selective and Efficient Double-Strand DNA Photocleavage in Hypoxic Tumors, Journal of Medicinal Chemistry, Nov. 3, 2011, pp. 8501-8516, vol. 54, ACS Publications.

Breiner, Boris, et al., Hybrids of Amino Acids and Acetylenic DNA-Photocleavers: Optimising Efficiency and Selectivity for Cancer Phototherapy, Organic & Biomolecular Chemistry, Mar. 7, 2012, pp. 3974-3987, vol. 10, The Royal Society of Chemistry.

Breslin, David T, et al., Anthraquinone Photonucleases: Mechanisms for GG-Selective and Nonselective Cleavage of Double-Stranded DNA, Journal of the American Chemical Society, Mar. 13, 1996, pp. 2311-2319, vol. 118, No. 10, American Chemical Society.

* cited by examiner

DIPEPTIDE ACETYLENE CONJUGATES AND A METHOD FOR PHOTOCLEAVAGE OF DOUBLE STRAND DNA BY DIPEPTIDE ACETYLENE CONJUGATES

CROSS REFERENCE TO RELATED APPLICATIONS

This application claims priority from U.S. Provisional Application Ser. No. 61/484,359, filed on May 10, 2011, the disclosure of which is incorporated herein as if set forth in its entirety.

STATEMENT REGARDING FEDERALLY SPONSORED RESEARCH

This invention was made with government support under Grant No. CHE-0848686 awarded by the National Science Foundation. The government has certain rights in the invention.

FIELD OF THE INVENTION

The present invention generally relates to DNA photocleaving conjugates comprising a DNA-cleaving agent and a polyfunctional pH-regulated DNA-binding part, and a method for controlling the reactivity and selectivity of double strand DNA cleavage by such conjugates.

BACKGROUND OF THE INVENTION

Molecular systems, where structure, reactivity and biological activity are "switchable" via an externally controlled factor, create new opportunities for the design of drug delivery systems, optical sensors, molecular switches/logic gate mimics, and a variety of new materials. See, e.g., Choi, H. S., Huh, K. M., Ooya, T., Yui, N. pH- and Thermosensitive Supramolecular Assembling System: Rapidly Responsive Properties of β-Cyclodextrin-Conjugated Poly(ε-lysine). *J. Am. Chem. Soc.* 125, 6350-6351, (2003); Fabbrizzi, L., Gatti, F., Pallavicini, P., Parodi, L. An 'off-on-off' Fluorescent sensor for pH based on ligand-proton and ligand-metal-proton interactions. *New J. Chem.* 22, 1403-1407, (1998); de Silva, A. P., Gunaratne, H. Q. N., McCoy, C. P. Direct visual indication of pH windows: 'off-on-off' fluorescent PET (photoinduced electron transfer) sensors/switches. *Chem. Commun.*, 2399-2400. (1996); Saha, S., Stoddart, J. F. Photo-driven molecular devices. *Chem. Soc. Rev.* 36, 77-92, (2007);Silvi, S., Arduini, A., Pochini, A., Secchi, A., Tomasulo, M., Raymo, F. M., Baroncini, M., Credi, A. A Simple Molecular Machine Operated by Photoinduced Proton Transfer. *J. Am. Chem. Soc.* 129, 13378-13379, (2007); and Xue, C., Mirkin, C. A. pH-Switchable Silver Nanoprism Growth Pathways. *Angew. Chem. Int. Ed.* 46, 2036-2038, (2007). Out of the many external stimuli, pH-gated "switching" is especially useful for addressing biochemical and environmental processes which depend on the acidity of the medium.

In particular, the relatively acidic extracellular environment of solid tumors lends itself for the design of tumor-specific pH-activated chemical agents. See, e.g., Adams, D. J., Dewhirst, M. W., Flowers, J. L., Gamcsik, M. P., Colvin, O. M., Manikumar, G., Wani, M. C., Wall, M. E. Camptotheis analogues with enhanced antitumor activity in acidic pH. *Cancer Chemother. Pharmacol.* 46, 263-271, (2000); Gabr, A., Kuin, A., Aalders, M., El-Gawly, H., Smets, L. A. Cellular Pharmacokinetics and Cytotoxicity of Camptothecin and Topotecan at Normal and Acidic pH. *Cancer Res.* 57, 4811-4816, (1997); Teicher, B. A., Holden, S. A., Khandakar, V., Herman, T. S. Addition of a topoisomerase I inhibitor to trimodality therapy [cis-diamminedichloroplatinum(II)/heat/radiation] in a murine tumor. *J. Cancer Res. Clinical Oncol.* 119, 645-651, (1993); Wood, P. J., Sansom, J. M., Newell, K., Tannock, I. F., Stratford, I. J. Reduction of tumour intracellular pH and enhancement of melphalan cytotoxicity by the ionophore nigericin. *Int. J. Cancer,* 60, 264-268. (1995); Vukovic, V., Tannock, I. F. Influence of low pH on cytotoxicity of paclitaxel, mitoxantrone and topotecan. *Brit. J. Cancer* 75, 1167-1172, (1997); Wachsberger, P. R., Burd, R., Wahl, M. L., Leeper, D. B. Betulinic acid sensitization of of low pH adapted human melanoma cells to hyperthermia. *Int. J. Hyperthermia* 18, 153-164, (2002); and Hoffner, J., Schottelius, J., Feichtinger, D., Chen, P. Chemistry of the 2,5-didehydropyridine biradical: computational, kinetic, and trapping studies toward drug design. *J. Am. Chem. Soc.* 120, 376-385, (1998). Hyperglycemia and/or such drugs as amiloride, nigericin, and hydralyzine, are able to lower the intracellular pH of cancer cells as well. At dosages that do not affect the normal cells, amiloride and nigericin has been reported to drop the intracellular pH in a number of tumor cell types from 7.2 to 6.2-6.6. See, e.g., Adams, G. E., Stratford, I. J. Bioreductive drugs for cancer therapy: The search for tumor specificity. *Int. J. Radiat. Oncol. Biol. Phys.* 29, 231-238, (1994); Priyadarsini, K. I., Dennis, M. F., Naylor, M. A., Stratford, M. R. L., Wardman, P. Free Radical Intermediates in the Reduction of Quinoxaline N-Oxide Antitumor Drugs: Redox and Prototropic Reactions. *J. Am. Chem. Soc.* 118, 5648-5654, (1996). and references therein; Stubbs, M., Rodrigues, L., Howe, F. A., Wang, J. Jeong, K. S., Veech, R. L., Griffiths, J. R. Cancer Res. Metabolic Consequences of a Reversed pH Gradient in Rat Tumors. 54, 4011-4016, (1994); Lyons, J. C., Ross, B. D. Song, C. W. Enhancement of hyperthermia effect in vivo by amiloride and dids. *Int. J. Radiat. Oncol. Biol. Phys.* 25, 95-103, (1993); Song, C. W., Lyons, J. C., Griffin, R. J., Makepeace, C. M. Thermosensitization by lowering intracellular pH with 5-(N-ethyl-N-isopropyl) amiloride. *Radiother. Oncol.* 27, 252-258, (1993); Song, C. W., Lyons, J. C., Griffin, R. J., Makepeace, C. M., Cragoe, E. J., Jr. Increase in Thermosensitivity of Tumor Cells by Lowering Intracellular pH. *Cancer Res.* 53, 1599-1601, (1993); Song, C. W., Kim, G. E., Lyons, J. C., Makepeace, C. M., Griffin, R. J., Rao, G. H., Cragoe, E. J. Jr. Thermosensitization by increasing intracellular acidity with amiloride and its analogs. *Int. J. Radiat. Oncol. Biol. Phys.* 30, 1161-1169, (1994); Lyons, J. C., Song, C. Killing cf Hypoxic Cells by lowering the Intracellular pH in Combination with Hyperthermia. *Radiat. Res.* 141, 216-218, (1995); and Newell, K., Wood, P., Stratford, I., Tannock, I. Effects of agents which inhibit the regulation of intracellular pH on murine solid tumours. *Br. J. Cancer* 66, 311-317, (1992). When combined with hyperglycemia and/or hypoxia, further acidification to pH as low as 5.5 is possible. See, e.g., Osinsky, S. P., Levitin, I. Y., Bubnovskaya, L. N., Ganusevich, II., Sigan, A. L., Tsykalova, M. V., Zagorujko, L. I. *Exp. Oncol.* 21, 216, (1999); Tannock, I. F., Rotin, D. Acid pH in Tumors and Its Potential for Therapeutic Exploitation. *Cancer Res.* 49, 4373-4384, (1989); Wike-Hooley, J. L., Haveman, J., Reinhold, H. S. The relevance of tumour pH to the treatment of malignant disease. *Radiother Oncol.* 2, 343-366, (1984).

One way to take advantage of these differences involves the development of pH-gated DNA cleaving agents. See Kar, M., Basak, A. *Chem. Rev.* Design, Synthesis, and Biological Activity of Unnatural Enediynes and Related Analogues Equipped with pH-Dependent or Phototriggering Devices. 107, 2861-2890, (2007). The promise of DNA as a target for cancer therapy is illustrated by the astounding biological activity of natural enediyne antibiotics. See Stanulla, M., Wang, J., Cnervinsy, D. S., Thandla, S , Aplan, P. D., DNA cleavage within the MLL breakpoint cluster region is a specific event which occurs as part of higher-order chromatin fragmentation during the initial stages of apoptosis. *Mol. Cell. Biol.*, 17, 4070-4079, (1997). These compounds, hailed as "the most potent family of anticancer agents," can induce double strand DNA cleavage via abstraction of two hydrogen atoms, one from each strand of DNA duplex, with the most efficient double strand DNA-cleaver from this family, calicheamicin, forming ~25-33% of double strand breaks. See Galm, U., Hager, M. H., Van Lanen, S. G., Ju, J., Thorson, J. S., Shen, B. Antitumor Antibiotics: Bleomycin, Enediynes, and Mitomycin. *Chem. Rev.* 105, 739-758, (2005) and Elmroth, K., Nygren, J., Martensson, S., Ismail, I. H., Hammarsten, O. Cleavage of Cellular DNA by Calicheamicin γ1. *DNA Repair* 2, 363-374, (2003). While single strand (ss) DNA damage is easily repaired by enzymatic processes, the repair of double strand (ds) DNA cleavage is more difficult and, thus, it can initiate self-programmed cell death, or apoptosis. See Watson, J. D., Baker, T. A., Bell, S. P., Gann, A., Levine, M., Losick, R. (2004). Molecular Biology of the Gene, ch. 9 and 10. Peason Benjamin Cummings, CSHL Press. 5th ed. Therefore, ds DNA cleavage is a more efficient tool for the cancer therapy as long as it can be induced selectively in cancer cells avoiding damage to healthy cells.

Light-activated DNA-cleavers provide spatial and temporal control over DNA cleavage, allowing drug activation in the right place and at the right time, when concentration of the drug is highest in the cancer tissues. See Armitage, B. Photocleavage of Nucleic Acids. *Chem. Rev.* 98, 1171-1200, (1998). In a previous work, enhanced selectivity was achieved via the development of the first pH-controlled system for ds DNA cleavage. This hybrid system combined an efficient DNA-cleaver capable of operating within the physiological pH range when attached to a pH-sensitive functionality. See Kovalenko, S. V., Alabugin, I. V. Lysine-enediyne conjugates as photochemically triggered DNA double-strand cleavage agents. *Chem. Comm.* 1444-1446, (2005) and Yang, W.-Y., Breiner, B., Kovalenko, S. V., Ben, C., Singh, M., LeGrand, S. N., Sang, Q.-X. A., Strouse, G. F., Copland, J. A., Alabugin, I. V. C-Lysine Conjugates: pH-Controlled Light-Activated Reagents for Efficient Double-Stranded DNA Cleave with Implications for Cancer Therapy. *J. Am. Chem. Soc.* 131, 11458-11470, (2009).

The new family of pH-dependent DNA photocleavers displayed a number of unique properties. In particular, these lysine conjugates showed efficient ds DNA cleavage (ss: ds=2:1) rivaling the efficiency of calicheamicin, selective cleavage at G-sites flanking AT-tracks and ability to convert ss DNA damage into ds DNA damage. See Breiner, B., Schlatterer, J. C., Kovalenko, S. V., Greenvaum, N. L., Alabugin, I. V. Protected $^{32}$P-labels in Deoxyribonucleotides: Investigation of Sequence Selectivity of DNA Photocleavage by Enediyne-, Fulvene-, and Acetylene-lysine Conjugates. *Angew. Chem. Int. Ed.* 45, 3666-3670, (2007) and Breiner, B., Schlatterer, J. C., Kovalenko, S. V., Greenbaum, N. L., Alabugin, I. V. DNA Damage-Site Recognition by Lysine Conjugates. *Proc. Natl. Acad. Sci. U.S.A.,* 104, 13016-13021, (2007). It was also shown that these compounds cleave intracellular DNA, display light-induced cytotoxicity to several cancer cell lines and are susceptible to two-photon absorption (TPA) activation. See Yang, W.-Y., Cao, Q., Callahan, C., Galvis, C., Sang, A. Q.-X., Alabugin, I. V. Intracellular DNA damage by lysine-acetylene conjugates. *J. of Nucleic Acids* Article ID 931394, (2010) and Kauffman, J. F., Turner, J. M., Alabugin, I. V., Breiner, B., Kovalenko, S. V., Badaeva, E. A., Masunov A., Tretiak, S. J. Phys. Chem. A. 110, 241-251, (2006).

SUMMARY OF THE INVENTION

Among the aspects of the present invention may be noted the provision of dipeptide acetylene conjugates and methods for photocleavage of double strand DNA by a dipeptide acetylene conjugates.

Briefly, therefore, the present invention is directed to a photoreactive DNA cleaving conjugate compound having a general structure (I):

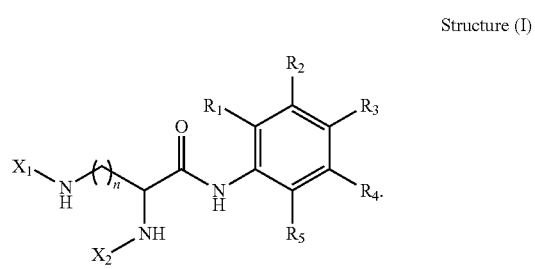

Structure (I)

In the context of Structure (I), at least one of $R_1$, $R_2$, $R_3$, $R_4$, and $R_5$ comprises a DNA cleaving moiety; at least one of $X_1$ and $X_2$ comprises an amino acid bonded via a peptide bond; and n is an integer having a value between one and four.

The present invention is still further directed to a photoreactive DNA cleaving conjugate compound having a general structure (II):

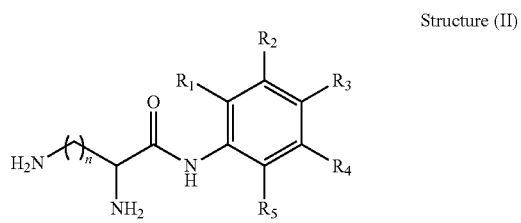

Structure (II)

In the context of Structure (II), at least one of $R_1$, $R_2$, $R_4$, and $R_5$ comprises a DNA cleaving moiety; and n is an integer having a value between one and four.

Other objects and features will be in part apparent and in part pointed out hereinafter.

BRIEF DESCRIPTION OF THE DRAWINGS

FIG. 5A) and (5; FIG. 5B) (3 mM of each) in D$_2$O.

DETAILED DESCRIPTION OF THE EMBODIMENT(S) OF THE INVENTION

The present invention is directed to the design and properties of DNA photocleaving conjugates. In some embodiments, the DNA photocleaving conjugates cleave double stranded DNA. In some embodiments, the DNA photocleaving conjugates are light activated. Advantageously, the light-activated DNA photocleaving conjugates achieve a high ratio of double strand:single strand (ds:ss) cleavage. In some embodiments, the light-activating DNA photocleaving conjugates achieve a ratio of double strand:single strand (ds:ss) cleavage, which exceeds that of calicheamin. Importantly, the ds-DNA cleavage in such systems is suitable for selective targeting of cancer cells because this process is pH-gated. That is, the cleavage efficiency increases dramatically within a relatively narrow and predefined pH range close to the threshold between cancerous and healthy cells.

Figure 1:
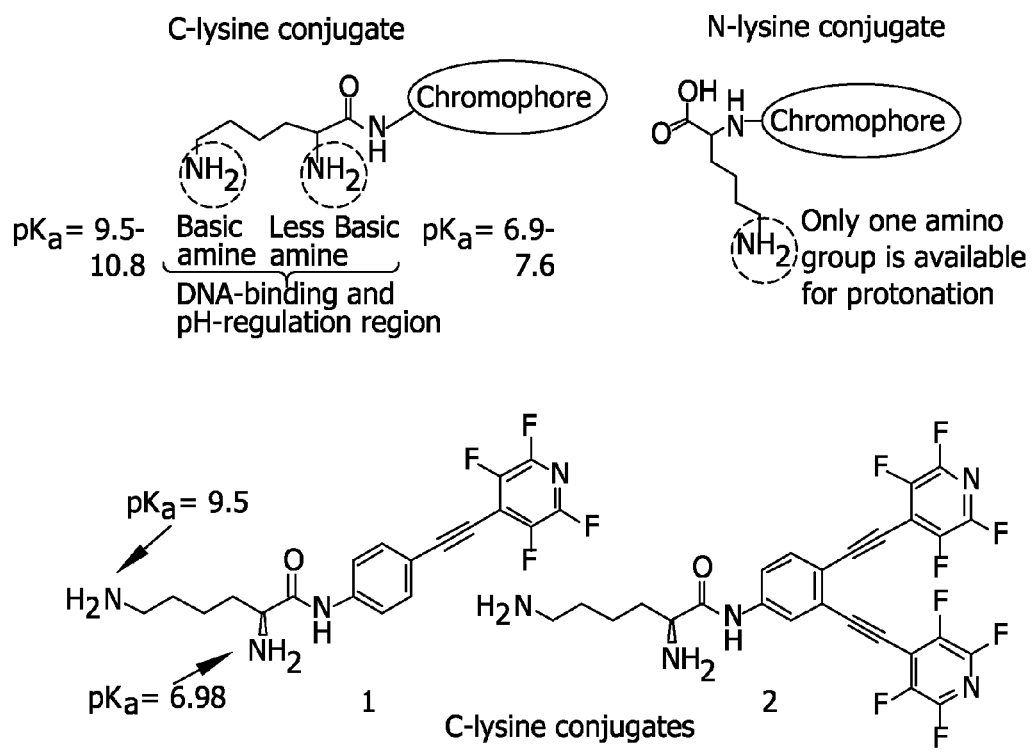
FIG. 1 is a depiction of C-lysine and N-lysine conjugates including first generation C-lysine conjugates (1) and (2).

The practical implementation of this strategy has been based on attachment of the DNA-cleaving moiety to the carboxyl group of lysine. This mode of attachment is different from a more common formation of a classic peptide bond via the α-amino lysine group. See FIG. 1, which depicts C-lysine and N-lysine conjugates including first generation C-lysine conjugates (1) and (2). Attachment of the DNA-cleaving moiety to the carboxyl group of lysine has been reported. See, e.g., U.S. Pat. No. 7,695,912, the entire disclosure of which is hereby incorporated as if set forth in its entirety. See also Saito, I., Takayama, M., Sugiyama, H., Nakatani, H. Photoinduced DNA Cleavage via Electron Transfer: Demonstration That Guanine Residues Located 5' to Guanine Are the Most Electron-Donating Sites. *J. Am. Chem. Soc.* 117, 6406-6407, (1995); Saito, I., Takayama, M., Kawanishi, S. Photoactivatable DNA-Cleaving Amino Acids: Highly Sequence-Selective DNA Photocleavage by Novel L-Lysine Derivatives. *J. Am. Chem. Soc.* 117, 5590-5591, (1995); Plourde, G., II, El-Shafey, A., Fouad, F. S., Purohit, A. S., Jones, G. B. Protein degradation with photoactivated enediyne-amino acid conjugates. *Bioorg. Med. Chem. Lett.* 12, 2985-2988, (2002); Kumar, A., Rao, M. V., Menon, S. K. Photoinduced DNA cleavage by fullerene-lysine conjugate. *Tetrahedron Lett.* 50, 6526-6530, (2009). Importantly, this choice leaves both amino groups of the lysine residue free.

The pH-gated behaviour in this design was based on the different properties of these two amino groups. The auxiliary amino group is protonated at a wider range of physiological conditions. This group enhances solubility of conjugates in water, increases their affinity to the negatively charged backbone of DNA, and modulates the basicity of the less basic ($pK_a$~7) α-amino group. This "pH-gating" amino group undergoes protonation only under a smaller subset of conditions which enables the pH-gated switch in DNA binding and photophysical properties of the conjugate at the desired pH threshold. At this threshold, the DNA-cleaver was transformed from a monocation to a dication, a change which leads to a dramatic increase in the DNA-cleaving ability. See FIG. 1 herein. See also U.S. Pat. No. 7,695,912.

Figure 2:
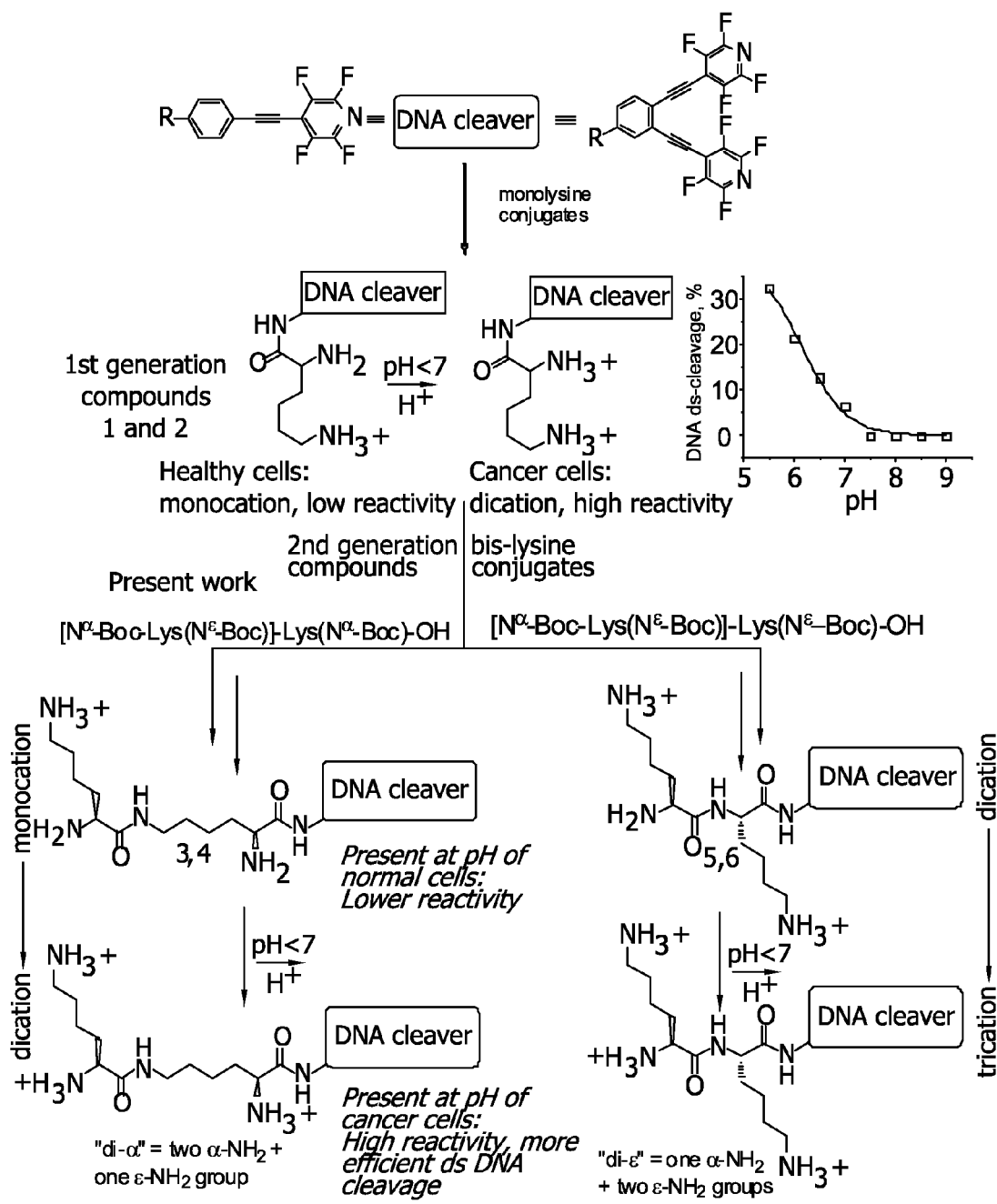
FIG. 2 is a depiction of the design and structural variations for bis-lysine conjugates (3), (4), (5), and (6) of the present invention having three protonatable amino groups.
Figure 3:
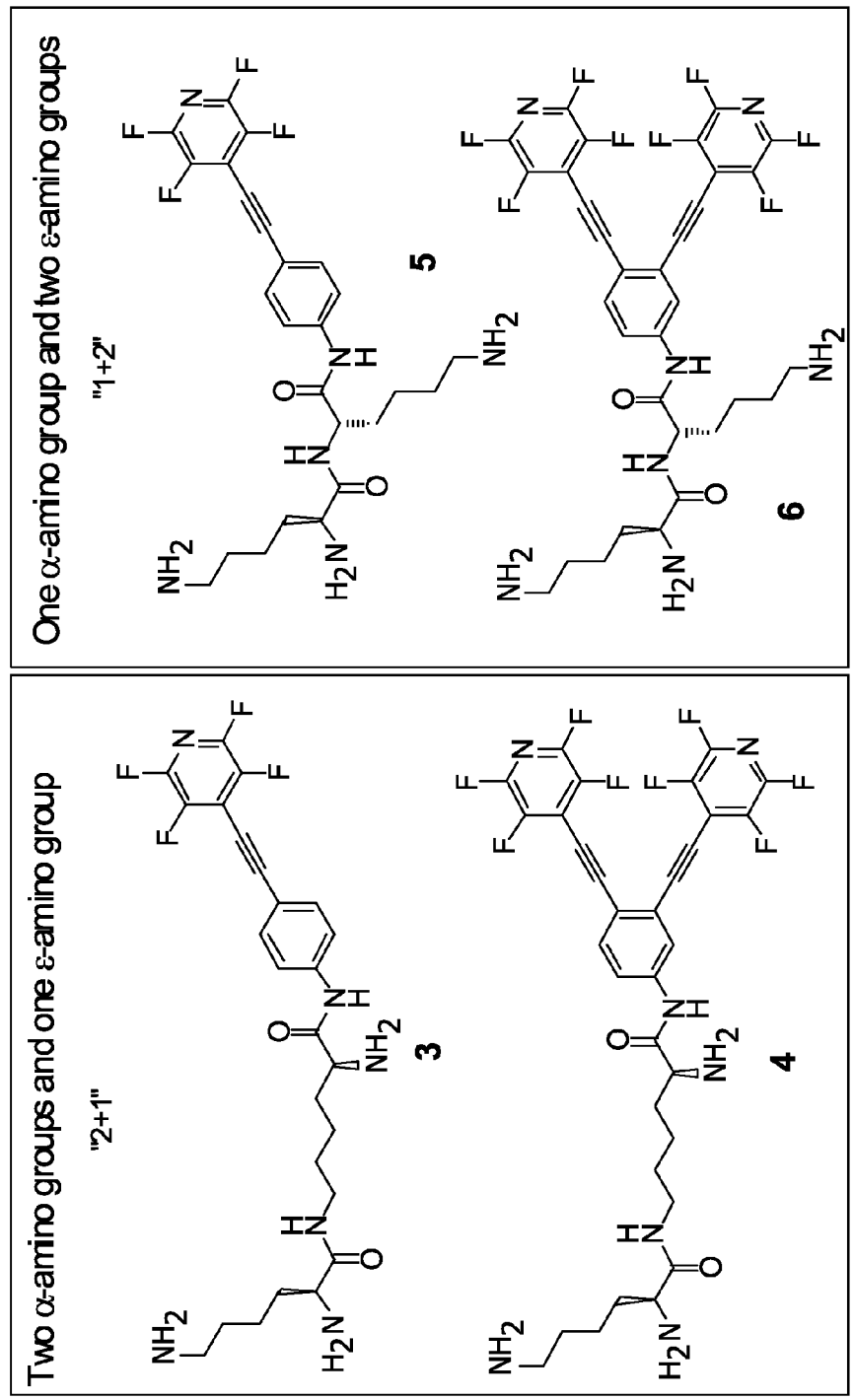
FIG. 3 is a depiction of the structures of bis-lysine conjugates containing two α-amino groups and one ε-amino group (3) and (4) and bis-lysine conjugates containing one α-amino group and two ε-amino group (5) and (6).

In order to increase the selectivity, the difference in reactivity of the two forms should be as large as possible. It has currently been discovered that the transformation from a monocation to a trication increases the contrast in reactivity even further. FIG. 2 depicts the the design and structural variations for bis-lysine conjugates (3), (4), (5), and (6) of the present invention having three protonatable amino groups. In order to test the possibility of designing systems activated via conversion into a multiprotonated state, two types of bis-lysine peptides were designed: one connected through a usual peptide bond via the α-amino group (5, 6 in FIG. 3) and the other is connected via the ε-amino group (3, 4 in FIG. 3). FIG. 3 thus depicts structures of bis-lysine conjugates (3) and (4) containing two α-amino groups and one ε-amino group and bis-lysine conjugates (5) and (6) containing one α-amino group and two ε-amino groups.

This design enabled the conjugates to retain the same total number of amino groups in the conjugate, but with varied nature and relative basicity (two α-/one ε-group in (3) and (4), two ε-/one α-group in (5) and (6)). See FIG. 3. In each of the case, the final protonation state corresponds to a tricationic dipeptide moiety expected to display the strongest binding to DNA. However, the initial protonation state is expected to be different: monocationic for conjugates (3) and (4) but dicationic for conjugates (5) and (6). Since the α-amino groups are responsible for the observed pH-dependence in the mono lysine conjugates, it was expected that the above structural variations will have a large impact on the pH-dependence of DNA cleavage by the new bis-lysine conjugates.

The structural variation possible in the preparation of a photoreactive DNA cleaving conjugate for the cleaving of double stranded DNA of the present invention is thus based on the various binding possibilities of the two functional components that comprise the photoreactive DNA cleaving conjugate. A first component of the compound is a DNA cleaving moiety. In some embodiments, the DNA cleaving moiety comprises an aryl alkyne group. A second component of the compound is a polyfunctional pH-regulated DNA-binding moiety. In some embodiments, the polyfunctional pH-regulated DNA-binding moiety comprises an amino acid. In some embodiments, the polyfunctional pH-regulated DNA-binding moiety comprises at least two amino groups. In some embodiments, the polyfunctional pH-regulated DNA-binding moiety comprises a lysine amino acid. In some embodiments, the polyfunctional pH-regulated DNA-binding moiety comprises two lysine amino acids bonded via a peptide linkage. In some embodiments, the polyfunctional pH-regulated DNA-binding moiety comprises a lysine amino acid covalently bonded via a peptide linkage to a second amino acid. In some embodiments, the DNA cleaving moiety and the polyfunctional pH-regulated DNA-binding moiety are linked via an aryl ring, e.g., a benzene ring.

Orientation and modification of the pH-regulated DNA-binding moiety (e.g., an amino acid or dipeptide) with respect to the DNA-cleaving moiety (aryl alkyne) around the benzene ring enables further control of the reactivity and selectivity of the compound of the present invention for double stranded DNA cleavage. That is, in some embodiments, different photoreaction of DNA cleavers with the varying positions (ortho-, meta- and para-) of aryl alkynes with respect to the lysine-based binding moiety results in DNA damage via different mechanisms. In some embodiments, the DNA cleavers are located ortho- and meta- on the aryl rings with respect to the lysine-based binding moiety. In the DNA-binding part, the remote (δ-, ε-, γ-, and β-) amino groups enhance solubility and affinity to DNA whereas the α-amino groups undergo protonation at the desired pH range, accounting for an increase in reactivity in the region suitable for targeting the hypoxic tissue. Inclusion of another α-amino group or ε-amino group in a dipeptide moiety dramatically increases the reactivity and selectivity for the double stranded DNA cleavage in comparison to the monolysine conjugate. Importantly, this increase in reactivity is observed at the slightly acidic pH values.

In some embodiments, a photoreactive DNA cleaving conjugate compound for the cleaving of double stranded DNA of the present invention has the general structure (I):

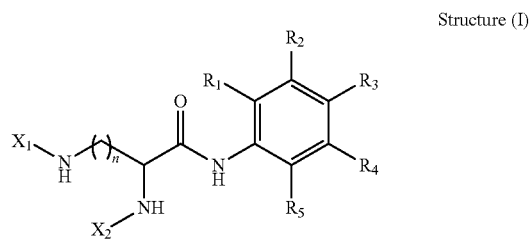

Structure (I)

In above structure (I), at least one of $R_1$, $R_2$, $R_3$, $R_4$, and $R_5$ comprises a DNA cleaving moiety. In some embodiments, multiple, i.e., at least two, three, four or even all five, groups among $R_1$, $R_2$, $R_3$, $R_4$, and $R_5$ comprise the DNA cleaving moiety. In some preferred embodiments, the DNA cleaving moiety is preferably located at either or both the $R_1$ and $R_5$ locations (i.e., ortho with respect to the polyfunctional pH-regulated DNA-binding moiety). In some preferred embodiments, the DNA cleaving moiety is preferably located at the $R_3$ location and either or both the $R_1$ and $R_5$ locations (i.e., ortho with respect to the polyfunctional pH-regulated DNA-binding moiety). In some preferred embodiments, the DNA cleaving moiety is preferably located at either or both the $R_2$ and $R_4$ locations (i.e., meta with respect to the polyfunctional pH-regulated DNA-binding moiety). In some preferred embodiments, the DNA cleaving moiety is preferably located at the $R_3$ location and either or both the $R_2$ and $R_4$ locations (i.e., meta with respect to the polyfunctional pH-regulated DNA-binding moiety).

In some embodiments, the DNA cleaving moiety located at one or more of the $R_1$, $R_2$, $R_3$, $R_4$, and $R_5$ may comprise an alkynyl terminated with an aryl moiety, such that the $R_1$, $R_2$, $R_3$, $R_4$, and $R_5$ may comprise a moiety having the following structure:

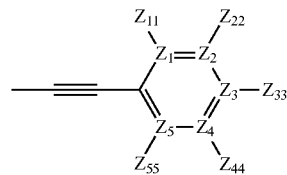

wherein $Z_1$, $Z_2$, $Z_3$, $Z_4$, and $Z_5$ are selected from the group consisting of carbon, nitrogen, oxygen, Or sulfur; and $Z_{11}$, $Z_{22}$, $Z_{33}$, $Z_{44}$, and $Z_{55}$ are selected from the group consisting of hydrogen, alkyl (such as hydrocarbyl having from one to about 12 carbon atoms, preferably from one to about 6 carbon atoms), alkenyl, aryl (having from 6 to 18 carbon atoms, such as phenyl, naphthyl, anthracenyl, phenanthrenyl, etc.), heteroaryl (e.g., pyridinyl, pyrazinyl, pyrimidinyl, pyridazinyl, etc.), chloride, fluoride, bromide, ester (which may be substituted with alkyl having from one to about 6 carbon atoms), and cyano (—CN). In general, $Z_1$, $Z_2$, $Z_3$, $Z_4$, and $Z_5$ are each carbon or one of $Z_1$, $Z_2$, $Z_3$, $Z_4$, and $Z_5$ may be a heteroatom, such as nitrogen, sulfur, or oxygen, and the remainder are carbon.

In some embodiments, one or more of the $R_1$, $R_2$, $R_3$, $R_4$, and $R_5$ may comprise any DNA cleaving moiety having the following structures:

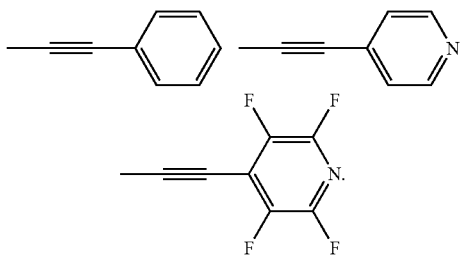

Any remaining $R_1$, $R_2$, $R_3$, $R_4$, and $R_5$ may comprise hydrogen, alkyl (such as hydrocarbyl having from one to about 12 carbon atoms, preferably from one to about 6 carbon atoms, e.g., methyl, ethyl, n-propyl, iso-propyl, n-butyl, iso-butyl, n-butyl, pentyls, hexyls, etc.), alkenyl, aryl (having from 5 to 18 carbon atoms, such as phenyl, naphthyl, etc. and heteroaromatic groups such as pyridine, furan, pyrazine, imidazole, pyrazole, thiophene, etc.) chloride, fluoride, bromide, ester (which may be substituted with alkyl having from one to about 6 carbon atoms), and cyano (—CN).

The value of n in the above structure (I) is an integer having a value between one and four. In some preferred embodiments, the value of n is one. In some preferred embodiments, the value of n is four.

In above structure (I), $X_1$ and $X_2$ are each independently selected from among hydrogen or an amino acid. In general, the $X_1$ and/or $X_2$ moieties may comprise any of the known amino acids. Although amino acids may be more readily available in the natural L-configuration, the amino acids used in the synthesis of the conjugates of the present invention may have the L-configuration, the D-configuration, or a racemic mixture of both L- and D-configurations. Preferred amino acids include lysine, glycine, alanine, valine, isoleucine, leucine, tyrosine, phenylalanine, arginine, and histidine. Glycine, alanine, lysine, phenylalanine, and tyrosine are particularly preferred. In preferred embodiments, at least one of $X_1$ and $X_2$ comprises an amino acid.

In some embodiments, either or both of $X_1$ and $X_2$ may have the following structure:

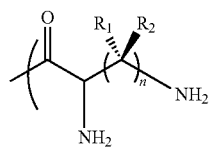

wherein each n is an integer having a value between one and four. The $R_1$ and $R_2$ within this structure may be hydrogen or short chain alkyl, such as hydrocarbyls having one through four carbon atoms, or an amino group. In the above structure, the open parenthesis represents the bond by which the moiety is covalently bonded to the nitrogen atom of Structure (I).

In some embodiments, either or both of $X_1$ and $X_2$ may have the following structure:

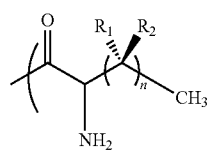

wherein each n is an integer having a value between 0 and four. The $R_1$ and $R_2$ within this structure may be hydrogen or short chain alkyl, such as hydrocarbyls having one through four carbon atoms, or an amino group. Preferably, the $R_1$ and $R_2$ are hydrogen or methyl. In the above structure, the open parenthesis represents the bond by which the moiety is covalently bonded to the nitrogen atom of Structure (I).

In some embodiments, either or both of $X_1$ and $X_2$ may have the following structure:

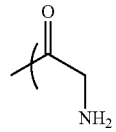

In the above structure, the open parenthesis represents the bond by which the moiety is covalently bonded to the nitrogen atom of Structure (I).

In some embodiments, a photoreactive DNA cleaving conjugate compound for the cleaving of double stranded DNA of the present invention has the general structure (II):

Structure (II)

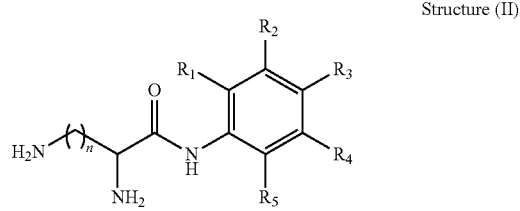

wherein at least one of $R_1$, $R_2$, $R_4$, or $R_5$ comprises a DNA cleaving moiety. In some embodiments, $R_3$ may also comprise a DNA cleaving moiety.

In some embodiments, the DNA cleaving moiety located at one or more of the $R_1$, $R_2$, $R_4$, and $R_5$ may comprise an alkynyl terminated with an aryl moiety, such that the $R_1$, $R_2$, $R_3$, $R_4$, and $R_5$ may comprise a moiety having the following structure:

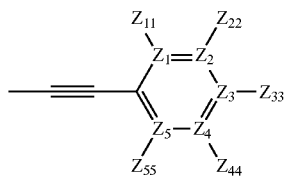

wherein $Z_1$, $Z_2$, $Z_3$, $Z_4$, and $Z_5$ are selected from the group consisting of carbon, nitrogen, oxygen, or sulfur; and $Z_{11}$, $Z_{22}$, $Z_{33}$, $Z_{44}$, and $Z_{55}$ are selected from the group consisting of hydrogen, alkyl (such as hydrocarbyl having from one to about 12 carbon atoms, preferably from one to about 6 carbon atoms), alkenyl, aryl (having from 6 to 18 carbon atoms, such as phenyl, naphthyl, anthracenyl, phenanthrenyl, etc.), heteroaryl (e.g., pyridinyl, pyrazinyl, pyrimidinyl, pyridazinyl, etc.), chloride, fluoride, bromide, ester (which may be substituted with alkyl having from one to about 6 carbon atoms), and cyano (—CN). In general, $Z_1$, $Z_2$, $Z_3$, $Z_4$, and $Z_5$ are each carbon or one of $Z_1$, $Z_2$, $Z_3$, $Z_4$, and $Z_5$ may be a heteroatom, such as nitrogen, sulfur, or oxygen, and the remainder are carbon.

In some embodiments, one or more of the $R_1$, $R_2$, $R_4$, and $R_5$ may comprise any DNA cleaving moiety having the following structures:

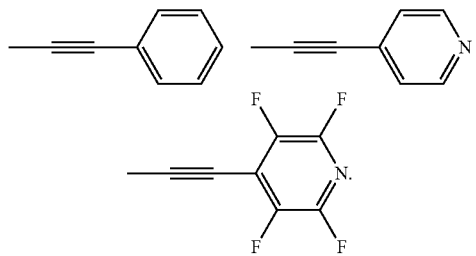

The remainder of n, $R_1$, $R_2$, $R_3$, $R_4$, and $R_5$ are as defined in connection with Structure (I).

In some preferred embodiments of Structure (II), at least two of $R_1$, $R_2$, $R_4$, or $R_5$ comprises a DNA cleaving moiety having the following structures:

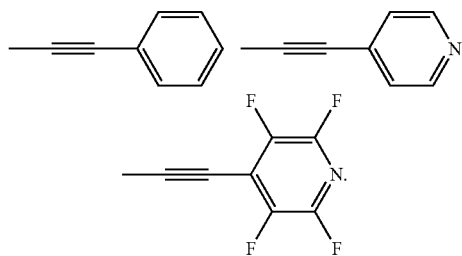

The remainder of n, $R_1$, $R_2$, $R_3$, $R_4$, and $R_5$ are as defined in connection with Structure (I).

In some embodiments of Structure (II), at least one of $R_1$ or $R_5$ is

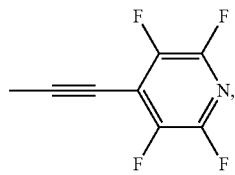

and each n has a value of four. The remainder of n, $R_1$, $R_2$, $R_3$, $R_4$, and $R_5$ are as defined in connection with Structure (I).

In some embodiments of Structure (II), at least one of $R_2$ or $R_4$ is

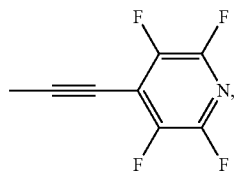

and each n has a value of four. The remainder of n, $R_1$, $R_2$, $R_3$, $R_4$, and $R_5$ are as defined in connection with Structure (I).

In some embodiments, a photoreactive DNA cleaving conjugate compound for the cleaving of double stranded DNA of the present invention has the general structure (I) or (II), wherein $R_2$, $R_3$, and $R_4$, are hydrogen, one of $R_1$ and $R_5$ is

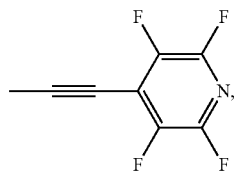

the other of $R_1$ and $R_5$ is hydrogen. An exemplary compound may have the general structure (III):

Structure (III)

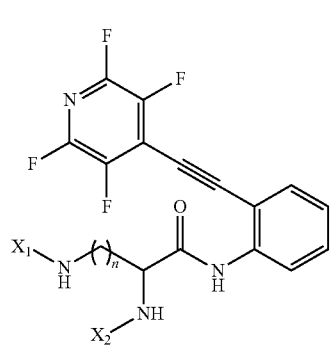

wherein $X_1$, $X_2$, and n are as defined above in connection with Structure (I). In some preferred embodiments of Structure (III), each n has a value of four.

In some embodiments of the compound of structure (III), $X_1$ and $X_2$ are both hydrogen, and the compound has the general structure (IV):

Structure (IV)

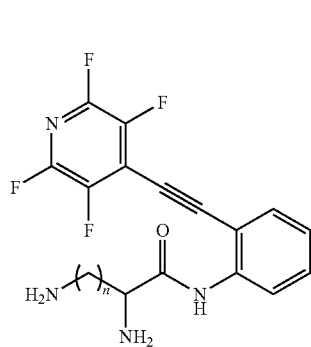

In some preferred embodiments of the compound of structure (IV), $X_1$ and $X_2$ are both hydrogen, n is four, and the compound has the general structure (IVa):

Structure (IVa)

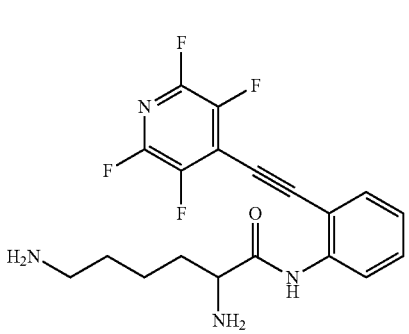

In some embodiments, a photoreactive DNA cleaving conjugate compound for the cleaving of double stranded DNA of the present invention has the general structure (I) or (II), wherein $R_1$, $R_3$, and $R_5$, are hydrogen, one of $R_2$ and $R_4$ is

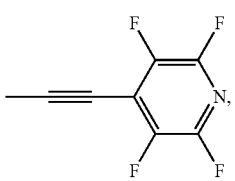

the other of $R_2$ and $R_4$ is hydrogen. An exemplary compound may have the general structure (V):

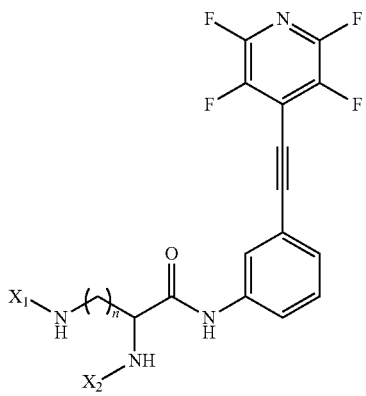

Structure (V)

wherein $X_1$, $X_2$, and n are as defined above in connection with Structure (I). In some preferred embodiments of Structure (V), each n has a value of four.

In some embodiments of the compound of structure (V), $X_1$ and $X_2$ are both hydrogen, and the compound has the general structure (VI):

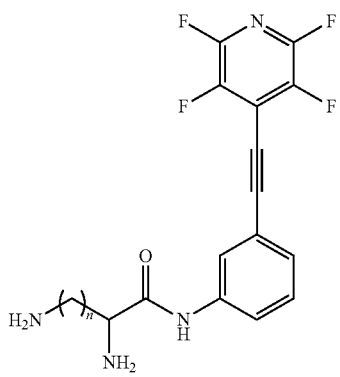

Structure (VI)

In some preferred embodiments of the compound of structure (VI), $X_1$ and $X_2$ are both hydrogen, n is four, and the compound has the general structure (VIa):

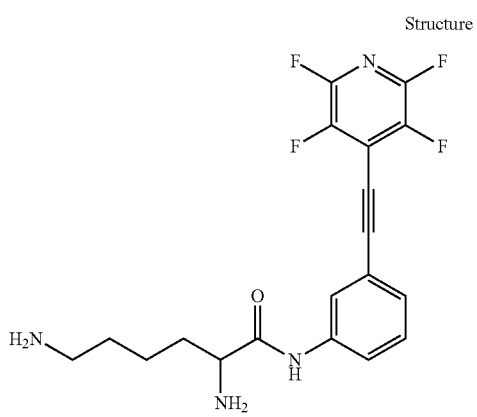

Structure (VIa)

In some embodiments, a photoreactive DNA cleaving conjugate compound for the cleaving of double stranded DNA of the present invention has the general structure (I) or (II), wherein one of $R_1$ and $R_5$ is

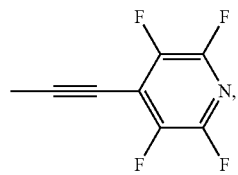

the other of $R_1$ and $R_5$ is hydrogen, one of $R_2$ and $R_4$ is

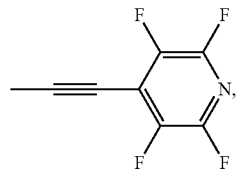

the other of $R_2$ and $R_4$ is hydrogen, and the compound has the general structure (VII):

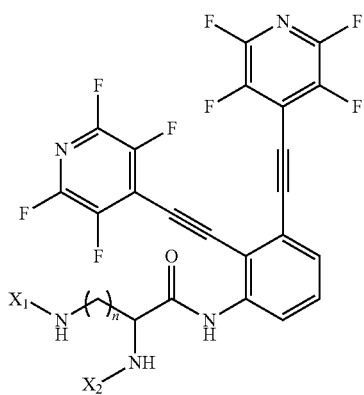

Structure (VII)

wherein $X_1$, $X_2$, and n are as defined above in connection with Structure (I).

In some preferred embodiments of structure (VII), $X_1$ and $X_2$ are both hydrogen, n is four, and the compound has the general structure (VIIa):

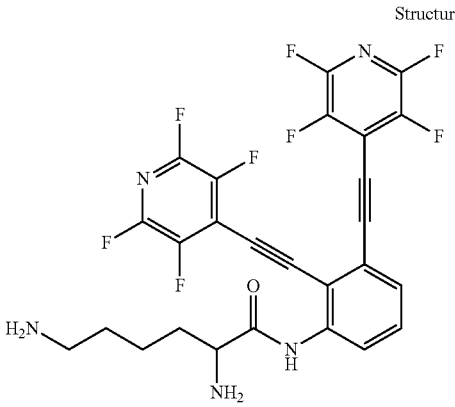

Structure (VIIa)

In some embodiments, a photoreactive DNA cleaving conjugate compound for the cleaving of double stranded DNA of the present invention has the general structure (I) or (II), wherein both $R_2$ and $R_4$ are

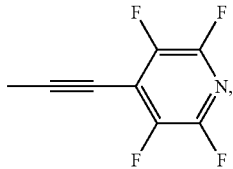

and the compound has the general structure (VIII):

Structure (VIII)

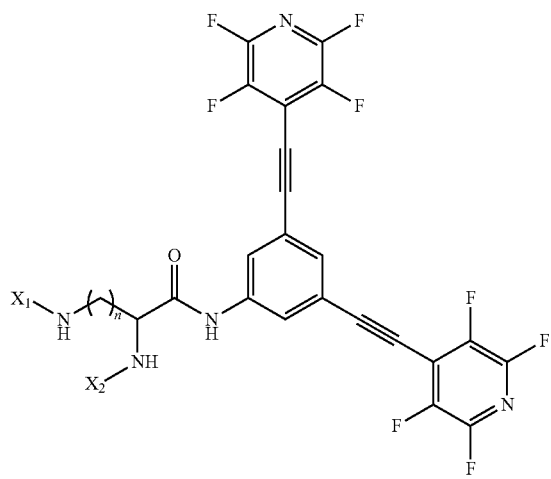

wherein $X_1$, $X_2$, and n are as defined above in connection with Structure (I).

In some preferred embodiments of structure (VIII), $X_1$ and $X_2$ are both hydrogen, n is four, and the compound has the general structure (VIIIa):

Structure (VIIIa)

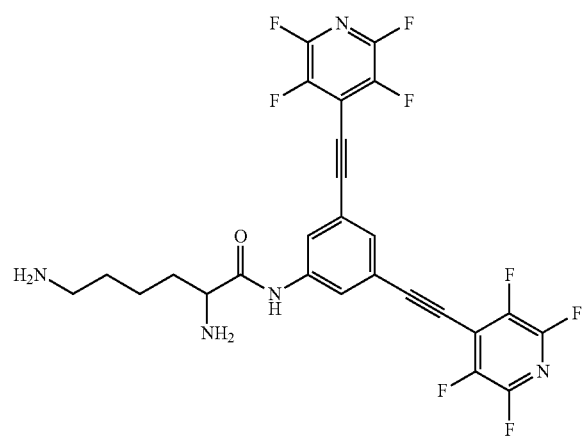

In some embodiments, a photoreactive DNA cleaving conjugate compound for the cleaving of double stranded DNA of the present invention has the general structure (I), wherein $R_3$ is a DNA cleaving moiety, and the compound has the following general structure (IX):

Structure (IX)

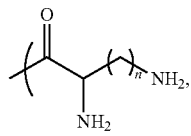

In the above Structure (IX), $R_1$, $R_2$, $R_4$, and $R_5$ are as defined above in connection with Structure (I), and at least one of $X_1$ and $X_2$ is an amino acid. In some preferred embodiments, at least one of $X_1$ and $X_2$ is

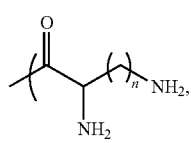

and each n is independently an integer between one and four.

In some embodiments of the compound of structure (IX), $X_1$ is

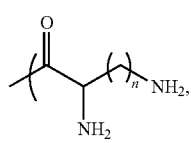

$X_2$ is hydrogen, and the compound has the general structure (X):

Structure (X)

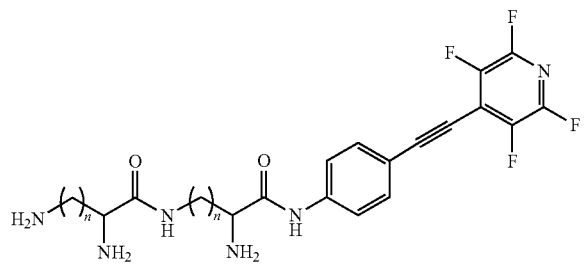

wherein each n is independently an integer between one and four.

In some preferred embodiments of the compound of structure (X), each n is four, and the compound has the following structure (Xa):

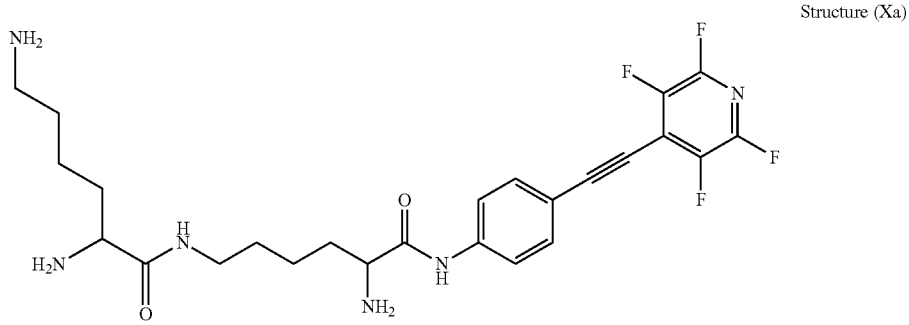

Structure (Xa)

In some embodiments of the compound of structure (IX), $X_1$ is hydrogen, $X_2$ is

and the compound has the general structure (XI):

Structure (XI)

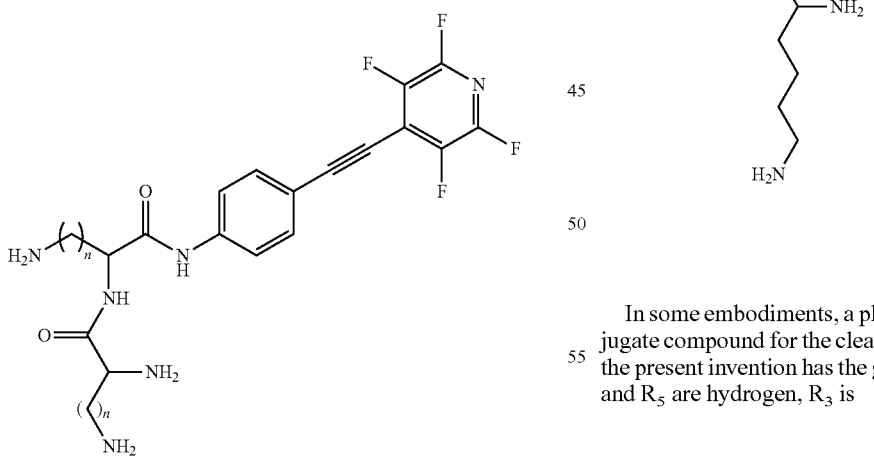

wherein each n is independently an integer between one and four.

In some preferred embodiments of the compound of structure (XI), each n is four, and the compound has the following structure (XIa):

Structure (XIa)

In some embodiments, a photoreactive DNA cleaving conjugate compound for the cleaving of double stranded DNA of the present invention has the general structure (I), wherein $R_1$ and $R_5$ are hydrogen, $R_3$ is one of $R_2$ or $R_4$ is

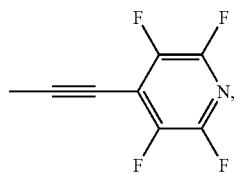

and the other of $R_2$ or $R_4$ is hydrogen. Such a compound has the general structure (XII):

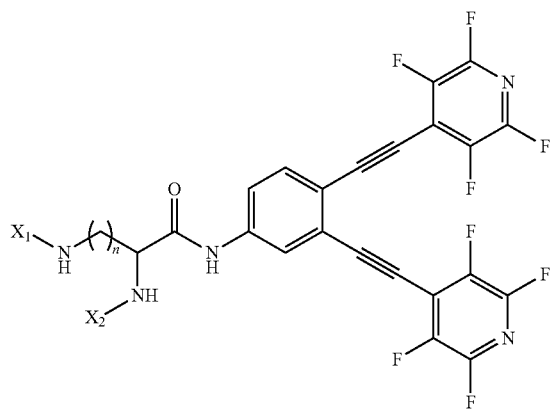

Structure (XII)

In the above Structure (XII), n is as defined above in connection with Structure (I) and at least one of $X_1$ and $X_2$ is an amino acid. In some preferred embodiments, at least one of $X_1$ and $X_2$ is

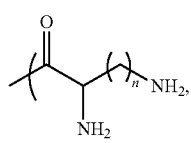

and each n is independently an integer between one and four.

In some embodiments of the compound of structure (XII), $X_1$ is

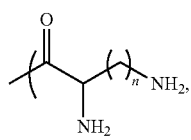

$X_2$ is hydrogen, and the compound has the general structure (XIII):

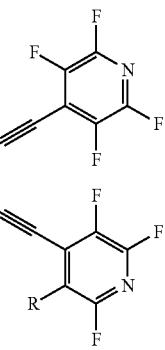

Structure (XIII)

wherein each n is independently an integer between one and four.

In some preferred embodiments of the compound of structure (XIII), each n is four, and the compound has the following structure (XIIIa):

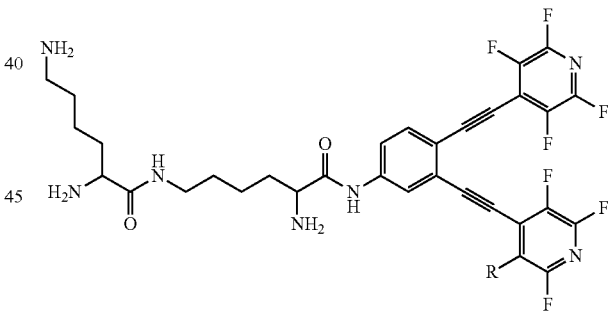

Structure (XIIIa)

In some embodiments of the compound of structure (XII), $X_1$ is hydrogen, $X_2$ is

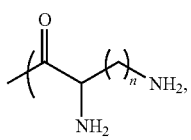

and the compound has the general structure (XIV):

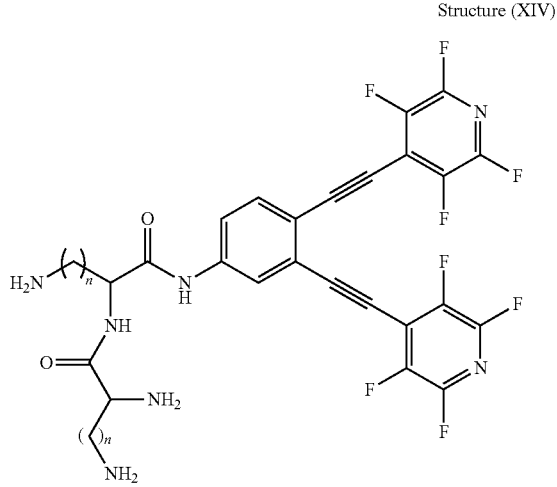

wherein each n is independently an integer between one and four.

In some preferred embodiments of the compound of structure (XIV), each n is four, and the compound has the following structure (XIVa):

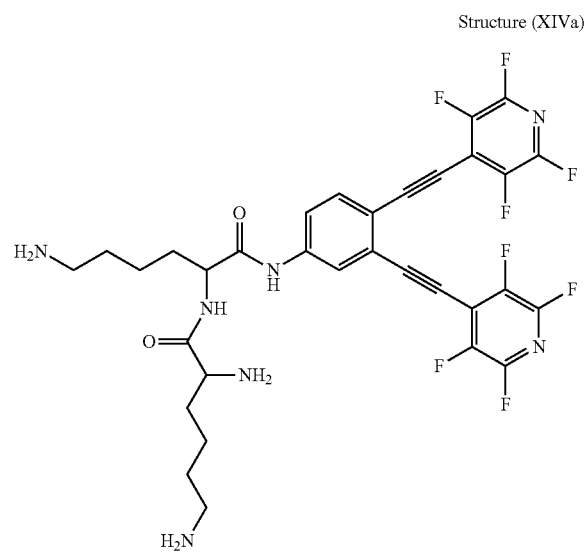 [SMILES: NCCCCC(N)C(=O)NC(CCCCN)C(=O)Nc1ccc(C#Cc2c(F)c(F)nc(F)c2F)c(C#Cc2c(F)c(F)nc(F)c2F)c1]

In some embodiments, a photoreactive DNA cleaving conjugate compound for the cleaving of double stranded DNA of the present invention has the general structure (IX):

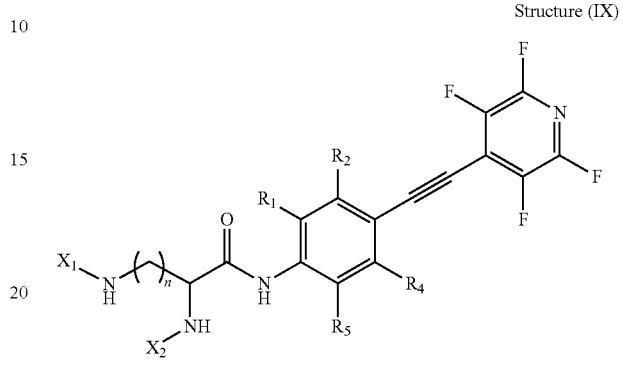

wherein $X_1$ is an alanine moiety having the structure

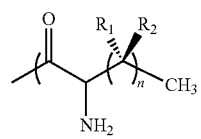

and $X_2$ is hydrogen. An exemplary photoreactive DNA cleaving conjugate compound having an alanine moiety has structure (XV):

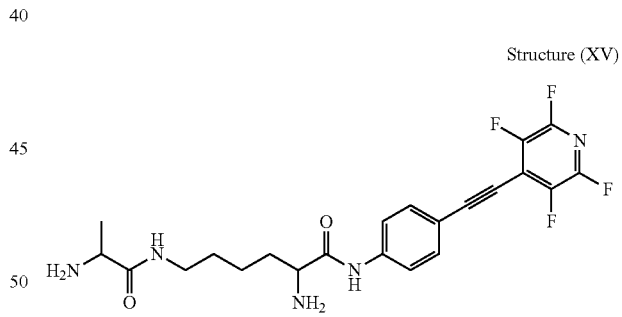

In some embodiments, the photoreactive DNA cleaving conjugate compound of the general structure (IX) has an $X_2$ of

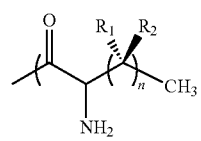

and an $X_1$ of hydrogen. An exemplary photoreactive DNA cleaving conjugate compound having an alanine moiety has structure (XVI):

Structure (XVI)

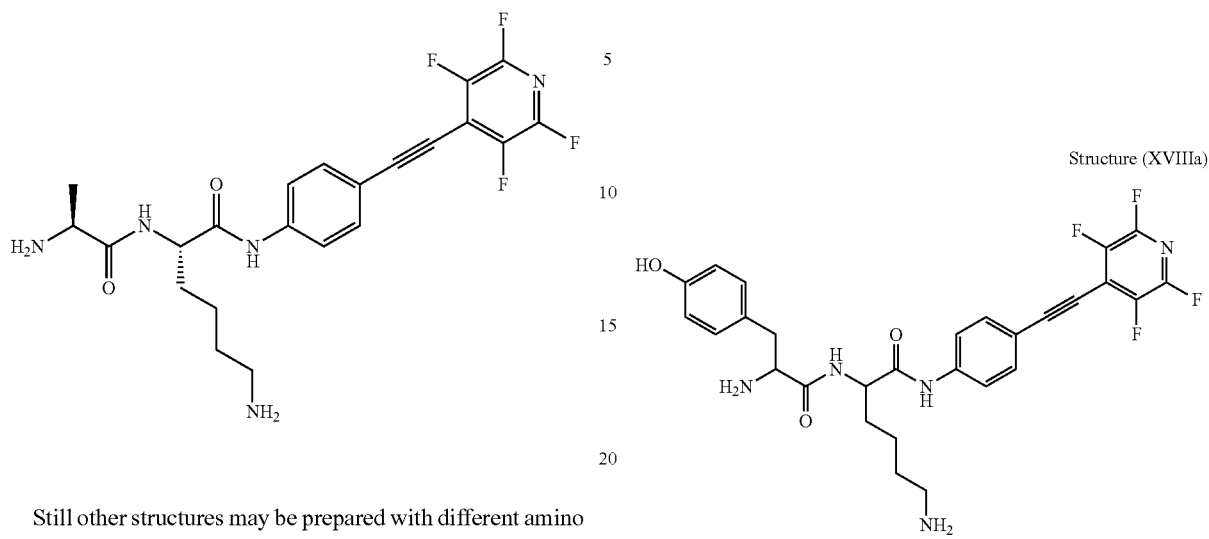

Still other structures may be prepared with different amino acids bonded to the $X_1$ and $X_2$ groups, such as phenylalanine, as in below structures (XVIIa) and (XVIIb):

Structure (XVIIa)

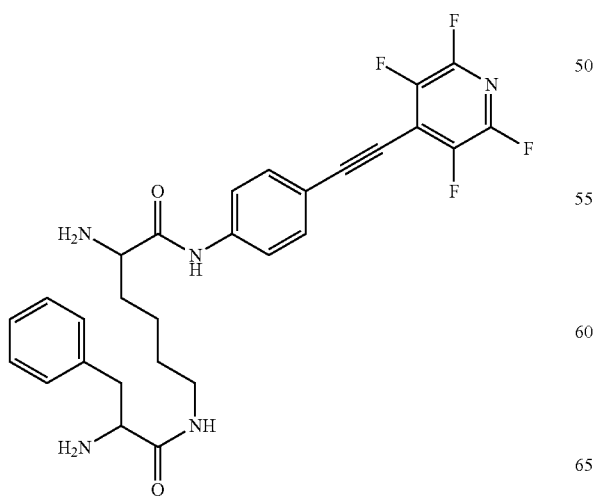

Structure (XVIIb)

Additional structures (XVIIIa) and (XVIIIb) were prepared with tyrosine bonded to the $X_1$ and $X_2$ groups:

Structure (XVIIIa)

Structure (XVIIIb)

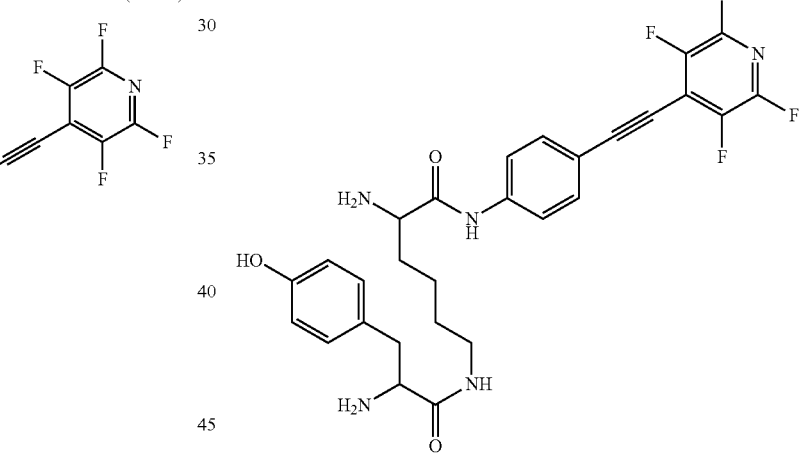

Synthesis of Conjugates.

To synthesize the target peptide conjugates, Boc-protected lysine dipeptides ((9) and (10) in the following Scheme 1) were coupled with anilines (7) and (8) using dicyclohexylcarbodiimide (DCC) and 4-dimethylaminopyridine (DMAP) as coupling reagents. See the following Scheme 1. Removal of Boc-groups with trifluoroacetic acid (TFA) in $CH_2Cl_2$ produces target compounds (3)-(6). See also FIGS. 2 and 3. The final products were fully characterized by spectroscopic methods and used in the DNA-photocleavage studies as TFA salts.

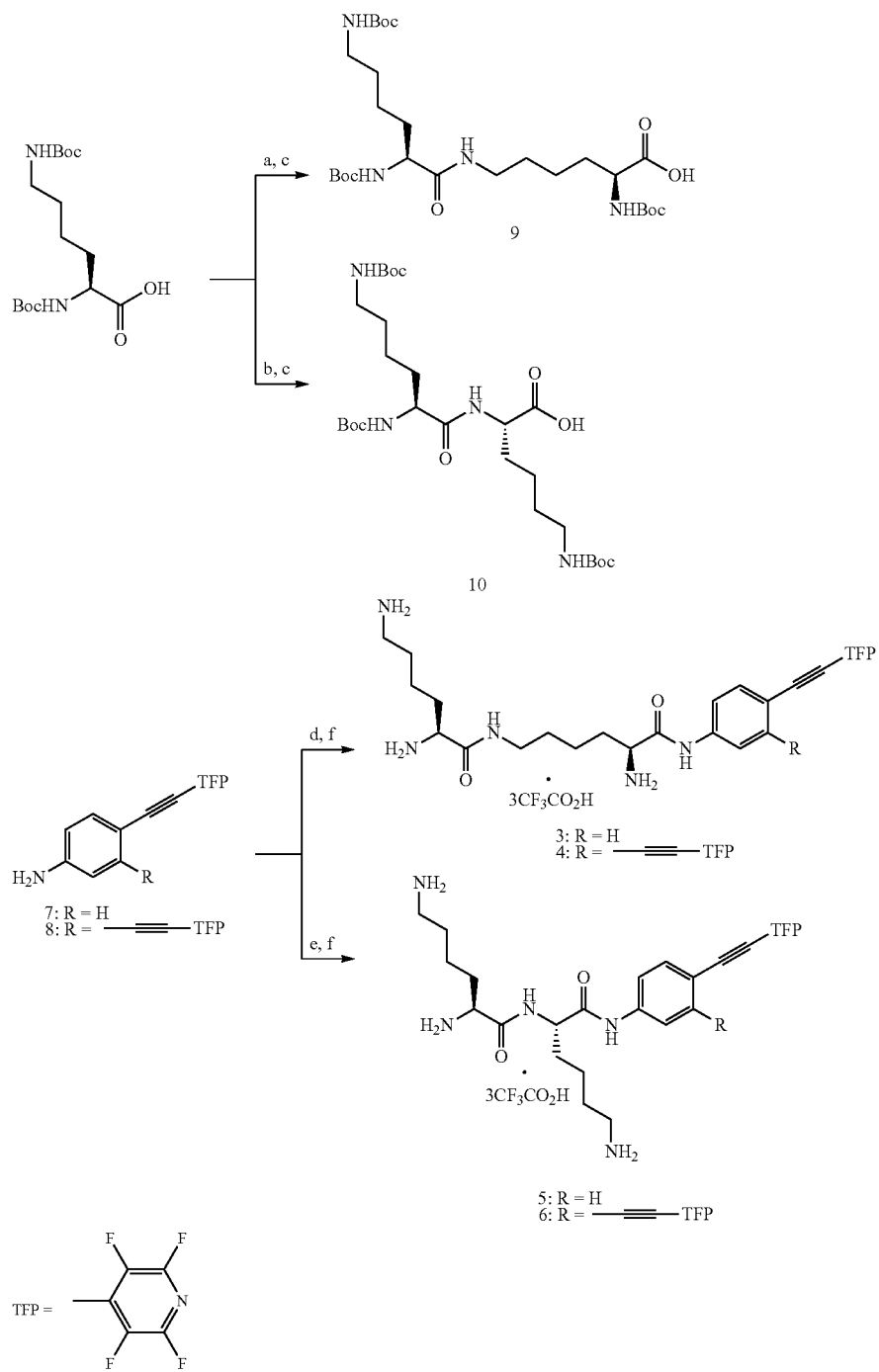

Scheme 1. Synthesis of bis-lysine conjugates.

a. Lys(N$^a$—Boc)—OMe, EDCI, HOBT, DIPEA, CH$_2$Cl$_2$, 85%;
b. Lys(N$^e$—Boc)—OMe, EDCI, HOBT, DIPEA, CH$_2$Cl$_2$, 80%;
c. LiOH, THF:MeOH; H$_2$O;
d. [N$^a$—Boc-Lys(N$^e$—Boc)]-Lys(N$^a$—Boc)—OH (9), DCC, DMAP, CH$_2$Cl$_2$, rt, 2 d;
e. [N$^a$—Boc-Lys(N$^e$—Boc)]-Lys(N$^e$—Boc)—OH (10), DCC, DMAP, CH$_2$Cl$_2$, rt, 2 d;
f. TFA/CH$_2$Cl$_2$ (1:1)

Acidity of pH-gating Groups.

Acid-base equilibrium of α-amino groups is the key to pH-gated reactivity of these compounds. In order to obtain accurate information about this equilibrium, the pK$_a$ values of the three ammonium groups were measured using fluorescence and NMR spectroscopy. The two methods differ in the type of information and amount of detail that they provide.

Figure 4:
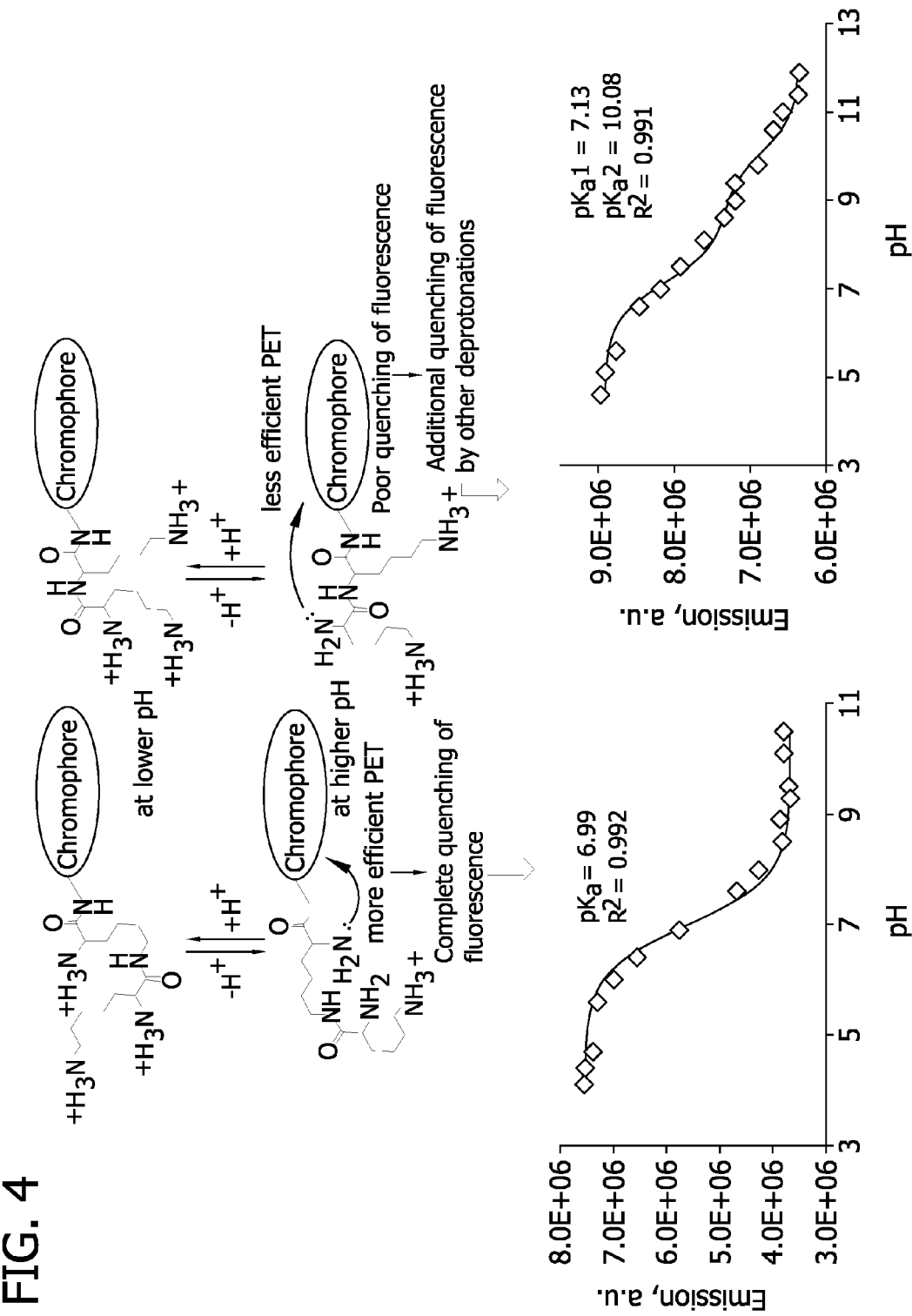
FIG. 4 is a schematic representation of electron transfer as means of quenching of fluorescence of an excited state chromophore and quantified changes in fluorescence intensity as a function of pH and their fit to the Henderson-Hasselbalch equation for acid-base equilibrium for bis-lysine di-α and di-ε conjugates (3) (left) and (5) (right).

Fluorescence Titrations:

Fluorescence directly reflects the protonation state of the α-amino group closest to the chromophore because the donor lone pair of the chromophore can quench the chromophore excited state via electron transfer. See FIG. 4, which depicts the electron transfer as a means for quenching fluorescence of an excited state chromophore. Changes in fluorescence intensity are quantified as a function of pH and their fit to the Henderson-Hasselbach equation for acid-base equilibrium for bis-lysine di-α and di-ε conjugates (3) (left side of FIG. 4) and (5) (right side of FIG. 4). Once the donor amine is protonated, this quenching mechanism is eliminated and a large increase in the fluorescence quantum yield is observed.

All pH titration experiments were carried out with only monoacetylene conjugates due to aggregation observed for the more hydrophobic enediyne conjugates at the higher pH. The pH titration with bis-lysine conjugate (3) showed only single titration curve corresponding to $pK_a$ of 7.0. The similarity of this value to the $pK_a$ of the α-amino group of monolysine conjugate (1) (7.0) and the similarly high efficiency of fluorescence quenching in the non-protonated form suggest that this pH titration curve corresponds to deprotonation of α-ammonium group.

In contrast, the pH titration with bis-lysine conjugate (5) has two titration curves with the pKa values of 7.1 and 10.1. Although conjugates (3) and (5) have a different number of ε-ammonium groups (one for (3) and two for (5)), the similarity in the first $pK_a$ values indicates that the α-amino group basicity does not depend strongly on the number of the ε-amino groups. In the pH titration of compound (5), the increase in the efficiency of fluorescence quenching due the first deprotonation is less pronounced (20% vs. 50% for (3)), likely due to the greater distance between the chromophore and the α-amino group. The relatively inefficient quenching of the excitation by the α-amino group should lead to the less pronounced efficiency of pH-modulation for the di-ε conjugate (5). The unexpected response of fluorescence of compound (5) to the protonation state of at least one of the two ε-amino groups may indicate presence of a folded conformation in the solution where one of the remote ammonium groups participates in a cation-π interaction with the chromophore or H-bonding with the amide group directly attached to the chromophore.

NMR Titration

To get the further insight into the acid-base equilibrium of these peptide systems with the atomic resolution, $^1$H-NMR pH titrations were carried out. The advantage of NMR titration is that it provides independent monitoring of each of the three protonation events through observations of chemical shifts for hydrogens spatially close to each of the amino groups. See Gao, G., DeRose, E. F., Kirby, T. W., London, R. E. NMR Determination of Lysine $pK_a$ Values in the Pol λ Lyase Domain: Mechanistic Implications. *Biochemistry*, 45, 1785, (2006). These studies followed changes in the chemical shifts of the individual protons from selected positions of the lysine chain upon the protonation/deprotonation of the three amino groups during the pH (pD) titration. To allow comparison of these $pK_a$s with $pK_a$s obtained by other methods, one has to take into account the difference between $pK_aH^*$, which is obtained by a direct reading of the $H_2O$-calibrated pH meter in a $D_2O$ solution, and $pK_a$ ($pK_a=0.929pK_aH^*+0.42$). $pK_a$ values measured with pH* are assumed to be similar to the corresponding values in $H_2O$: Primrose, W. U. *NMR of Macromolecules. A Practical Approach*; Poberts, G. C. K., Ed., Oxford University Press: Oxford, 1993, pp 22-23. See Scheller, K. H., Scheller-Krattiger, V., Martin, R. B. Equilibria in Solutions of Nucleosides, 5'-Nucleotides, and dienPd$^{2+}$ *J. Am. Chem. Soc.* 103, 6833-6839, (1981) and Krezel, A., Bal, Wojciech, A. A formula for correlating $pK_a$ values determined in $D_2O$ and $H_2O$. *J. Inorg. Biochem.* 98, 161-166, (2004).

Figure 5A:
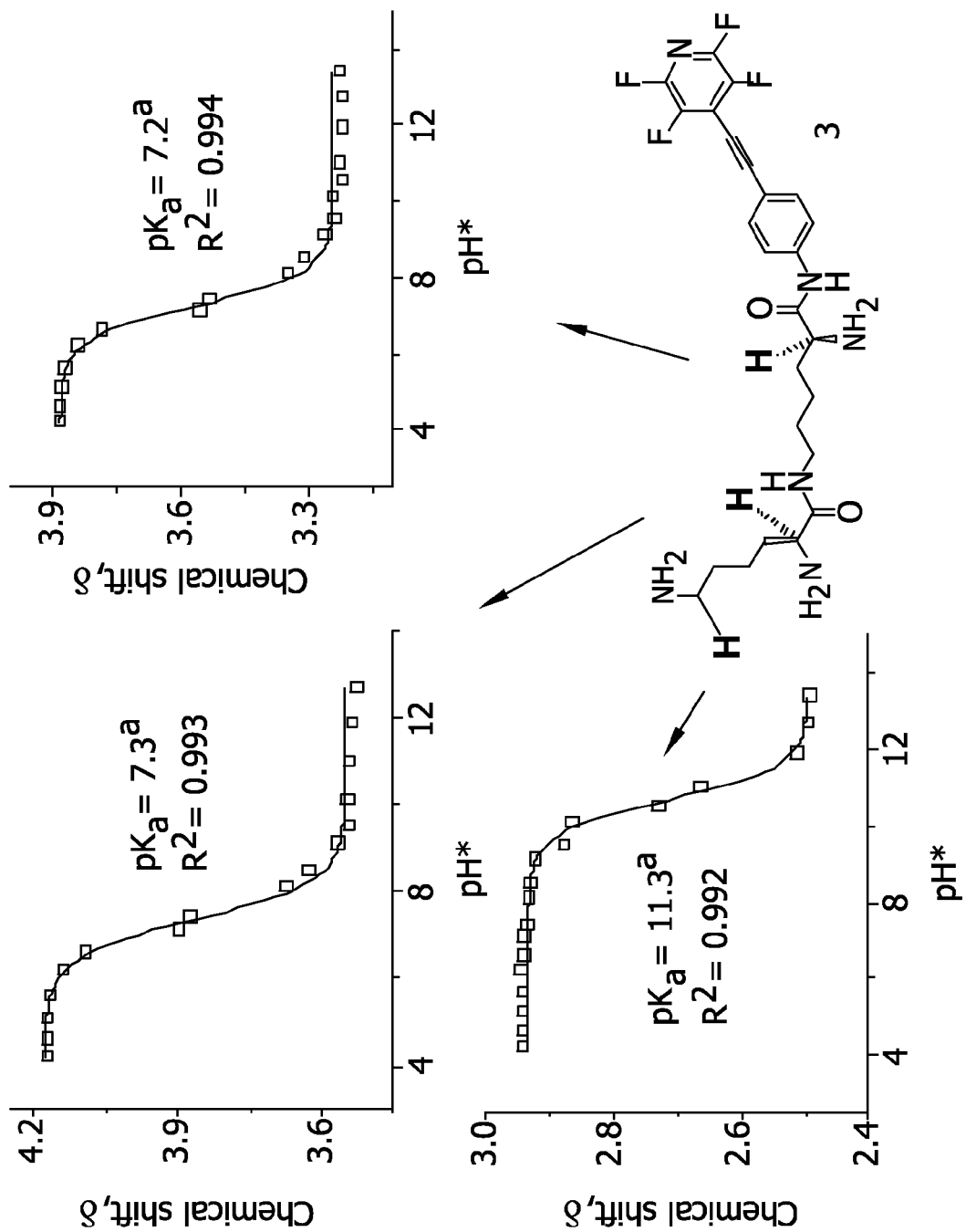
FIGS. 5A and 5B depict chemical shift-pD titration plots for α- and ε-hydrogens in conjugates (3.
Figure 5B:
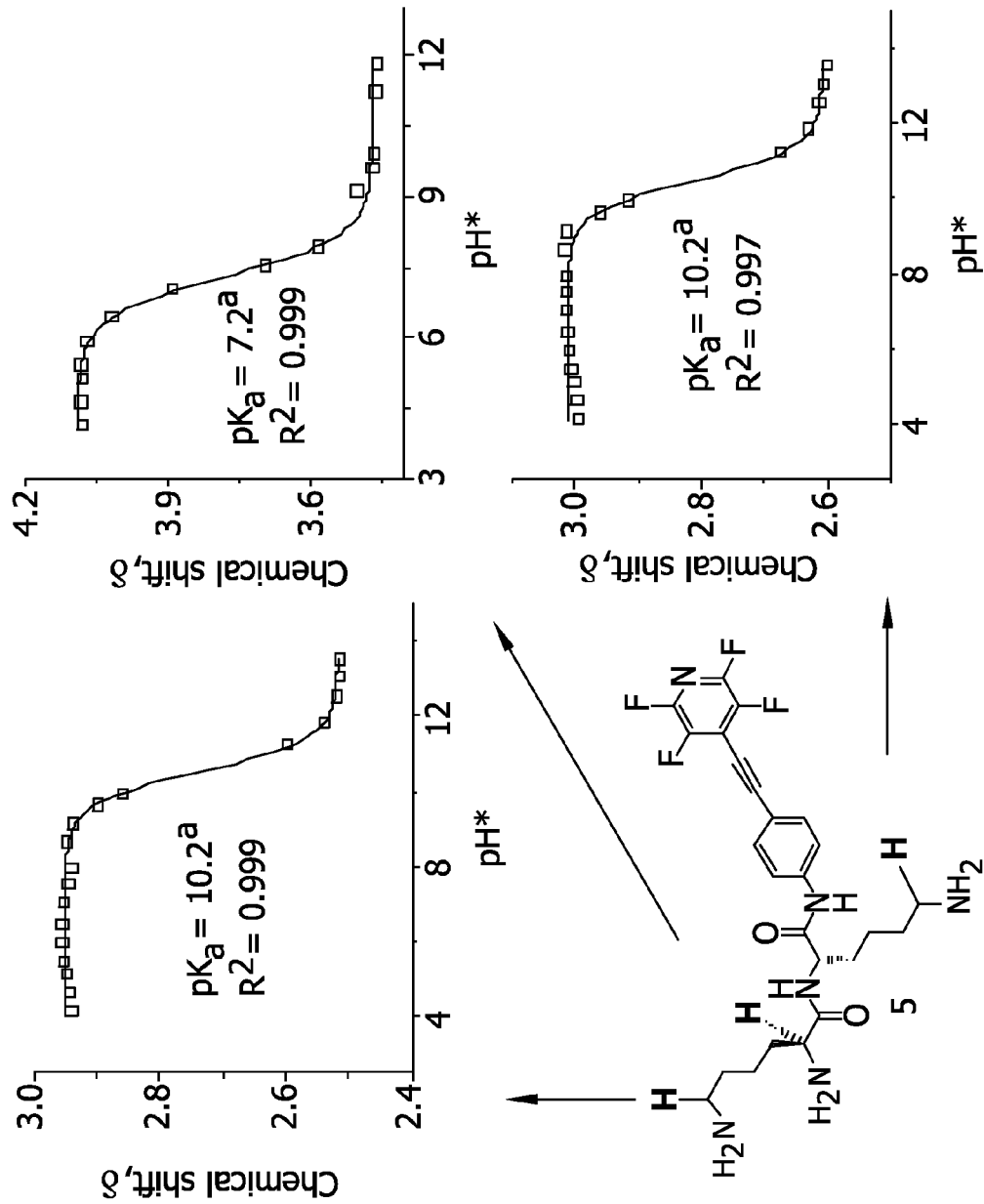

FIGS. 5A and 5B depict chemical shift $^1$H-NMR titration plots of two bis-lysine conjugates. Table 1 provides the $pK_a$ values for each of the amino groups in the bis-lysine conjugates. The titration curves for (3) shown in FIG. 5A clearly showed that two α-amino groups are less basic (pKa=7.2, 7.3) than ε-amino group (pKa=11.3). The NMR $pK_a$ values for (5) shown in FIG. 5B were 7.2 for α-amino group and 10.2 for both ε-amino groups. These $pK_a$ values are consistent with the values from the fluorometric titrations. The close $pK_a$ vales of the two α-amino groups (7.2 and 7.3) in (3) and of the two ε-amino groups (10.2) in (5) indicate again that the amino group basicity in these conjugates is not strongly affected by the protonation state of other amines, suggesting a lack of direct intramolecular interactions, e.g. H-bonding between the remote amino groups.

Interestingly, the very close pKa values of the two α-amino groups in (3) indicate that this molecule is converted from a monocation to a trication at a relatively narrow pH region between pH 7 and 8. In contrast, the isomeric conjugate (5) remains a dication at pH 8. Because conjugate (3) changes its protonation state from monocation to trication, this bis-peptide system is expected to respond stronger to the proton flux.

TABLE 1

The pKa values of amino groups in conjugates (3) and (5).
The first $pK_a$ for lysine conjugate (1) and lysine is given for comparison

| Compound Method | (3) Emission | (3) $^1$H-NMR$^a$ | (5) Emission | (5) $^1$H-NMR$^a$ | (1) Emission | Lysine |
|---|---|---|---|---|---|---|
| $pK_a1$ | 7.0 | 7.2 | 7.1 | 7.2 | 7.0 | 8.95$^b$ |
| $pK_a2$ | — | 7.3 | 10.1 | 10.2 | — | 10.53$^b$ |
| $pK_a3$ | — | 11.3 | — | 10.2 | — | — |

$^a$Data include a correction factor.
$^b$Data from Carey, F. A. *Organic Chemistry*, 6th ed.; McGraw Hill: New York, 2006.

Cleavage of Supercoiled DNA

Figure 6A:
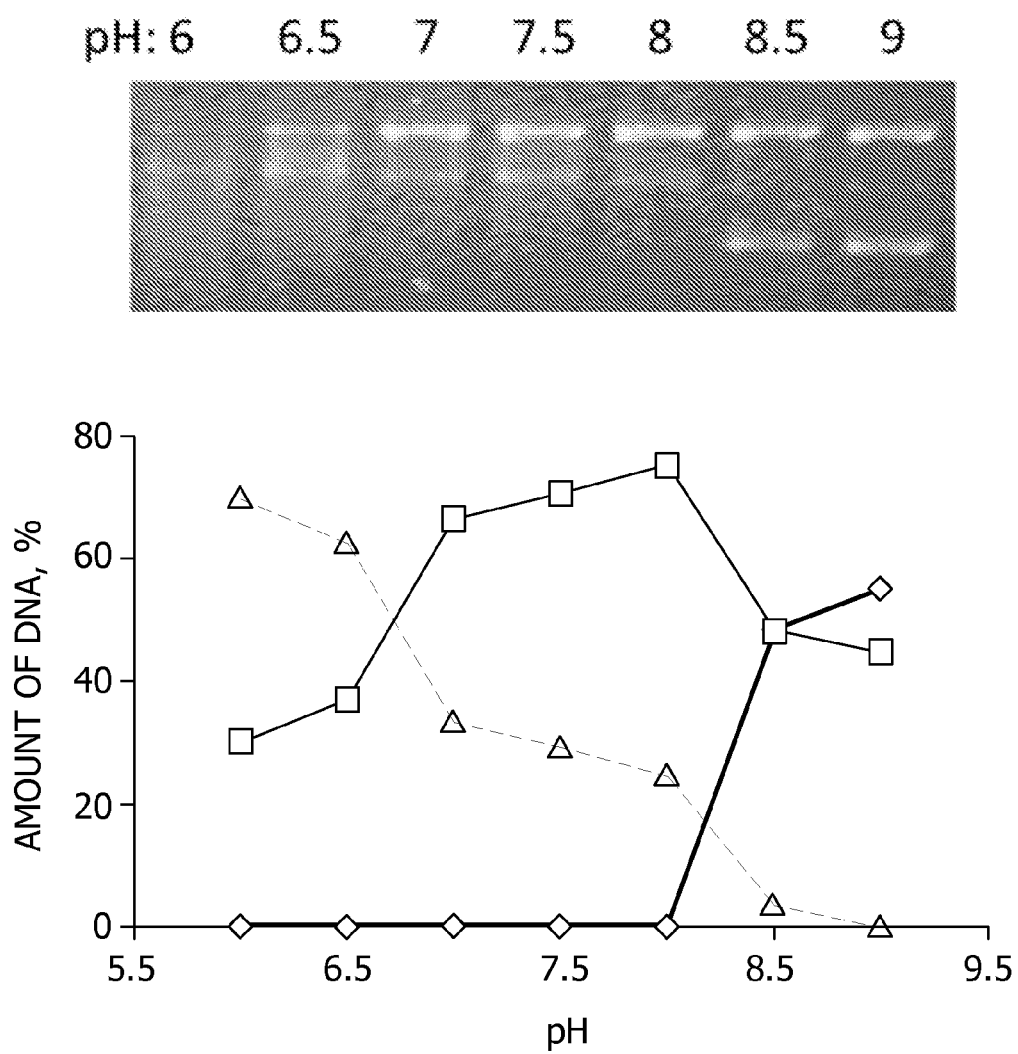
FIGS. 6A and 6B depict the pH-dependency of DNA-cleavage of two bis-lysine conjugates. The top of each of FIGS. 6A and 6B depict plasmid relaxation assay for DNA photocleavage with 15 μM of acetylenic conjugates (3) (FIG. 6A) and (5) (FIG. 6B) and 38 μM (b.p.) of pBR322 plasmid DNA at pH range of 6-9 after 10 min. of UV (>310 nm) irradiation. The bottom of each of FIGS. 6A and 6B are graphs of quantified cleavage data as a function of pH for conjugates (3) (FIG. 6A) and (5) (FIG. 6B). The reported values represent the average of three experiments. Code: Form I, diamond; Form II, square; Form III, triangle.
Figure 6B:
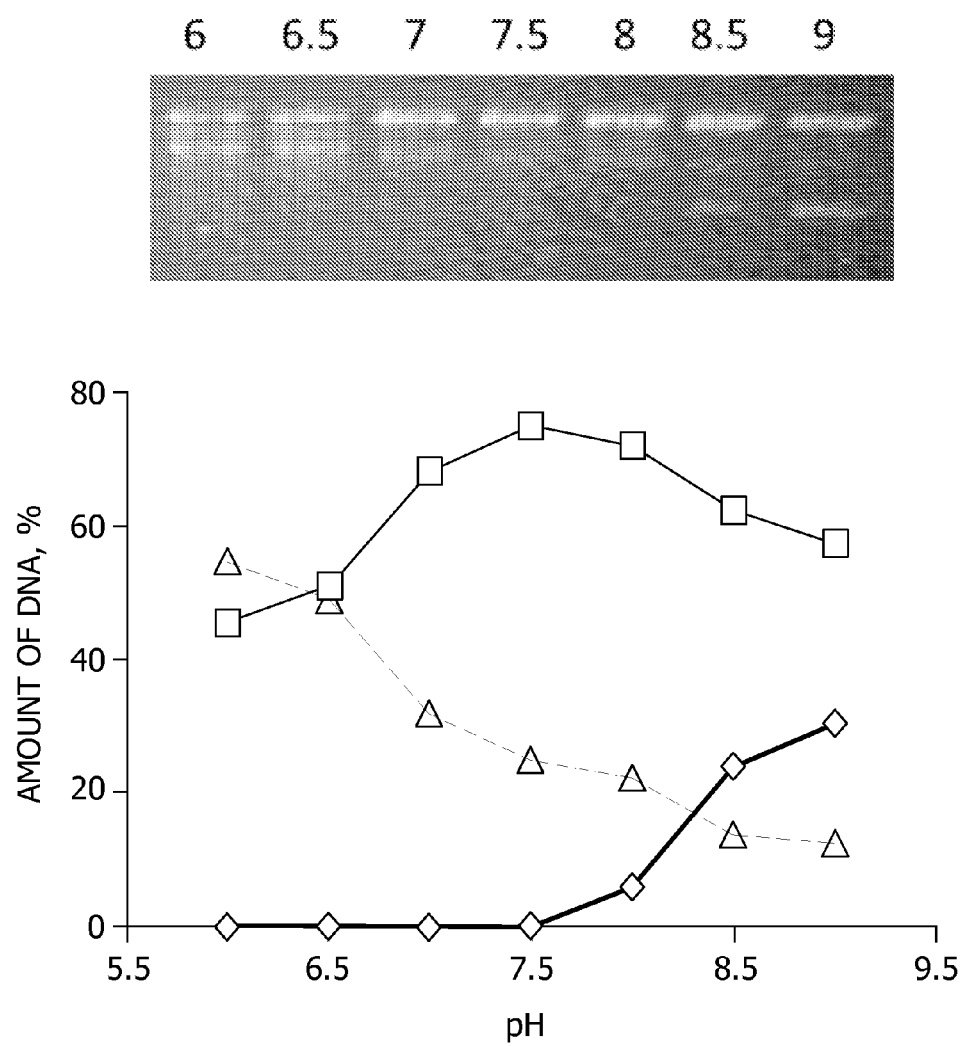

The present invention is additionally directed to methods of forming a double strand cleavage in DNA, wherein compounds having the above Structures are contacted with and bind to double stranded DNA. The pH-dependency of DNA-cleavage of the two bis-lysine conjugates was investigated. See FIGS. 6A and 6B. The top of FIGS. 6A and 6B depicts the results of the plasmid relaxation assay for DNA photocleavage with 15 μM of acetylenic conjugates (3) (FIG. 6A) and (5) (FIG. 6B) and 38 μM (b.p.) of pBR322 plasmid DNA at pH range of 6-9 after 10 min. of UV (>310 nm) irradiation. The bottom of each of FIGS. 6A and 6B are graphs of quantified cleavage data as a function of pH for conjugates (3) (FIG. 6A) and (5) (FIG. 6B). The reported values represent the average of three experiments. Code: Form I, diamond; Form II, square; Form III, triangle.

Not only both bis-lysine conjugates clearly showed enhancement of DNA cleavage as a function of pH but also the amount of ds-DNA cleavage produced by 15 μM of mono acetylene conjugates at pH 6 (ds:ss DNA cleavage ratios of 2:1 and 1:1 for di-α (3) and di-ε (5), respectively, FIGS. 6A and 6B) represents the highest ds:ss ratios reported in the literature, by far exceeding the analogous ratios for calicheamicin (1:2/1:3), bleomycin (1:6-1:10) and monolysine conjugates described by us earlier (1:2 at pH 6). See Tounekti, O., Kenani, A., Foray, N., Orlowski, S., Mir, L. M. The ratio of single- to double-strand DNA breaks and their absolute values determine cell death pathway. British Journal of Cancer. 84, 1272-1279, (2001); Povirk, L. F. Wübker, W., Steighner, R. J. Structure of bleomycin-induced DNA double-strand breaks: predominance of blunt ends and single-base 5' extensions. Biochemistry, 28, 5808-5814, (1989); Absalon, M. J., Kozarich, J. W., Stubbe, J. Sequence Specific Double-Strand Cleavage of DNA by Fe-Bleomycin. 1. The Detection of Sequence-Specific Double-Strand Breaks Using Hairpin Oligonucleotides. Biochemistry 34, 2065-2075, (1995); Stubbe, J., Kozarich, J. W., Wu, W,. Vanderwall, D. E. Bleomycins: A Structural Model for Specificity, Binding, and Double Strand Cleavage. Ace, Chem. Res. 29, 322-330, (1996); Charles, K., Povirk, L. F. Action of Bleomycin on Structural Mimics of Intermediates in DNA Double-Strand Cleavage. Chem. Res. Toxicol, 11, 1580-1585, (1998); and Grimwade, J. E., Beerman, T. A. Measurement of Bleomycin, Neocarzinostatin, and Auromomycin Cleavage of Cell-Free and Intracellular Simian Virus 40 DNA and Chromatin. Mol. Pharmacol. 30, 358-363, (1986).

Figure 7A:
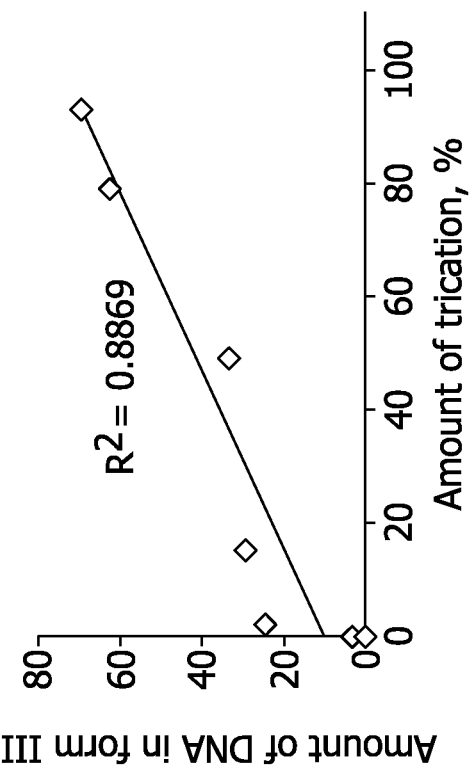
FIGS. 7A and 7B depict the relative amounts of mono- (solid line), di- (dashed line) and tri-cationic (dotted line) forms as function of pH (left) and the correlation of DNA ds-cleavage with the trication mole fraction (right) for conjugates (3) (FIG. 7A) and (5) (FIG. 7B).
Figure 7A:
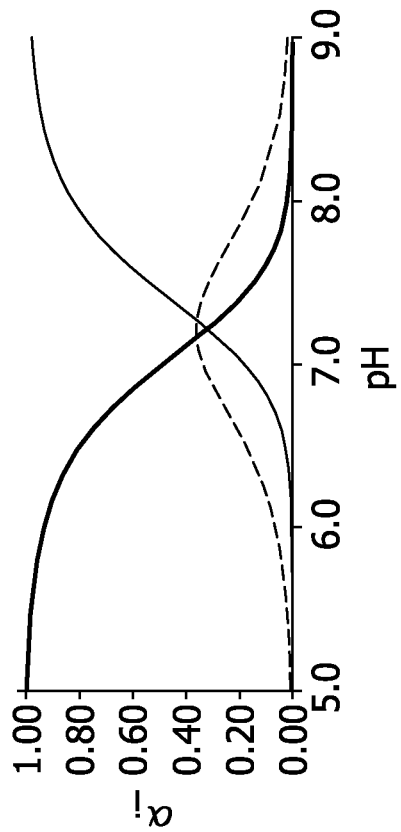
Figure 7B:
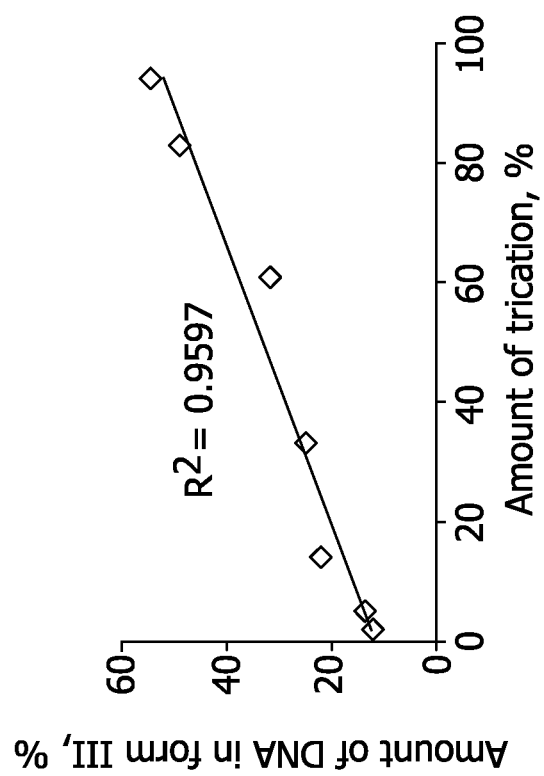
Figure 7B:
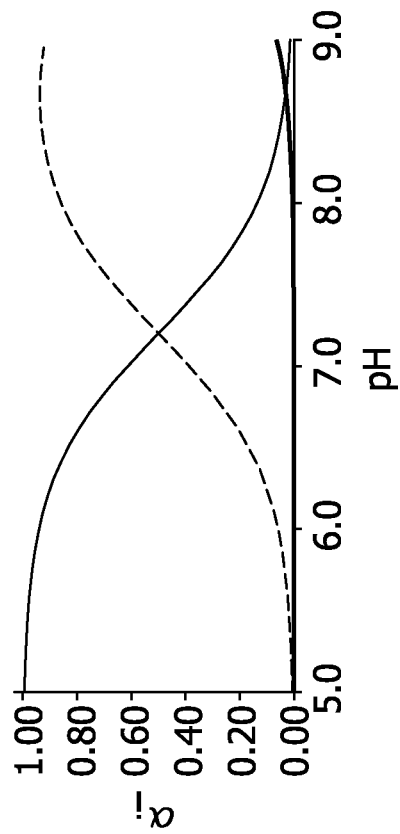

The bis-lysine conjugates of the invention show significant increase in the efficiency of ds-DNA cleavage in comparison to the analogous monolysine conjugates. The correlation between the efficiency of DNA cleavage and protonation state of the dipeptide moieties illustrated by FIGS. 7A and 7B. The graphs in FIGS. 7A and 7B depict the relative amounts of mono- (solid line), di- (dashed line) and tri-cationic (dotted line) forms as function of pH (left side graph) for each of conjugates (3) (FIG. 7A, left) and (5) (FIG. 7B, left). FIGS. 7A and 7B additionally provide the correlation of DNA ds-cleavage with the trication mole fraction (bottom) for conjugates (3) (FIG. 7A, right) and (5) (FIG. 7B, right). The data in FIGS. 7A and 7B suggest that the tricationic form plays a particularly significant role in the ds-cleavage. Interestingly, although the correlation is observed for both the di-α and di-ε peptides, it is stronger for the initially less efficient di-ε dipeptide (5). At the lower pH, the di-α conjugate (3) is so efficient that further cleavage of DNA into even smaller fragments is observed rendering the measurements less accurate and suggesting even more efficient DNA cleavage that the simple ds:ss ratio implies.

Figure 8A:
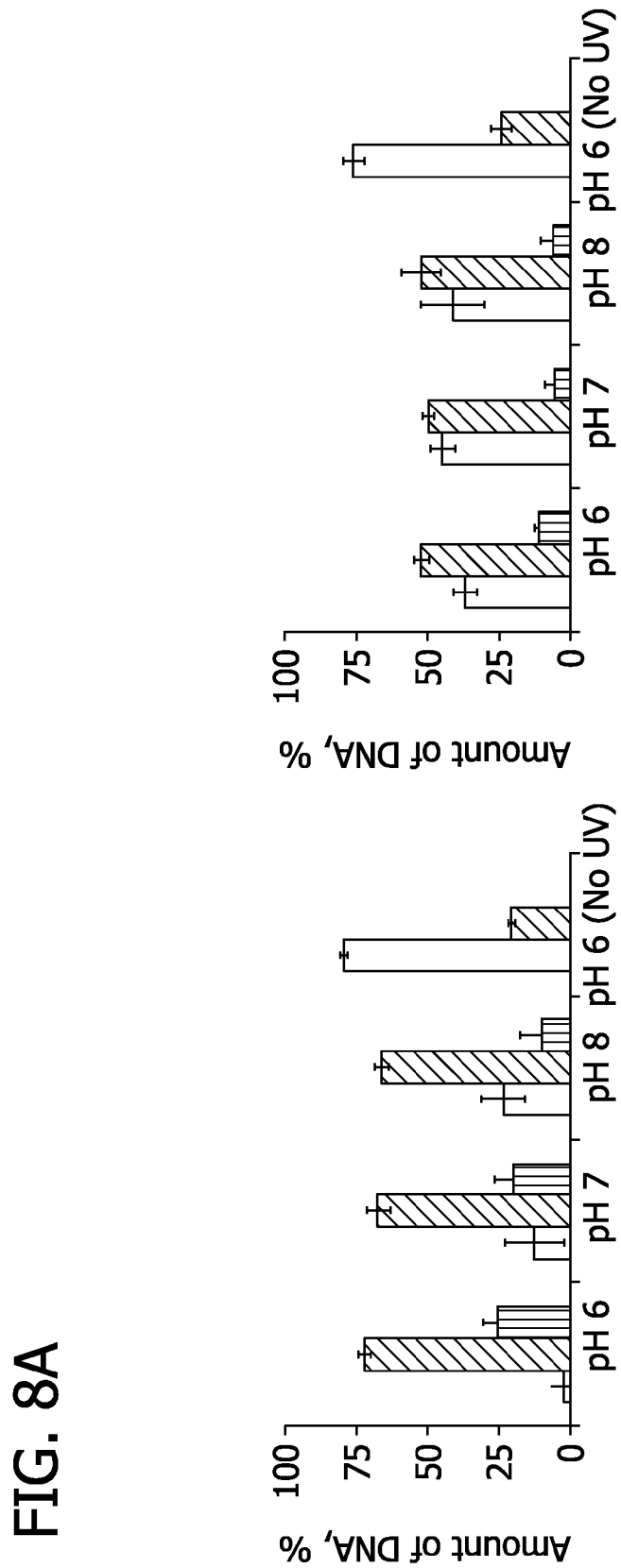
FIG. 8A depicts the quantified data of plasmid relaxation assays with 10 μM and 5 μM, respectively, of enediyne conjugate (4). Reported values represent the average of four experiments. White Bar: Form I DNA, Partially Shaded Bar: Form II DNA, black BAR: Form III DNA.
Figure 8B:
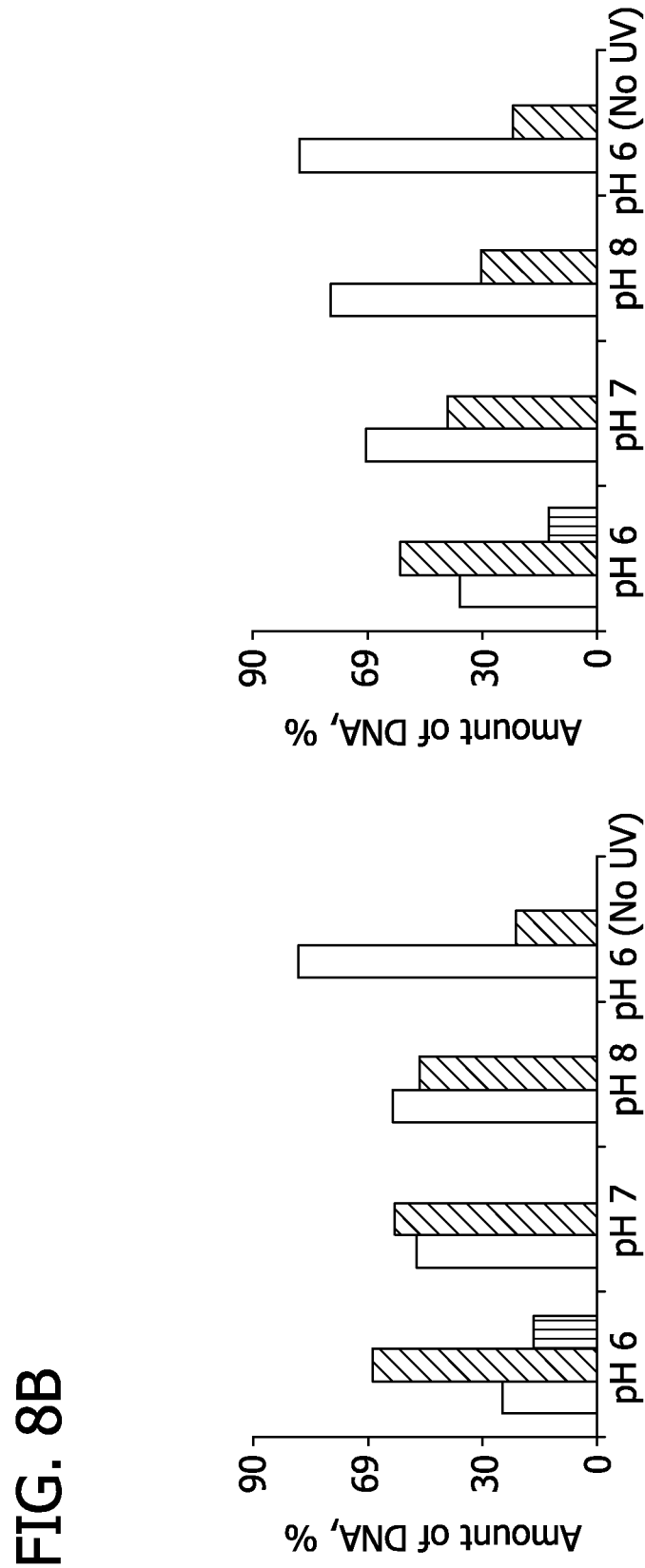
FIG. 8B depict the quantified data of plasmid relaxation assays with 10 μM and 5 μM, respectively, of enediyne conjugate (6). Reported values represent the average of four experiments. White Bar: Form I DNA, Partially Shaded Bar: Form II DNA, black BAR: Form III DNA.

Plasmid relaxation assays were carried out with 10 μM and 5 μM of enediyne conjugates (4) and (6). See FIGS. 8A and 8B. FIG. 8A depicts the quantified data of plasmid relaxation assays with 10 μM (left) and 5 μM (right) of enediyne conjugate (4). FIG. 8B depicts the quantified data of plasmid relaxation assays with 10 μM (left) and 5 μM (right) of enediyne conjugate (6). The reported values in FIGS. 8A and 8B represent the average of four experiments. White Bar: Form I DNA, Partially Shaded Bar: Form II DNA, black BAR: Form III DNA. Detailed spectroscopic studies on the analogous enediyne conjugates (4) and (6) are complicated by their lower solubility but both enedynes also show pH-gated ds-DNA damage at concentration as low as 5 μM. Although the ds:ss ratios were slightly lower (1:2.2 and 1:2.3, respectively, the total DNA damage by enediynes (4) and (6) at this concentration is comparable to the total damage by 10 μM of acetylene (3). Increase of enediyne concentration to 10 μM has not lead to proportionally large increase in DNA damage. This result is possibly due the observation that the enediyne conjugates less soluble than the respective acetylenes and form aggregates at higher concentrations. In particular, no DNA was detected after electrophoresis in plasmid relaxation assays at pH 6 with 15 μM enediyne bis-lysine conjugates. It might be due to formation of very large complex, which could not enter an agarose gel, due to the interaction of plasmid DNA and micelles formed from the amphilic conjugates. From a practical perspective, a particularly encouraging observation is the absence of ds damage at pH 7. The differences in the efficiency and pH-dependence of DNA cleavage by enediynes have two probable origins. Our earlier work suggested that enediyne and acetylene conjugates often bind DNA in a different way (e.g., intercalation vs. groove binding) and also may cause DNA damage via different mechanisms, e.g., C1-C5 cyclization vs. alkylation. See Alabugin, I. V., Kovalenko, S. V. C1-05 Photochemical Cyclization of Enediynes. *J. Am. Chem. Soc.,*124, 9052-9053, (2002) and Alabugin, I. V., Manoharan, M., Radical-Anionic Cyclizations of Enediynes: Remarkable Effects of Benzannelation and Remote Substituents on Cyclorearomatization Reactions, *J. Am. Chem. Soc.* 125, 4495-4509, (2003).

Synthesis of Regioisomeric Conjugates

In another embodiment, regioisomeric diaryl alkynes were synthesized as shown in the following Scheme 2. The Sonogashira coupling of the corresponding iodonitrobenzene with trimethylsilyl acetylene produced acetylenes (11a-c). In the context of Scheme 2, the compound "a" corresponds to the para- isomer, the compound "b" corresponds to the meta- isomer, and the compound "c" corresponds to the ortho- isomer. Trimethylsilyl (TMS) group of acetylene (11) was directly substituted to tetrafluoropyridyl (TFP) group using CsF-promoted reaction with pentafluoropyridine in DMF. Reduction of the nitrobenzenes (12a-c) with SnCl$_2$ produced anilines (13a-c) which reacted with acetyl chloride to form amides (14a-c).

Scheme 2. Synthesis of amidyl substituted mono acetylenes and lysine conjugates.

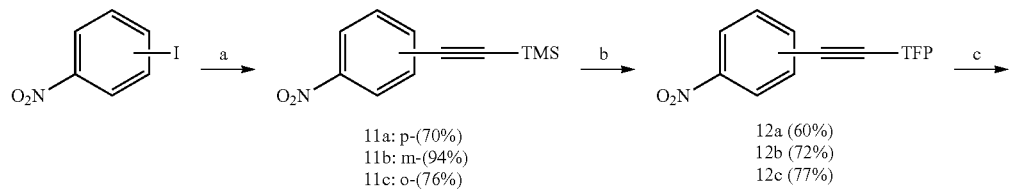

11a: p-(70%)
11b: m-(94%)
11c: o-(76%)

12a (60%)
12b (72%)
12c (77%)

-continued

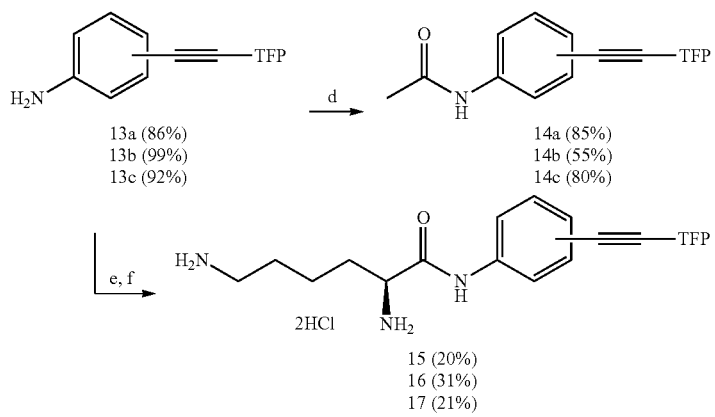

TFP = tetrafluoropyridinyl
Reagents and conditions:
a. PdCl$_2$(PPh$_3$)$_2$, CuI, HCCSiMe$_3$/Et$_3$N, rt,
b. CsF, pentfluoropyridine/DMF,
c. SnCl$_2$, EtOH, reflux,
d. (CH$_3$CO)$_2$O, Et$_3$N/CH$_2$Cl$_2$,
e. POCl$_3$, Boc-Lys(Boc)—OH/pyridine,
f. HCl(g)/MeOH Conjugates (15), (16), and (17) were prepared via coupling of the corresponding anilines (13a-c) with Boc-protected lysine in the presence of POCl$_3$ in pyridine. The Boc groups were removed via treatment with gaseous HCl in MeOH.
Photophysics and Kinetics of Photoinduced Electron Transfer The fluorescence quenching by triethylamine (Et$_3$N) was tested in order to gauge relative efficiencies of these compounds as DNA photo-oxidizers. In the quenching experiments, the meta isomer (4) showed the largest Stern-Volmer constant ($K_{sv}$=45.51) among the three isomers whereas the previously patented para isomer (3) displayed the lowest efficiency of quenching. See Table 2. The measured singlet lifetimes allowed us to determine the quenching rate constant, $k_q$, which in this system, should be very close in magnitude to the rate of electron transfer, $k_{ET}$. The 2-3-fold increase in the rate of electron transfer from Et$_3$N to excited singlet state of the meta- and ortho-isomers in comparison to the para-isomer is consistent with the well-known photochemical ortho, meta effect of an acceptor substituent. See Zimmerman, H. E., The Meta Effect in Organic Photochemistry: Mechanistic and Exploratory Organic Photochemistry, J. Am. Chem. Soc., 1995, 117, 8988-8991. doi: 10.1021/ja00140a014 and Zimmerman, H. E.; Alabugin, I. V. J. Am. Chem. Soc. 2001, 121, 226-2270. doi: 10.1021/ja002402c.

Although fluorescence of all three isomers is quenched by the amine, the efficient quenching of singlet excitation in compound (4) can potentially lead to a stronger pH-dependency on the photochemistry of the respective lysine conjugate which is controlled by the protonation-gated intramolecular electron transfer from the α-amino group. See Yang, W-Y.; Breiner, B.; Kovalenko, S. V.; Ben, C.; Singh, M.; LeGrand, S. N.; Sang, Q-X.; Strouse, G. F.; Copland, J. A.; Alabugin, I. V. J. Am. Chem. Soc. 2009, 131, 11458-11470. doi: 10.1021/ja902140m.

TABLE 2

Stern-Volmer quenching constants (Et$_3$N as a quencher) and singlet lifetimes for the isomeric acetylenes 3-5.

| Compound | $K_{sv}$, M$^{-1}$ | τ, ns | $k_q$, Ms$^{-1}$ |
|---|---|---|---|
| (3) (para) | 7.11 | 1.26 ± 3.22 × 10$^{-3}$ | 5.64 × 10$^9$ |
| (4) (meta) | 45.5 | 3.35 ± 9.30 × 10$^{-3}$ | 1.36 × 10$^{10}$ |
| (5) (ortho) | 19.1 | 1.34 ± 3.52 × 10$^{-3}$ | 1.43 × 10$^{10}$ |

Interestingly, the meta-isomer has a noticeably longer singlet lifetime than the other two isomers. A similar trend has been observed previously for the lifetimes of m-substituted enediynes. See Kauffman, J. F.; Turner, J. M.; Alabugin, I. V.; Breiner, B.; Kovalenko, S. V.; Badaeva, E. A.; Masunov A., Tretiak, S. J. Phys. Chem. A 2006, 110, 241-251. doi: 10.1021/jp056127y.

Whereas the core Ph-TFP-acetylene (Ph-TFP) chromophore without the amide group has no significant absorption at >320 nm. The lowest absorptions of the para and ortho isomers (3), (5) are shifted to the red: ($λ_{max}$~330 nm) as a consequence of increased conjugation in the ground state. In contrast, the absorption of the meta isomer (4) is closer to that of Ph-TFP with the lower energy absorption band displayed as a lower intensity shoulder
Efficiency of DNA Photocleavage The plasmid relaxation assay experiments were carried out on 15 μM of lysine conjugate with 30 μM/base pair of pBR322 plasmid DNA at pH 6, 7 and 8. The DNA cleaving ability of conjugates does not directly follow the order of the photocycloaddition of their acetamides. Although the m-substituted acetylene was more photoreactive towards 1,4-cyclohexadiene, the corresponding conjugate (16) produced less DNA cleavage than conjugate (15). This suggests that either the difference in DNA binding overshadows the intrinsic differences in reactivity or that the acetamide group is not a good surrogate for the lysine amides.

Nevertheless, both p- and m-lysine conjugates exhibit efficient dsDNA damage at pH 6 where the α-amino group of the lysine moiety is protonated and incapable of direct interference with the singlet photochemistry. On the other hand, compound (17) which is unlikely to be a strong alkylating agent in the excited state showed the least efficient DNA cleavage which has not produced any double-strand breaks. Interestingly, all three C-lysine conjugates broke DNA more efficiently at lower pH.

Cell Proliferation Assay

Figure 9A:
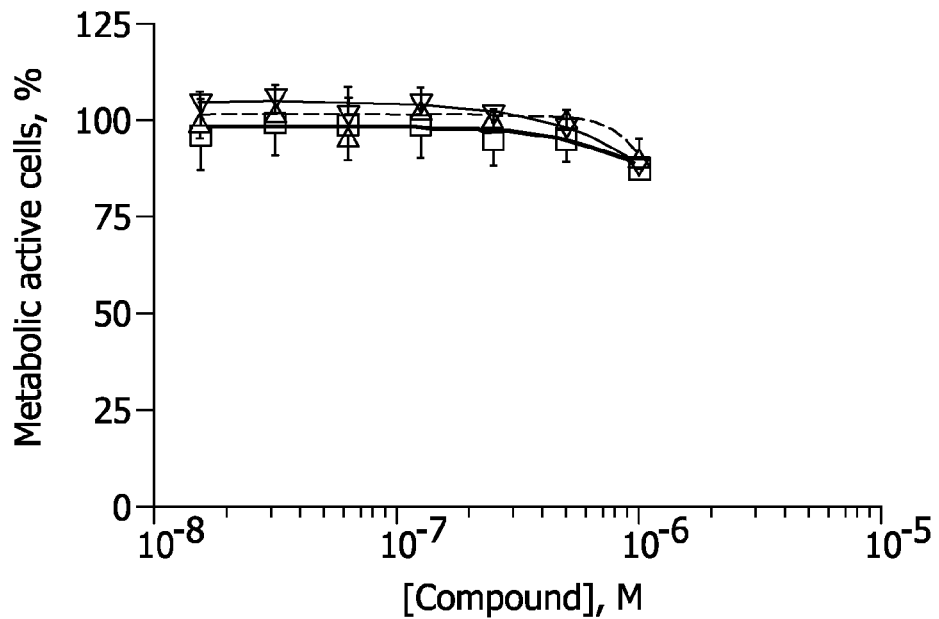
FIGS. 9A and 9B depicts cell proliferation assays in A375 cells (Human Melanoma) exposed to bis-lysine conjugates (15) (square), (16) (up-pointing triangle) and (17) (down-pointing triangle) in dark (FIG. 9A) and after 10 min. of UV (360 nm) irradiation (FIG. 9B).
Figure 9B:
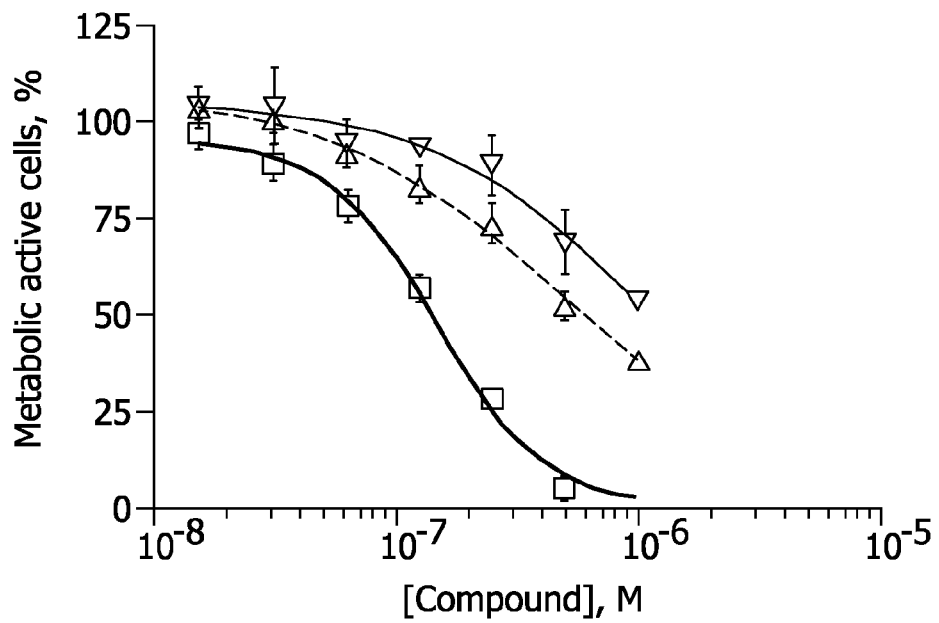

The ability of compounds (15), (16), and (17) to inhibit cell proliferation in human melanoma cell lines was tested in the dark and under photoactivation. See FIGS. 9A and 9B, which depict cell proliferation assays in A375 cells (Human Melanoma) exposed to bis-lysine conjugates (15) (square), (16) (up-pointing triangle) and (17) (down-pointing triangle) in dark (FIG. 9A) and after 10 min. of UV (360 nm) irradiation (FIG. 9B). According to the control experiments with all three conjugates in the dark, these compounds do not inhibit cell proliferation at the concentration <1 μM. On the other hand, conjugate (1) displayed strong phototoxicity towards the human melanoma A375 cell line at the nanomolar range ($CC_{50}=1.49 \times 10^{-7}$ M) after 10 minute of UV irradiation at 360 nm. Conjugate (6) and (7) also showed some phototoxicity. This result of cell proliferation inhibition by the conjugates is consistent with their respective DNA cleaving abilities.

Having described the invention in detail, it will be apparent that modifications and variations are possible without departing from the scope of the invention defined in the appended claims.

EXAMPLES

The following non-limiting examples are provided to further illustrate the present invention.

General information. $^1$H NMR and $^{13}$C NMR spectra were collected on a Varian Gemini 300 MHz, Bruker 400 MHz and 600 MHz NMR spectrometer. Mass spectrometry data was collected on a Jeol JMS-600H. UV spectra were recorded on a Shimadzu UV-2100. Fluorescence spectra were obtained with SPEX FluoMax spectrofluorimeter using right-angle geometry. pH was monitored with AB 15 plus pH meter (Accument) after standardization at 25° C. All buffers were prepared and pH was adjusted with HCl (aq.) and NaOH (aq.) at room temperature (25° C.)

Singlet excitation lifetime. The singlet excitation lifetimes were measured using the time-correlated single photon counting (TCSPC) technique. The samples were excited at 295 nm wavelength with LED operating at a repetition rate of 1MHz. The emission decay was observed at emission $\lambda_{max}$ of each sample and data were recorded with 10,000 counts in the peak channel. The timescale of the experiment was 200 ns (29.19 ps/channel). The decay data were analyzed with DAS6 software.

Plasmid DNA Photocleavage. pBR322 plasmid DNA (4,361 bp; from BioLabs Inc., 1 μg/μL solution in 10 mM Tris-HCl (pH 8.0), and 1mM EDTA buffer) was diluted to a concentration of 0.01 μg/μL. The solution containing cleavage agent, DNA (30 μM/bp) in 20 mM sodium phosphate buffer was incubated for 1 hour at 30° C. Samples were placed on ice at a distance of 20 cm from 200 W Hg—Xe lamp (Spectra-Physics, Laser & Photonics Oriel Instruments with long pass filter with 300 nm cut-on wavelength).

Electrophoretic Analysis. The gel electrophoresis was carried out in 1x TBE buffer at 80 V using Miligel FisherBiotech Horizontal Electrophoresis System. All gels were run on 1% agarose slab gels. Before loading, the DNA samples were mixed with 0.33 volume of tracking dye containing bromophenol blue (0.25%) and glycerol (30%) in water. After staining in ethidium bromide solution (2 μg/mL) for 1 hour, the gel was washed with water and pictures were taken. The relative quantities of the supercoiled, nicked, and linear DNA were calculated by integrating the "area" of each spot by the image analyzer software Total/Lab (Nonlinear Dynamics Ltd., UK). The amount of supercoiled DNA was multiplied by factor of 1.4 to account for reduced ethidium bromide intercalation into supercoiled DNA.

Cell culture. The human cancer cell line used in this report was obtained from the American Type Culture Collection (ATCC®). The human mesothelioma cell line MSTO-211H (CRL-2081™) were cultured in RPMI 1640 medium supplemented with 10% fetal bovine serum (FBS) and penicillin/ streptomycin (Life Technologies™). Cells were propagated according to ATCC guidelines and maintained in a 37° C. incubator with 5% $CO_2$ atmosphere.

MTT Assay. A375 cells were seeded at 2000 cells per well in a 96-well plate. Seven 2-fold serial dilutions of the compounds were added to the cells in triplicate. Concentrations were from 1 to 0.016 μM of compounds. After 4 hs of incubation with the compounds, cells were UV-irradiated for ten minutes at 365 nm (UV transluminator, Spectronomics Corp. model TR-365R). After 72hs of incubation, MTT (Sigma® cat#M2128) was added to cells to a final concentration of 1.25 mg/mL and incubated for 60 minutes. Cells were centrifuged at 900 g for 5 minutes at room temperature. Media was replaced with DMSO and absorbance will be measured in a plate reader at 570 nm.

Synthesis of compounds. All reagents used were obtained from commercial sources and were of the highest grade available.

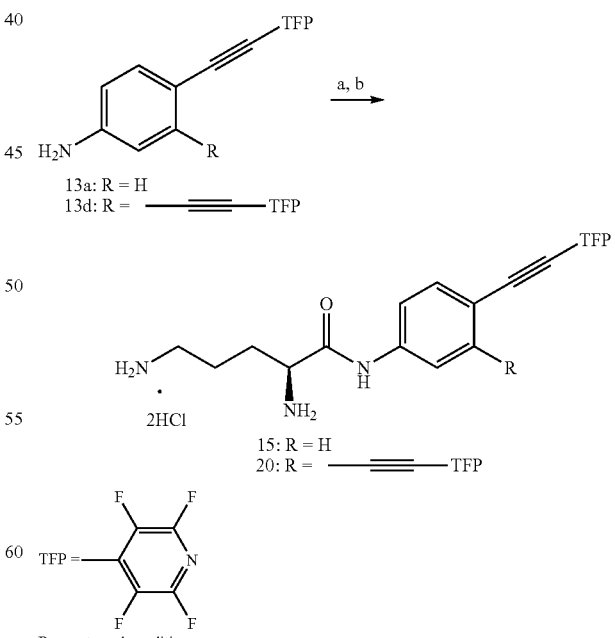

Scheme 3. Synthesis of ornithine conjugates.

13a: R = H
13d: R = ———≡———TFP

15: R = H
20: R = ———≡———TFP

Reagents and conditions:
a. $N^a$—Boc—Orn($N^d$—Boc)—OH, DCC, DMAP, $CH_2Cl_2$, rt, 2 d;
b. HCl(g)/MeOH (or THF)

(S)-2,5-Diamino-N-(4-((perfluoropyridin-4-yl)ethynyl)phenyl)pentanamide Dihydrochloride (15)

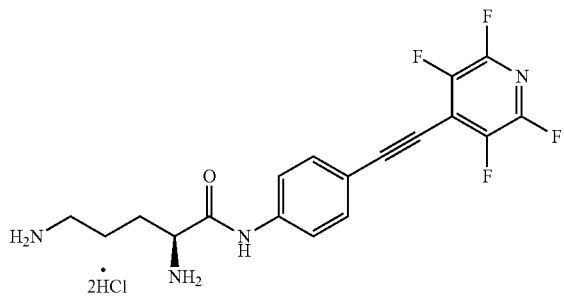 [SMILES: NCCC[C@H](N)C(=O)Nc1ccc(C#Cc2c(F)c(F)nc(F)c2F)cc1]

L-Boc-Orn(Boc)-OH (0.25 g, 0.75 mmol) was dissolved in 1.5 mL of pyridine. The solution was cooled to −25° C. and phosphorus oxychloride (0.12 g, 0.75 mmol) was added dropwise with vigorous stirring. After stirring for 15 min. at −25° C., 4-((perfluoropyridin-4-yl)ethynyl)aniline, (13a) (0.10 g, 0.38 mmol) in pyridine (1.5 mL) was added slowly. The reaction mixture was stirred for 0.5 h at −25° C. and then at room temperature for 10 h. The reaction mixture was quenched with ice/water and extracted with EtOAc. The organic layer was washed with sat. NaHSO$_4$ three times, dried with Na$_2$SO$_4$ and was concentrated in vacuo. The crude product was subjected to chromatography with MeOH:CH$_2$Cl$_2$=1:80 and the Boc-protected product was obtained in 23% yield. (S)-Di-tert-butyl (5-oxo-5-((4-((perfluoropyridin-4-yl)ethynyl)phenyl)amino)pentane-1,4-diyl)dicarbamate (100 mg, 0.17 mmol) was dissolved in gaseous HCl saturated MeOH (4 mL) at 0° C. and the solution was stirred for 10 hours at room temperature. The precipitated product (40 mg, 51%) was obtained by filtration: $^1$H-NMR (300 MHz, CD$_3$OD) δ 7.82 (d, J=9.0 Hz, 2H), 7.65 (d, J=8.7 Hz, 2H), 4.15 (t, J=6.3 Hz, 1H), 3.14 (t, J=8.4 Hz, 2H), 2.02-2.09 (m, 2H), 1.83-1.88 (m, 2H)

(S)-2,5-Diamino-N-(3,4-bis((perfluoropyridin-4-yl)phenyl)pentanamide Dihydrochloride (20)

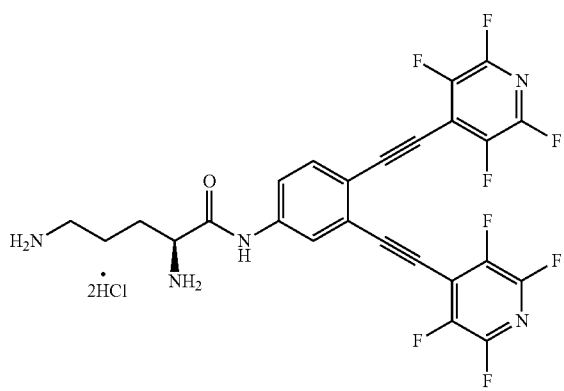 [SMILES: NCCC[C@H](N)C(=O)Nc1ccc(C#Cc2c(F)c(F)nc(F)c2F)c(C#Cc2c(F)c(F)nc(F)c2F)c1]

L-Boc-Orn(Boc)-OH (0.15 g, 0.46 mmol) was dissolved in 1.5 mL of pyridine. The solution was cooled to −25° C. and phosphorus oxychloride (0.14 g, 0.92 mmol) was added dropwise with vigorous stirring. After stirring for 15 min. at −25° C., compound (13d) (0.10 g, 0.23 mmol) in pyridine (1.5 mL) was added slowly. The reaction mixture was stirred for 1 h at −25° C. and then at room temperature for 2 h. The reaction mixture was quenched with ice/water and extracted with EtOAc. The organic layer was washed with sat. NaHSO$_4$ three times, dried with Na$_2$SO$_4$ and was concentrated in vacuo. The crude product was subjected to chromatography with 1% MeOH in CH$_2$Cl$_2$ and the Boc-protected product was obtained in 25% yield. Into the solution of (S)-di-tert-butyl (5-((3,4-bis((perfluoropyridin-4-yl)ethynyl)phenyl)amino)-5-oxopentane-1,4-diyl)dicarbamate (21 mg, 0.03 mmol) in THF was gaseous HCl bubbled at 0° C. for 1 hr and the solution was stirred for 1 hour at room temperature. The solvent was evaporated and the residue was washed with Et$_2$O several times to obtain the product (12 mg, 71%): $^1$H-NMR (300 MHz, CD$_3$OD) δ 8.19 (s, 1H), 7.80 (d, J=8.7 Hz, 1H), 7.69 (d, J=9.0 Hz, 1H), 4.10 (t, J=7.5 Hz, 1H), 2.93 (t, J=7.5 Hz, 2H), 1.88-2.11 (m, 2H), 1.63-1.87 (m, 2H)

N-(4-((Perfluoropyridin-4-yl)ethynyl)phenyl)acetamide (14a)

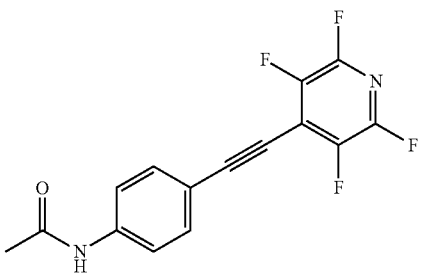 [SMILES: CC(=O)Nc1ccc(C#Cc2c(F)c(F)nc(F)c2F)cc1]

Into the solution of 4-((Perfluoropyridin-4-yl)ethynyl)aniline, (13a) (0.158 g, 0.59 mmol) in 3 mL of CH$_2$Cl$_2$ were added acetic anhydride (0.134 g, 1.26 mmol) and Et$_3$N (0.128 g, 1.26 mmol). The reaction mixture was stirred at room temperature overnight. After concentrating the solution in vacuo, the product was isolated by column chromatography (EtOAc:Hexane=1:2 to 1:1) with 85% yield: $^1$H-NMR (400 MHz, CD$_3$OD) δ 7.70 (d, J=8.6 Hz, 2H), 7.59 (d, J=8.6 Hz, 2H), 2.15 (s, 3H); $^{13}$C-NMR (150 MHz, CD$_3$CN) δ 170.1, 144.5 (dm, J=237 Hz), 143.1 (dm, J=259 Hz), 142.7, 134.2, 120.0, 115.4, 107.5 (t, J=3.4 Hz), 73.6 (t, J=4.3 Hz), 24.5; HRMS (ESI+): calcd for C$_{15}$H$_9$F$_4$N$_2$O$_1$ [M+H]$^+$ 309.06510, found 309.06678; m.p. 189-190° C.

Trimethyl((3-nitrophenyl)ethynyl)silane (11b)

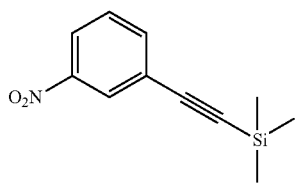

A mixture of 3-iodonitrobenzene (2.0 g, 8.0 mmol), bis(triphenylphosphine)palladium(II) chloride (0.30 g, 0.40 mmol) and copper(I) iodide (0.080 g, 0.40 mmol) in 25 mL of Et$_3$N was degassed by freeze/pump/thaw technique (three times). Trimethylsilylacetylene (1.0 g, 10 mmol) was added and the mixture was stirred for 12 hours. The reaction mixture was filtered through a celite pad and the pad was rinsed with CH₂Cl₂. The filtrate was washed with sat. NH₄Cl (aq.) and brine and the organic layer was dried (Na₂SO₄), filtered, and concentrated. The residue was purified by column chromatography (Hexane, then EtOAc;Hexanes =1:30) to afford trimethyl((3-nitrophenyl)ethynyl)silane (1.65 g, 94%): ¹H-NMR (300 MHz, CDCl₃) δ 8.32 (dd, J=1.8, 1.8 Hz, 1H), 8.17 (ddd, J=8.4, 2.1, 0.9 Hz, 1H), 7.76 (ddd, J=7.5, 1.2, 1.2 Hz, 1H), 7.49 (dd, J=8.1, 8.1 Hz, 1H), 0.28 (s, 9H).

2,3,5,6-Tetrafluoro-4-((3-nitrophenyl)ethynyl)pyridine (12b)

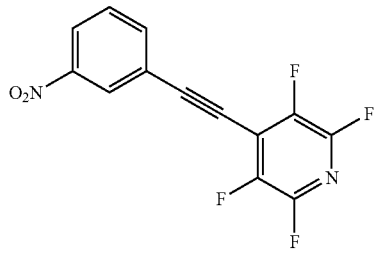 [SMILES: O=[N+]([O-])c1cccc(C#Cc2c(F)c(F)nc(F)c2F)c1]

A solution of trimethyl((3-nitrophenyl)ethynyl) silane, (11b) (1.45 g, 6.61 mmol) in DMF (10 mL) was added to the mixture of pentafluoropyridine (1.45 g, 8.59 mmol) and CsF (1.51 g, 9.92 mmol) in DMF (10 mL) slowly. The reaction mixture was stirred overnight. Brine (30 mL) and dichloromethane (60 mL) were added. Organic phase was separated and washed with water (30 mL×3). Solvent was evaporated by rotary evaporation and the residue was chromatographed (Hexane, then EtOAc:Hexane=1:30) to provide the desired product in 72% yield: ¹H-NMR (300 MHz, CDCl₃) δ 8.49 (dd, J=1.8, 1.8 Hz, 1H), 8.35 (ddd, J=8.4, 2.1, 0.9 Hz, 1H), 7.96 (ddd, J=7.8, 1.2, 1.2 Hz, 1H), 7.66 (dd, J=8.1, 8.1 Hz, 1 H); ¹³C-NMR (75 MHz, CDCl₃) δ 148.2, 143.5 (dm, J=247.6 Hz), 141.9 (dm, J=264.0 Hz), 129.9, 127.0, 125.1, 122.2, 116.3 (tt, J=16.0, 4.4 Hz), 102.9 (t, J=3.5 Hz), 75.2 (t, J=4.2 Hz); HRMS (CI+): calcd for C₁₃H₅F₄N₂O₂ [M+H]⁺ 297.02872, found 297.02908; m.p. 130-131° C.

3-((Perfluoropyridin-4-yl)ethynyl)aniline (13b)

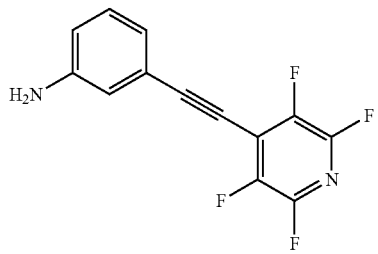

SnCl₂ (3.94 g, 20.8 mmol) was added to the solution of 2,3,5,6-tetrafluoro-4-((3-nitrophenyl)ethynyl) pyridine, (12b) (1.23 g, 4.15 mmol) in EtOH (100 mL). The reaction mixture was refluxed for 1.5 hours. After basification till pH>9 with NaOH (1.0 N solution), the product was extracted with dichloromethane. Solvent was evaporated and 0.73 g (66%) of the product aniline was purified by recrystallization with benzene. The residue was purified by column chromatography on silica gel using EtOAc:Hexane=1:5 as the eluent to yield the product (0.37 g, 33%): ¹H-NMR (300 MHz, CDCl₃) δ 7.21 (dd, J=7.2, 7.2 Hz, 1H), 7.03 (d, J=7.5 Hz, 1H), 6.93 (s, 1H), 6.79 (dd, J=7.4, 1.5 Hz, 1H), 3.80 (s, 2H); ¹³C-NMR (150 MHz, CDCl₃) δ 146.7, 143.6 (dm, J=241.8 Hz), 142.0 (dm, J=262.4 Hz), 129.8, 122.8, 121.4, 118.2, 117.7 (m), 117.6, 107.4 (t, J=3.8 Hz), 72.9 (t, J=4.3 Hz); HRMS (ESI+): calcd for C₁₃H₇F₄N₂ [M+H]⁺ 267.05454, found 267.05405; m.p. 172-173° C.

N-(3-((Perfluoropyridin-4-yl)ethynyl)phenyl)acetamide (14b)

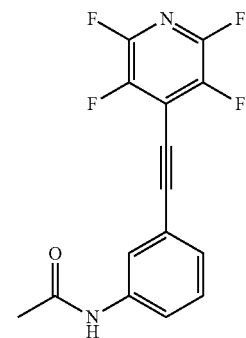 [SMILES: CC(=O)Nc1cccc(C#Cc2c(F)c(F)nc(F)c2F)c1]

Into the solution of 3-((Perfluoropyridin-4-yl)ethynyl) aniline, (13b) (0.200 g, 0.751 mmol) in 3 mL of CH₂Cl₂ were added acetyl anhydride (0.116 g, 1.13 mmol) and Et₃N (0.114 g, 1.13 mmol). The reaction mixture was stirred at room temperature overnight. After concentrating the solution in vacuo, the product was isolated by column chromatography (EtOAc:Hexane=1:2 to 1:1) with 55% yield: ¹H-NMR (400 MHz, CD₃OD) δ 7.96 (s, 1H), 7.64 (d, J=8.0 Hz, 1H), 7.42 (dd, J=7.7 Hz, J=7.7 Hz, 1H), 7.36 (d, J=7.7 Hz, 1H), 2.15 (s, 3H); ¹³C-NMR (100 MHz, CDCl₃) δ 168.5, 143.6 (dm, J=249 Hz), 142.0 (dm, J=263 Hz), 138.4, 129.6, 128.3, 123.3, 122.1, 121.4, 117.3 (m), 106.2 (m), 73.6 (m), 24.8; HRMS (ESI+): calcd for C₁₅H₉F₄N₂O₁ [M +H]⁺ 309.06510, found 309.06584; m.p. 215-216° C.

(S)-2,6-Diamino-N-(3-((perfluoropyridin-4-yl)ethynyl)phenyl)hexanamide Dihydrochloride (16)

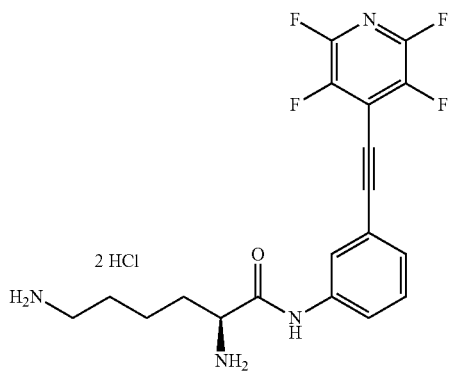 [SMILES: NCCCC[C@H](N)C(=O)Nc1cccc(C#Cc2c(F)c(F)nc(F)c2F)c1]

L-Boc-Lys(Boc)-OH (0.26 g, 0.75 mmol) was dissolved in 3 mL of pyridine. The solution was cooled to −25° C. and phosphorus oxychloride (0.12 g, 0.75 mmol) was added dropwise with vigorous stirring. After stirring for 15 min. at −25° C., 3-((perfluoropyridin-4-yl)ethynyl)aniline, (13b) (0.10 g, 0.36 mmol) in pyridine (3 mL) was added slowly. The reaction mixture was stirred for 0.5 h at −25° C. and then at room temperature for 10 h. The reaction mixture was quenched with ice/water and extracted with EtOAc. The organic layer was washed with sat. NaHSO₄ three times, dried with Na₂SO₄ and was concentrated in vacuo. The crude product was subjected to chromatography with CH₂Cl₂:CH₃CN=1:30 and the product was obtained in 36% yield. (S)-Di-tert-butyl (6-oxo-6-((3-((perfluoropyridin-4-yl)ethynyl)phenyl)amino)hexane-1,5-diyl)dicarbamate (97 mg, 0.16 mmol) was dissolved in gaseous HCl saturated MeOH (4 mL) at 0° C. and the solution was stirred for 10 hours at room temperature. The solvent was evaporated and the product (65 mg, 86%) was purified by recrystallization with isopropanol: ¹H-NMR (600 MHz, CD₃OD) δ 8.07 (dd, J=1.74 Hz, J=1.68 Hz, 1H), 7.75 (ddd, J=7.98 Hz, J=1.92 Hz, J=1.14 Hz, 1H), 7.48 (dd, J=7.8 Hz, J=7.8 Hz, 1H), 7.43 (ddd, J=7.68 Hz, J=1.32 Hz, J=1.32 Hz, 1H) 4.12 (t, J=6.6 Hz, 1H), 2.97 (t, J=7.56 Hz, 2H), 2.00-2.07 (m, 1H), 1.97-2.00 (m, 1H), 1.74-1.77 (m, 2H), 1.56-1.60 (m, 2H); ¹³C-NMR (150 MHz, CD₃OD) δ 168.7, 144.9 (dm, J=224 Hz), 143.5 (dm, J=262 Hz), 139.7, 130.8, 129.4, 124.2, 123.3, 122.4, 117.9 (m), 106.5 (m), 74.2 (m), 54.9, 40.3, 32.2, 28.2, 23.0; m.p. >250° C. (decomp.)

Trimethyl((2-nitrophenyl)ethynyl)silane (11c)

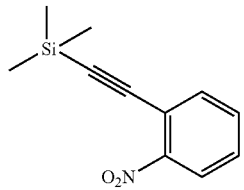

A mixture of 2-iodonitrobenzene (2.0 g, 8.0 mmol), bis(triphenylphosphine)palladium(II) chloride (0.30 g, 0.40 mmol) and copper(I) iodide (0.080 g, 0.40 mmol) in 25 mL of Et₃N was degassed by freeze/pump/thaw technique (three times). Trimethylsilylacetylene (1.0 g, 10 mmol) was added and the mixture was stirred for 18 hours. The reaction mixture was filtered through a celite pad and the pad was rinsed with CH₂Cl₂. The filtrate was washed with sat. NH₄Cl (aq.) and brine and the organic layer was dried (Na₂SO₄), filtered, and concentrated. The residue was purified by column chromatography (Hexane, then EtOAc:Hexane=1:60, 1:30) to afford trimethyl((2-nitrophenyl)ethynyl)silane (1.33 g, 76%): ¹H-NMR (300 MHz, CDCl₃) δ 8.02 (dd, J=8.1, 1,2 Hz, 1H), 7.66 (dd, J=7.5, 1.5 Hz, 1H), 7.56 (ddd, J=7.2, 7.2, 1.2 Hz, 1H), 7.45 (ddd, J=8.1, 8.1, 1.5 Hz, 1H), 0.28 (s, 9H).

2,3,5,6-Tetrafluoro-4-((2-nitrophenyl)ethynyl)pyridine (12c)

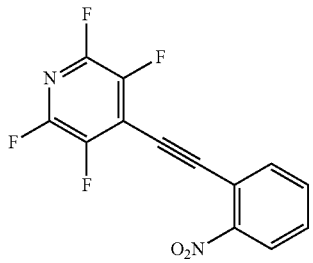

A solution of Trimethyl((2-nitrophenyl)ethynyl) silane, (11c) (1.10 g, 5.02 mmol) in DMF (10 mL) was added to the mixture of pentafluoropyridine (1.08 g, 6.53 mmol) and CsF (1.10 g, 7.52 mmol) in DMF (10 mL) slowly. The reaction mixture was stirred overnight. Brine (30 mL) and dichloromethane (60 mL) were added. Organic phase was separated and washed with water (30 mL×3). Solvent was evaporated by rotary evaporation and the residue was chromatographed (Hexane, then EtOAc:Hexane =1:30) to provide the desired product in 77% yield: ¹H-NMR (300 MHz, CDCl₃) δ 8.24 (dd, J=7.8, 1.5 Hz, 1H), 7.85 (dd, J=7.5, 1.5 Hz, 1H), 7.73 (ddd, J=7.5, 7.5, 1.5 Hz, 1H), 7.66 (ddd, J=7.8, 7.8, 1.5 Hz, 1H); ¹³C-NMR (150 MHz, CDCl₃) δ 149.7, 143.7 (dm, J=234.1 Hz), 142.1 (dm, J=264.7 Hz), 135.5, 133.5, 131.2, 125.3, 116.7 (t, J=16.3 Hz), 116.2, 100.9 (t, J=3.2 Hz), 79.8 (t, J=4.1 Hz); HRMS (CI+): calcd for C₁₃H₅F₄N₂O₂ [M+H]⁺ 297.02872, found 297.02911; m.p. 109-110° C.

2-((Perfluoropyridin-4-yl)ethynyl)aniline (13c)

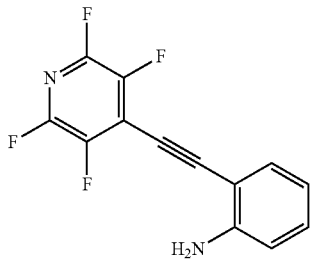 [SMILES: O=[N+]([O-])c1ccccc1C#Cc1c(F)c(F)nc(F)c1F]

SnCl₂ (3.26 g, 17.2 mmol) was added to the solution of 2,3,5,6-tetrafluoro-4-((2-nitrophenyl)ethynyl) pyridine, (12c) (1.02 g, 3.44 mmol) in EtOH (100 mL). The reaction mixture was refluxed for 1.5 hours. After basification till pH>9 with NaOH (1.0 N solution), the product was extracted with dichloromethane. Solvent was evaporated and 0.22 g (24%) of the product aniline was purified by recrystallization with benzene. The residue was purified by column chromatography on silica gel using EtOAc:Hexane=1:10 as the eluent to yield the product (0.53 g, 68%): ¹H-NMR (300 MHz, acetone-d₆) δ 7.39 (d, J=7.5 Hz, 1H), 7.26 (ddd, J=8.4, 6.9, 1.5 Hz, 1H), 6.89 (d, J=8.4 Hz, 1H), 6.69 (ddd, J=7.5, 7.5, 1.2 Hz, 1H), 5.35 (s, 2H); ¹³C-NMR (150 MHz, CDCl₃) δ 149.3, 143.7 (dm, J=245.3 Hz), 141.4 (dm, J=260.9 Hz), 133.0, 132.6, 118.3, 117.8 (m), 114.8, 104.7, 104.6 (t, J=3.5 Hz), 79.4 (t, J=4.3 Hz); HRMS (ESI+): calcd for C₁₃H₇F₄N₂ [M+H]⁺ 267.05454, found 267.05454; m.p. 133-134° C.

N-(2-((Perfluoropyridin-4-yl)ethynyl)phenyl) acetamide (14c)

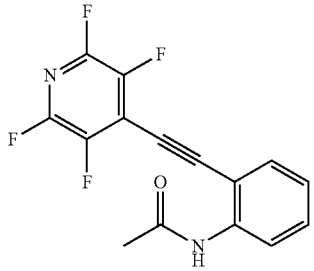 [SMILES: CC(=O)Nc1ccccc1C#Cc1c(F)c(F)nc(F)c1F]

Into the solution of 3-((Perfluoropyridin-4-yl)ethynyl) aniline, (13b) (0.078 g, 0.29 mmol) in 1.5 mL of CH₂Cl₂ were added acetyl anhydride (0.044 g, 0.44 mmol) and Et₃N (0.044 g, 0.44 mmol). The reaction mixture was stirred at room temperature for 1 day. After concentrating the solution in vacuo, the product was isolated by column chromatography (EtOAc:Hexane=1:3 to 1:1) with 80% yield: ¹H-NMR (400

MHz, CD₃CN) δ 8.24 (brs, 1H), 8.09 (d, J=7.9 Hz, 1H), 7.64 (d, J=7.9 Hz, 1H), 7.53 (dd, J=7.3 Hz, J=7.3 Hz, 1H), 7.22 (dd, J=7.6 Hz, J=7.6 Hz, 1 H), 2.16 (s, 3H); $^{13}$C-NMR (100 MHz, CDCl₃) δ 168.5, 143.9 (dm, J=199.1 Hz), 141.4 (dm, J=220.5 Hz), 140.3, 132.7, 132.5, 123.9, 120.1, 116.9 (m), 109.2, 102.3, 80.7, 24.9; HRMS (ESI+): calcd for C₁₅H₉F₄N₂O₁ [M+H]⁺ 309.06510, found 309.06417; m.p. 204.2-205° C.

(S)-2,6-Diamino-N-(2-((perfluoropyridin-4-yl)ethynyl)phenyl)hexanamide Dihydrochloride (17)

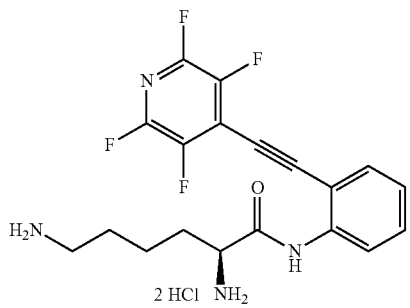 [SMILES: NCCCC[C@H](N)C(=O)Nc1ccccc1C#Cc1c(F)c(F)nc(F)c1F]

L-Boc-Lys(Boc)-OH (0.52 mg, 1.5 mmol) was dissolved in 3 mL of pyridine. The solution was cooled to −25° C. and phosphorus oxychloride (0.23 g, 1.5 mmol) was added dropwise with vigorous stirring. After stirring for 15 min. at −25° C., 2-((perfluoropyridin-4-yl)ethynyl)aniline, 13c (0.20 g, 0.75 mmol) in pyridine (3 mL) was added slowly. The reaction mixture was stirred for 0.5 h at −25° C. and then at room temperature for 10 h. The reaction mixture was quenched with ice/water and extracted with EtOAc. The organic layer was washed with sat. NaHSO₄ three times, dried with Na₂SO₄ and was concentrated in vacuo. The crude product was subjected to chromatography with CH₂Cl₂:CH₃CN=1:30 and the desired product was obtained in 24% yield. (S)-Di-tert-butyl (6-oxo-6-((2-((perfluoropyridin-4-yl)ethynyl)phenyl)amino)hexane-1,5-diyl)dicarbamate (185 mg, 0.31 mmol) was dissolved in gaseous HCl saturated MeOH (6 mL) at 0° C. and the solution was stirred for 10 hours at room temperature. The solvent was evaporated and the product (124 mg, 86%) was purified by recrystallization with isopropanol: ¹H-NMR (300 MHz, CD₃OD) δ 7.89 (d, J=8.1 Hz, 1H), 7.72 (dd, J=7.8, 1.5 Hz, 1H), 7.58 (ddd, J=7.2, 1.2, 1.5 Hz, 1H), 7.36 (ddd, J=7.2, 7.2, 1.2 Hz, 1H), 4.20 (t, J=6.2 Hz, 1H), 2.96 (t, J=7.5 Hz, 2H), 1.98-2.19 (m, 2H), 1.71-1.81 (m, 2H), 1.56-1.70 (m, 2H); $^{13}$C-NMR (100 MHz, CD₃OD) δ 169.1, 144.9 (dm, J=240.9 Hz), 143.2 (dm, J=259.8 Hz), 139.5, 134.6, 132.8, 127.4, 125.9, 118.1 (m), 116.0, 103.2 (t, J=3.6 Hz), 79.6 (t, J=4.3 Hz), 54.8, 40.3, 32.2, 28.2, 23.1; HRMS (CI+): calcd for C₁₉H₁₉F₄N₄O₁ [M+H]⁺ 395.1495, found 395.1487; m.p. 222-223° C. (decomp.)

Scheme 4. Synthesis of ortho-lysine enediyne conjugate.

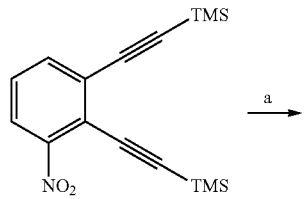

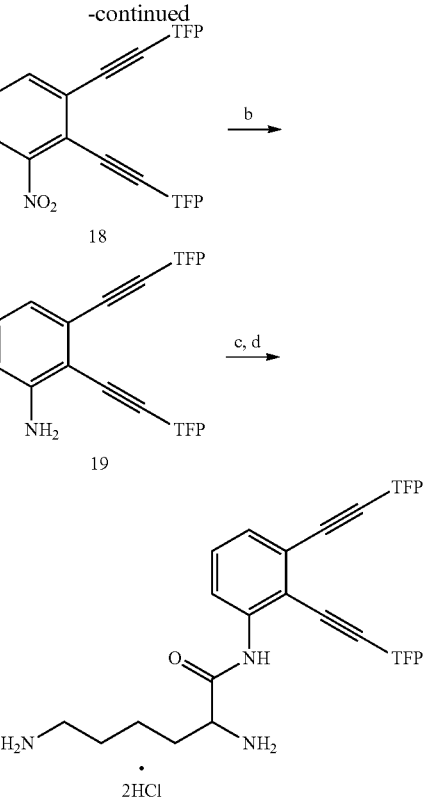

Reagents and conditions:
a. CsF, pentfluoropyridine/DMF
b. SnCl₂, HCl (aq)/THF,
c. POCl₃, Boc-Lys(Boc)—OH/pyridine,
d. HCl(g)/THF 4,4'-((3-Nitro-1,2-phenylene)bis(ethyne-2,1-diyl))bis(2,3,5,6-tetrafluoropyridine) (18)

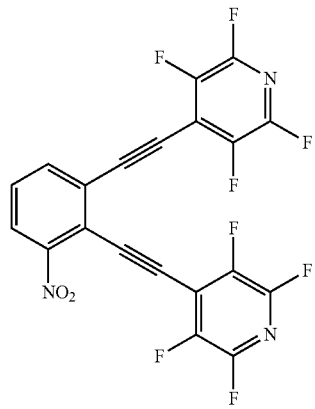

A solution of ((3-nitro-1,2-phenylene)bis(ethyne-2,1-diyl))bis(trimethylsilane) (2.89 g, 9.16 mmol) in DMF (20 mL) was added into 20 mL of CsF(4.17 g, 27.5 mmol) solution in DMF. Into the mixture, pentafluoropyridine (3.87 g, 22.9 mmol) was added slowly at 0° C. The reaction mixture was stirred for 20 hrs, and brine (50 mL) and dichloromethane (100 mL) were added. Organic phase was separated and washed with water (50 mL×3). Solvent was evaporated by rotary evaporation and the residue was chromatographed (CH₂Cl₂:Hexane=1:4 to 1:3) to provide the desired product in 42% yield: $^1$H-NMR (300 MHz, CDCl₃) δ 8.28 (dd, J=8.1 Hz, J=1.2 Hz, 1H), 8.02 (dd, J=7.8 Hz, J=1.2 Hz, 1H), 7.71 (dd, J=8.4 Hz, J=8.4 Hz, 1H)

2,3-Bis((perfluoropyridin-4-yl)ethynyl)aniline (19)

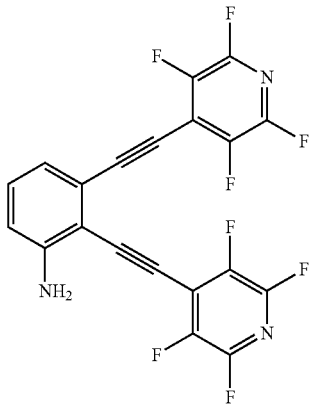 [SMILES: O=[N+]([O-])c1cccc(C#Cc2c(F)c(F)nc(F)c2F)c1C#Cc1c(F)c(F)nc(F)c1F]

SnCl₂ (5.8 g, 31 mmol) and 1.5 mL of conc. HCl (aq) were added to the solution of 4,4'-((3-Nitro-1,2-phenylene)bis(ethyne-2, 1-diyl))bis (2,3,5,6-tetrafluoropyridine), (18) (1.45 g, 3.1 mmol) in 30 mL of THF. The reaction mixture was stirred for 1 day. After basification till pH>9 with NaOH (1.0 N solution), the product was extracted with dichloromethane. Solvent was evaporated and 0.4 g (31%) of the product aniline was purified by recrystallization: $^1$H-NMR (300 MHz, CDCl₃) δ 7.29 (m, 1H), 7.09 (d, J=7.8 Hz, 1H), 6.87 (d, J=8.4 Hz, 1H), 4.58 (s, 2H)

2,6-Diamino-N-(2,3-bis((perfluoropyridin-4-yl)ethynyl)phenyl)hexanamide Dihydrochloride (20)

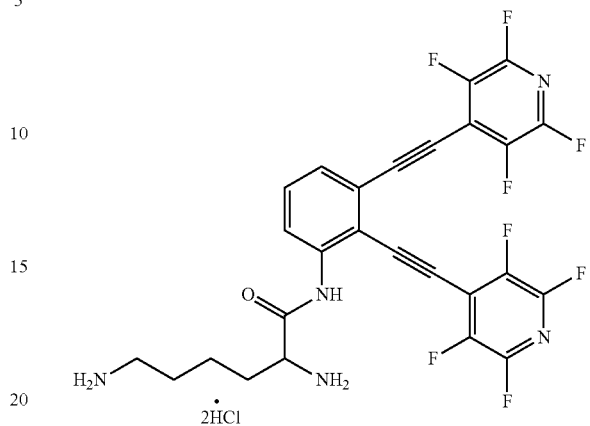

L-Boc-Lys(Boc)-OH (0.31 g, 0.91 mmol) and compound (19) (0.20 g, 0.46 mmol) were dissolved in 2 mL of pyridine. The solution was cooled to −25° C. and phosphorus oxychloride (0.14 g, 0.91 mmol) was added dropwise with vigorous stirring. After stirring for 30 min. at -25° C., the reaction mixture was stirred at room temperature for 10 h. The reaction mixture was quenched with ice/water and extracted with EtOAc. The organic layer was washed with sat. NaHSO₄ three times, dried with Na₂SO₄ and was concentrated in vacuo. The crude product was subjected to chromatography with CH₃CN:CH₂Cl₂=1:40 and the Boc-protected product was obtained in 26% yield. Into the solution of the Boc-protected lysine conjugate (85 mg, 0.11 mmol) in THF was gaseous HCl bubbled at 0° C. for 1 hr and the solution was stirred for 1 hour at room temperature. The solvent was evaporated and the desired product (46 mg, 65%) was purified by recrystallization with EtOH: $^1$H-NMR (300 MHz, CD₃OD) δ 8.07 (dd, J=6.3 Hz, J=3.0 Hz, 1H), 7.69 (m, 2H), 4.26 (dd, J=7.5 Hz, J=5.4 Hz, 1H), 2.98 (t, J=H7.2 Hz, 2H), 2.01-2.21 (m, 2H), 1.75-1.81 (m, 2H), 1.60-1.75 (m, 2H).

Scheme 5. Synthesis of Ala-Lys (ε-NH₂) conjugates

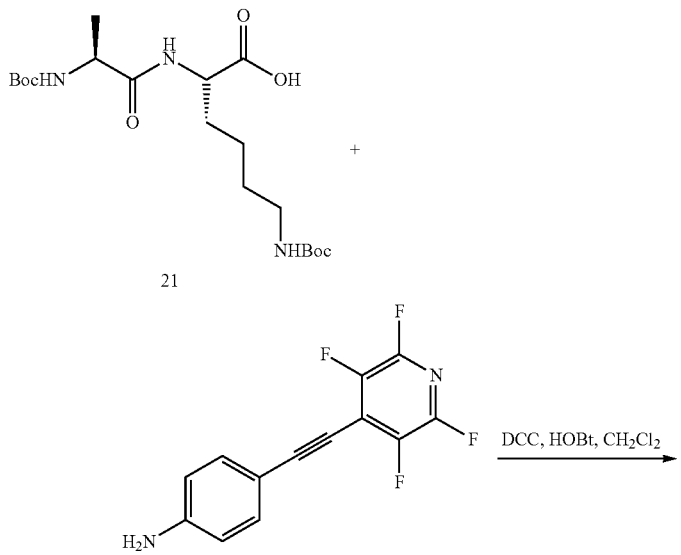

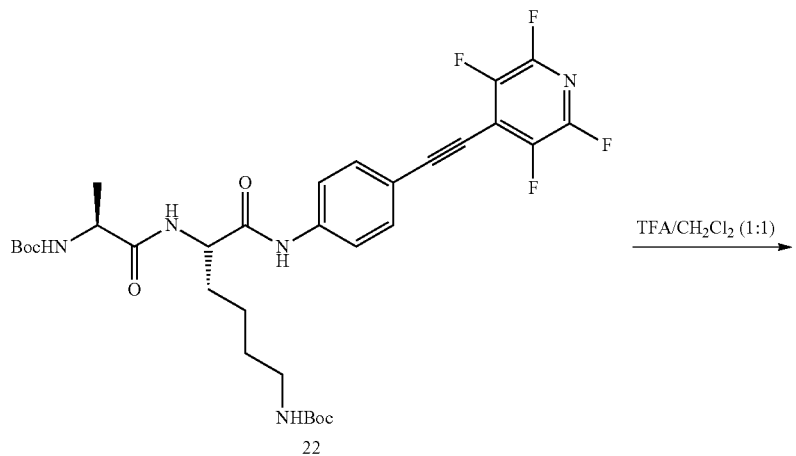

(5-(2-tert-Butoxycarbonylamino-propionylamino)-5-[4-(2,3,5,6-tetrafluoro-pyridin-4-ylethynyl)-phenyl-carbamoyl]-pentyl}-carbamic acid tert-butyl ester (22):

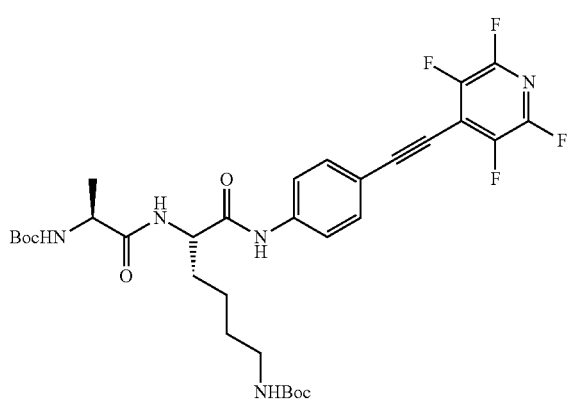

To a solution of acid Boc-Ala-Lys-OH, (21) (207 mg, 0.5 mmol) in CH$_2$Cl$_2$ (5 mL) at 0° C., was sequentially treated with HOBt (101 mg, 0.75 mmol) and DCC (154 mg, 0.75 mmol). After 15 min., 4-((perfluoropyridin-4-yl)ethynyl) aniline (7) (154 mg, 0.08 mmol) was added to the reaction mixture. After stirring for 1 days at room temperature, the reaction mixture was diluted with ethylacetate, washed with saturated NH$_4$Cl solution, saturated NaHCO$_3$, 1 N HCl, water, brine, dried (Na$_2$SO$_4$), filtered and concentrated in vacuo. Chromatographic purification (SiO$_2$, 50% ethylacetate in hexane) of the residue provided (22) (170 mg, 52%) as a white solid; $^1$H NMR (400 MHz, CD$_3$OD): $^1$H NMR (400 MHz, CDCl$_3$): δ 9.17 (bs, 1H), 7.72 (d, J=8.5 Hz, 2H), 7.53 (d, J=8.5 Hz, 2H), 6.91 (bs, 1H), 5.22 (bs, 1H), 4.75 (bs, 1H), 4.57 (bs, 1H), 4.21-4.12 (m, 1H), 3.17-3.05 (m, 2H), 1.81-1.62 (m, 2H), 1.61-1.31 (m, 25H); MS (ESI): m/z (%) 688 (100) [M+Na]$^+$;

(S)-6-amino-2-((S)-2-aminopropanamido)-N-(4-((perfluoropyridin-4-yl)ethynyl)phenyl) hexanamide (23):

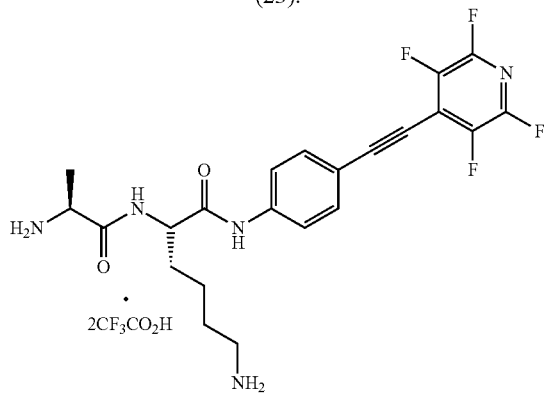

Boc-protected compound (22) (100 mg, 0.15 mmol) was dissolved in $CH_2Cl_2$ (1 mL) and cooled to 0° C. followed by addition of trifluoroacetic acid (1 mL). Reaction mixture was stirred for 12 h and was poured in a centrifuge tube containing anhydrous diethyl ether (15 mL). Immediately solid came out and it was centrifuged. The solid material was washed with anhydrous diethyl ether (2×15 mL) to get pure TFA-salt of (23) (90 mg, 86%) as white solid; $^1$H NMR (400 MHz, $CD_3OD$): 7.74 (d, J=8.4 Hz, 2H), 7.61 (d, J=8.4 Hz, 2H), 4.51 (dd, J=8.3, 5.3 Hz, 1H), 4.01 (q, J=6.8 Hz, 1H), 2.94 (t, J=7.7 Hz, 2H), 1.99-1.88 (m, 1H), 1.87-1.78 (m, 1H), 1.76-1.66 (m, 2H), 1.62-1.44 (m, 2H), 1.54 (d, J=6.8 Hz, 3H);

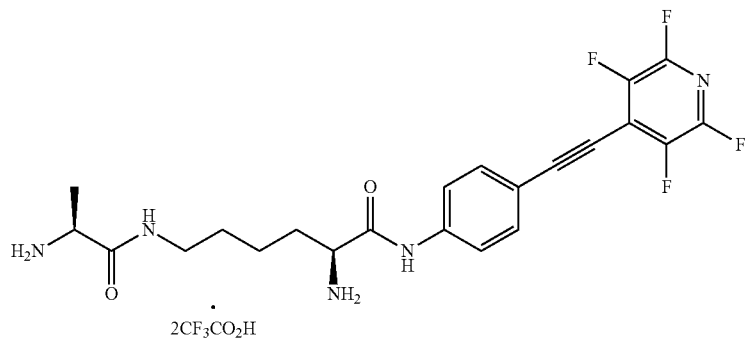

26

{5-(2-tert-Butoxycarbonylamino-propionylamino)-1-
[4-(2,3,5,6-tetrafluoro-pyridin-4-ylethynyl)-phenyl-
carbamoyl]-pentyl}-carbamic acid tert-butyl ester
(25):

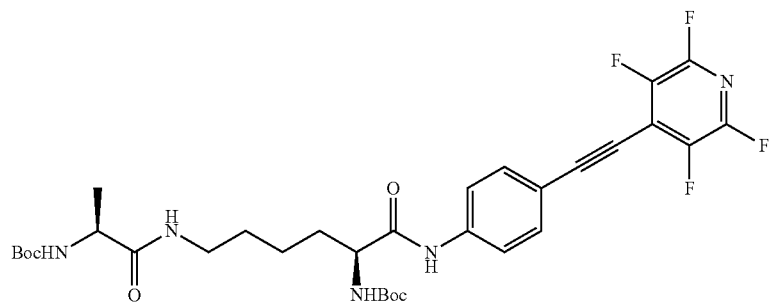 [SMILES: C[C@H](NC(=O)OC(C)(C)C)C(=O)NCCCC[C@H](NC(=O)OC(C)(C)C)C(=O)Nc1ccc(C#Cc2c(F)c(F)nc(F)c2F)cc1]

The compound (25) was prepared from compound (24) by using the same procedure as synthesis of compound (22) from compound (21), in 55% yield; $^1$H NMR (400 MHz, CD$_3$OD): $^1$H NMR (400 MHz, CDCl$_3$): δ 9.31 (bs, 1H), 7.66 (d, J=8.0 Hz, 2H), 7.54 (d, J=8.0 Hz, 2H), 6.73 (bs, 1H), 6.59 (bs, 1H), 5.25 (bs, 1H), 4.25-4.15 (m, 1H), 3.37-3.08 (m, 2H), 1.75-1.48 (m, 4H), 1.46-1.22 (m, 23H); MS (ESI): m/z (%) 688 (100) [M+Na]$^+$;

(S)-2-amino-6-((S)-2-aminopropanamido)-N-(4-
((perfluoropyridin-4-yl)ethynyl)phenyl) hexanamide
(26):

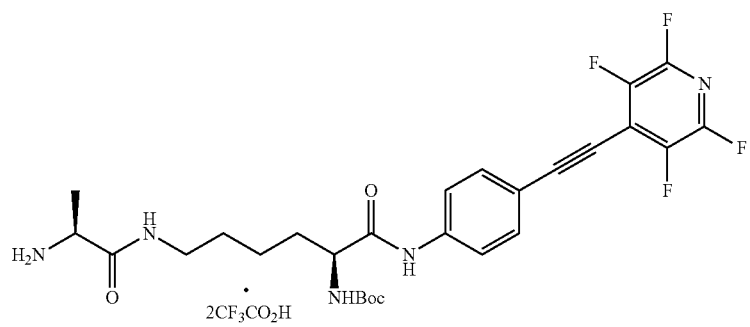 [SMILES: C[C@H](N)C(=O)NCCCC[C@H](NC(=O)OC(C)(C)C)C(=O)Nc1ccc(C#Cc2c(F)c(F)nc(F)c2F)cc1]

The compound (26) was prepared from compound (25) by using the same procedure as synthesis of compound (23) from compound (22), in 95% yield; $^1$H NMR (400 MHz, CD$_3$OD): 7.77 (d, J=8.7 Hz, 2H), 7.64 (d, J=8.7 Hz, 2H), 4.0 (t, J=6.6 Hz, 1H), 3.84 (q, J=7.3 Hz, 1H), 3.29-3.19 (m, 2H), 2.05-1.85 (m, 2H), 1.65-1.55 (m, 2H), 1.54-1.46 (m, 2H), 1.43 (d, J=7.3 Hz, 3H);

Synthesis of β-amino Alanine conjugates:

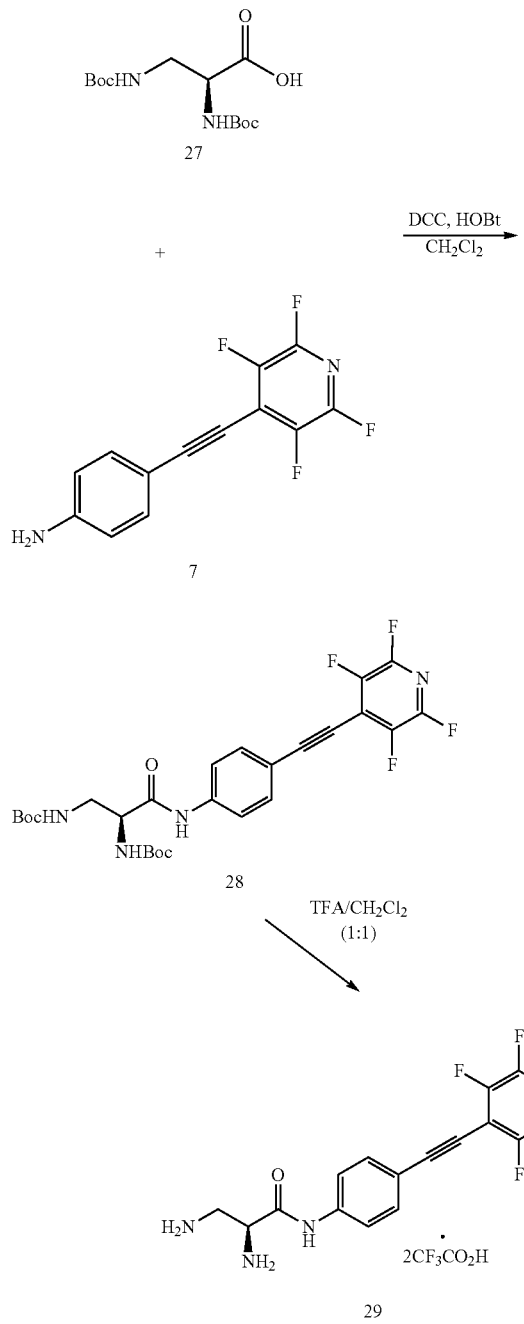

(S)-di-tert-butyl (3-oxo-3-((4-((perfluoropyridin-4-yl)ethynyl)phenyl)amino)propane-1,2-diyl)dicarbamate (28):

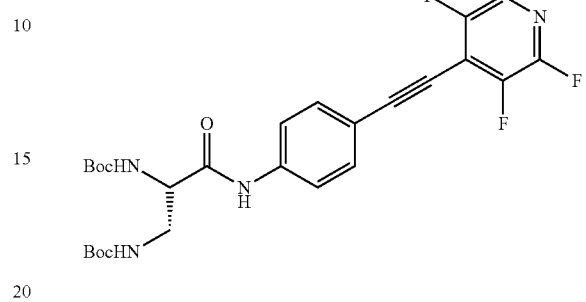

The compound (28) was prepared from compound (27) by using the same procedure as synthesis of compound (22) from compound (21), in 60% yield; $^1$H NMR (400 MHz, CD$_3$OD): $^1$H NMR (400 MHz, CDCl$_3$): δ 9.40 (bs, 1H), 7.63 (d, J=8.6 Hz, 2H), 7.58 (d, J=8.6 Hz, 2H), 5.97 (bs, 1H), 5.27 (bs, 1H), 4.34-4.28 (m, 1H), 3.69-3.60 (m, 1H), 3.58-3.50 (m, 1H), 1.48 (3, 9H), 1.45 (s, 9H);

(S)-2,3-diamino-N-(4-((perfluoropyridin-4-yl)ethynyl)phenyl)propanamide (29):

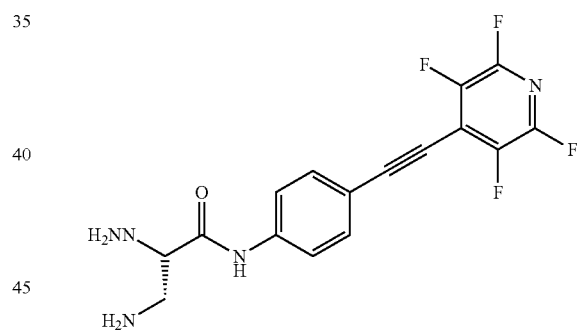

The compound (29) was prepared from compound (28) by using the same procedure as synthesis of compound (23) from compound (21), in 85% yield; $^1$H NMR (400 MHz, CD$_3$OD): 7.81 (d, J=8.5 Hz, 2H), 7.64 (d, J=8.5 Hz, 2H), 4.11 (t, J=5.8 Hz, 1H), 3.47-3.42 (m, 2H).

Scheme 7.
Synthesis of tetrafluoropyridinyl (TFP) and phenyl (Ph) substituted bis acetylene lysine conjugates.

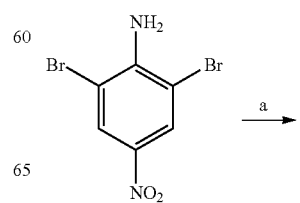

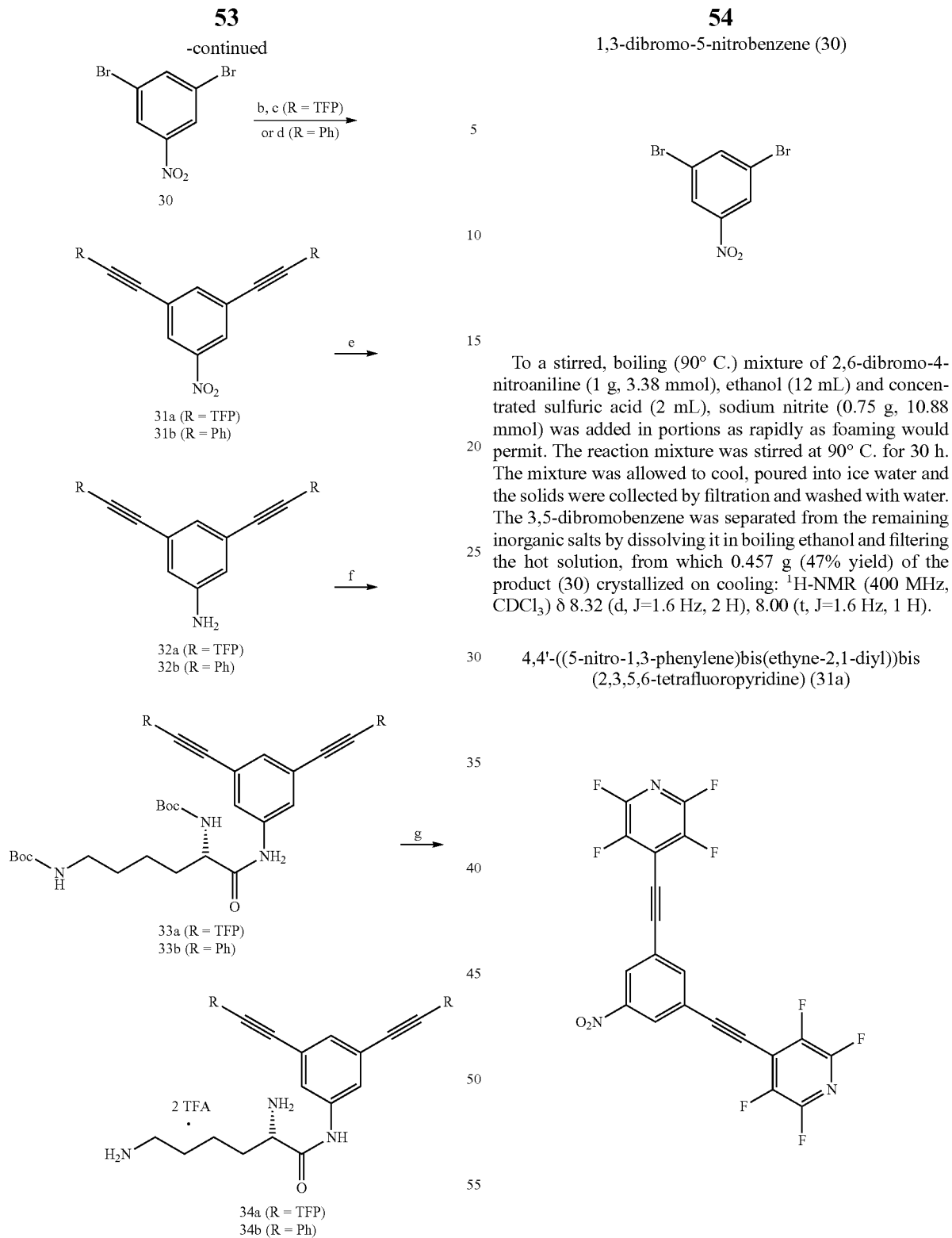

Reagents and conditions:
a) NaNO₂, H₂SO₄, EtOH
b) Pd(PPh₃)₂Cl₂, CuI, TMSCCH, Et₃N
c) CsF, pentafluoropyridine, DMF
d) Pd(PPh₃)₂Cl₂, CuI, Phenylacetylene, Et₃N
e) SnCl₂, HCl, THF
f) L—Boc-Lys(Boc)—OH, POCl₃, Pyridine
or L—Boc-Lys(Boc)—OH, HOBT, EDC, CH₂Cl₂,
g) Trifluoro acetic acid (TFA)

1,3-dibromo-5-nitrobenzene (30)

To a stirred, boiling (90° C.) mixture of 2,6-dibromo-4-nitroaniline (1 g, 3.38 mmol), ethanol (12 mL) and concentrated sulfuric acid (2 mL), sodium nitrite (0.75 g, 10.88 mmol) was added in portions as rapidly as foaming would permit. The reaction mixture was stirred at 90° C. for 30 h. The mixture was allowed to cool, poured into ice water and the solids were collected by filtration and washed with water. The 3,5-dibromobenzene was separated from the remaining inorganic salts by dissolving it in boiling ethanol and filtering the hot solution, from which 0.457 g (47% yield) of the product (30) crystallized on cooling: ¹H-NMR (400 MHz, CDCl₃) δ 8.32 (d, J=1.6 Hz, 2 H), 8.00 (t, J=1.6 Hz, 1 H).

4,4'-((5-nitro-1,3-phenylene)bis(ethyne-2,1-diyl))bis(2,3,5,6-tetrafluoropyridine) (31a)

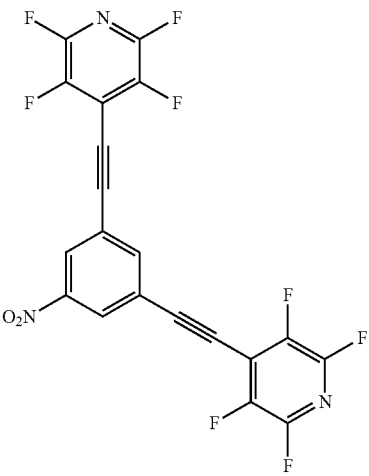 [SMILES: O=[N+]([O-])c1cc(C#Cc2c(F)c(F)nc(F)c2F)cc(C#Cc2c(F)c(F)nc(F)c2F)c1]

Pentafluoropyridine (1.63 g, 9.66 mmol) was added to the mixture of 1,3-bis(3,3-dimethyl-lyn-lyl)-5-nitrobenzene (1.01 g, 3.22 mmol) and CsF (1.46 g, 9.66 mmol) in DMF (10 mL) slowly. The reaction mixture was stirred overnight. Brine (30 mL) and EtOAc (50 mL) were added. Organic phase was separated and washed with water. Solvent was evaporated by rotary evaporation and the residue was chromatographed (EtOAc:Hexane=1:10) to provide the desired product in 35% yield: ¹H-NMR (400 MHz, CDCl₃) δ 8.53 (d, J=1.3 Hz, 2H), 8.16 (t, J=1.3 Hz, 1H).

3,5-bis((perfluoropyridin-4-yl)ethynyl)aniline (32a)

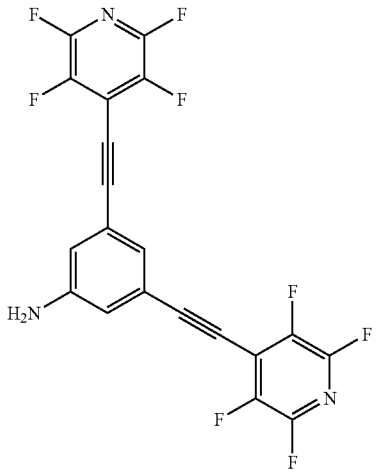

SnCl$_2$ (0.20 g, 1.06 mmol) was added slowly (1 h) to the solution of 4,4'-((5-nitro-1,3-phenylene)bis(ethylene-2,1-diyl))bis(2,3,5,6-tetrafluoropyridine (0.10 g, 0.21 mmol) and HCl (1 mL) in THF (10 mL). The reaction mixture was stirred for 3 hours. The reaction mixture was basified till pH>9 with NaOH (1.0 N solution), the product was extracted with EtOAc and dried over (Na$_2$SO$_4$). Solvent was evaporated to afford 0.09 g (95%) of the product: $^1$H-NMR (400 MHz, CDCl$_3$) δ 7.27 (t, J=1.3 Hz, 1H), 6.99 (d, J=1.3 Hz, 2H).

(S)-di-tert-butyl (6-((3,5-bis((perfluoropyridin-4-yl)ethynyl)phenyl)amino)-6-oxohexane-1,5-diyl)dicarbamate (33a)

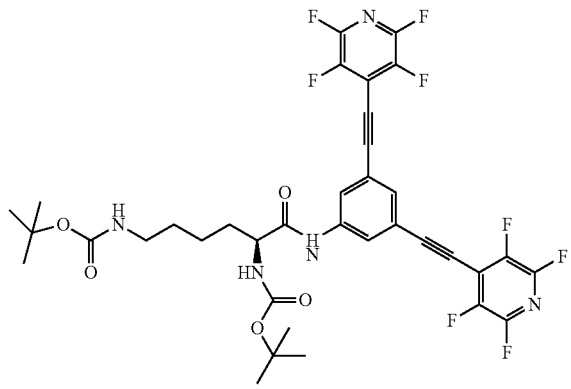 [SMILES: CC(C)(C)OC(=O)NCCCC[C@H](NC(=O)OC(C)(C)C)C(=O)Nc1cc(C#Cc2c(F)c(F)nc(F)c2F)cc(C#Cc2c(F)c(F)nc(F)c2F)c1]

L-Boc-Lys(Boc)-OH (0.16 g, 0.45 mmol) was dissolved in 1 mL of pyridine. The solution was cooled to −25° C. and phosphorus oxychloride (0.07 g, 0.45 mmol) was added dropwise with vigorous stirring. After stirring for 15 min. at −25° C., 3,5-bis((perfluoropyridin-4-yl)ethynyl)aniline (0.07 g, 0.23 mmol) in pyridine (1 mL) was added slowly. The reaction mixture was stirred for 0.5 h at −25° C. and then at room temperature for 12 h. The reaction mixture was quenched with ice/water and extracted with EtOAc. The organic layer was washed with sat. NaHSO$_4$ three times, dried with Na$_2$SO$_4$ and was concentrated in vacuo. The crude product was subjected to chromatography with (EtOAc:Hexane=1:5) and the product was obtained in 22% yield: $^1$H-NMR (400 MHz, CDCl$_3$) δ 9.33 (s, 1H), 7.86 (s, 2H), 7.49 (s, 1H), 5.38 (d, J=7.1 Hz, 1H), 4.68 (s, 1H), 4.27 (d, J=5.0 Hz, 1H), 3.07-3.18 (m, 2H), 1.76 (s, 2H), 1.53 (s, 2H), 1.49 (s, 9H), 1.45 (s, 11H).

(S)-2,6-diamino-N-(3,5-bis((perfluoropyridin-4-yl)ethynyl)phenyl)hexanamide (34a)

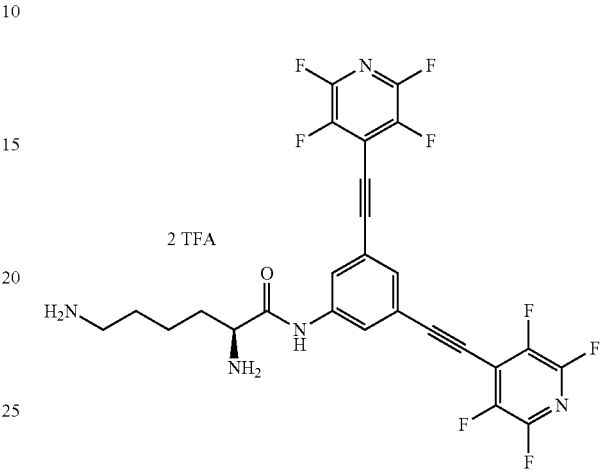

(S)-di-tert-butyl (6-((3,5-bis((perfluoropyridin-4-yl)ethynyl)phenyl)amino)-6-oxohexane-1,5-diyl)dicarbamate (0.02 g, 0.04 mmol) was reacted with neat trifluoroacetic acid (TFA) (2 mL) and the solution was stirred for 4 hours at room temperature. TFA was evaporated and the product (25 mg, 96%) was purified by recrystallization with ethanol: $^1$H-NMR (400 MHz, CD$_3$OD) δ 8.08 (d, J=1.3 Hz, 2H), 7.66 (t, J=1.3 Hz, 1H), 4.10 (t, J=6.5 Hz, 1H), 2.96 (t, J=15.3 Hz, 2H), 1.94-2.10 (m, 2H), 1.73 (m, 2H), 1.57 (m, 2H), 1.30 (m, 2H).

((5-nitro-1,3-phenylene)bis(ethyne-2,1-diyl))dibenzene (31b)

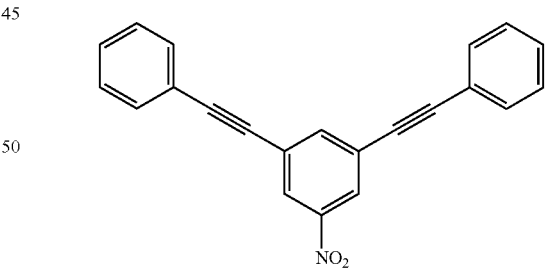

A mixture of 1,3-dibromo-5-nitrobenzene (0.56 g, 2.00 mmol), bis(triphenylphosphine)palladium(II) chloride (0.10 g, 0.14 mmol) and copper(I) iodide (0.027 g, 0.14 mmol) in Et$_3$N was degassed (three times). Phenylacetylene (0.50 g, 4.88 mmol) was added and mixture was stirred overnight. The reaction mixture was filtered through a celite pad and the pad was rinsed with CH$_2$Cl$_2$. The filtrate was washed with brine and the organic layer was dried with (Na$_2$SO$_4$), filtered, and concentrated. The residue was purified by column chromatography (Dichloromethane;Hexane=1:10) to afford ((5-nitro-1,3-phenylene)bis(ethyne-2,1-diyl))dibenzene (0.33 g, 51% yield): $^1$H-NMR (400 MHz, CDCl$_3$) δ 8.30 (d, J=1.3 Hz, 2H), 7.96 (t, J=1.3 Hz, 1H), 7.56 (m, 4H), 7.40 (m, 6H).

3,5-bis(phenylethynyl)aniline (32b)

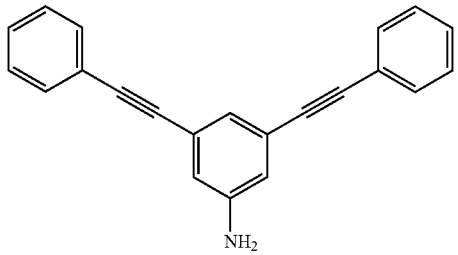 [SMILES: Nc1cc(C#Cc2ccccc2)cc(C#Cc2ccccc2)c1]

A solution of SnCl$_2$ (0.96 g, 5.10 mmol) was added slowly (1 h) to the mixture of ((5-nitro-1,3-phenylene)bis(ethyne-2,1-diyl))dibenzene (0.33 g, 1.02 mmol) and HCl (1 mL) in THF (10 mL). The reaction mixture was stirred at room temperature for 3 hours. After neutralization with NaOH (1.0 N solution), the product was extracted with EtOAc and dried over (Na$_2$SO$_4$). Solvent was evaporated to afford 0.26 g (86%) of the product: $^1$H-NMR (400 MHz, CDCl$_3$) δ 7.51 (m, 4H), 7.34 (m, 6H), 7.14 (t, J=1.3 Hz, 1H), 6.82 (d, J=1.3 Hz, 2H).

(S)-di-tert-butyl (6-((3,5-bis(phenylethynyl)phenyl) amino)-6-oxohexane-1,5-diyl) dicarbamate (33b)

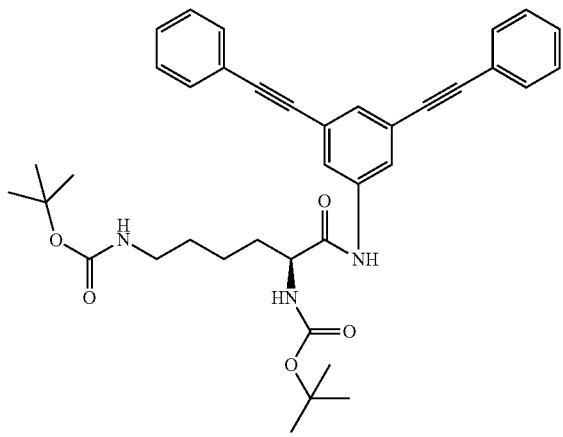 [SMILES: CC(C)(C)OC(=O)NCCCC[C@H](NC(=O)OC(C)(C)C)C(=O)Nc1cc(C#Cc2ccccc2)cc(C#Cc2ccccc2)c1]

HOBt (0.25 g, 1.61 mmol) was added to the solution of L-Boc-Lys(Boc)-OH (0.56 g, 1.61 mmol) and EDC (0.25 g, 1.61 mmol) in dichloromethane at 0° C., then 3,5-bis(phenylethynyl)aniline (0.24 g 0.80 mmol) was added at 0° C. The reaction mixture was stirred for 30 min at 0° C. and then at room temperature for 18 h. The reaction mixture was quenched with water and extracted with EtOAc and washed with saturated NaHSO$_4$, then dried with Na$_2$SO$_4$. The solvent was evaporated in vacuo. The crude product was subjected to chromatography with (EtOAc:Hexane=2:5). Desired product was obtained (0.35 g, 70%): $^1$H-NMR (400 MHz, CDCl$_3$) δ 8.58 (s, 1H), 7.73 (s, 2H), 7.51 (m, 4H), 7.44 (s, 1H), 7.35 (m, 6H), 5.19 (s, 1H), 4.66 (s, 1H), 4.19 (s, 1H), 3.06-3.22 (m, 2H), 1.99 (m, 2H), 1.55 (m, 2H), 1.49 (s, 10H), 1.45 (s, 10H).

(S)-2,6-diamino-N-(3,5-bis(phenylethynyl)phenyl) hexanamide (34b)

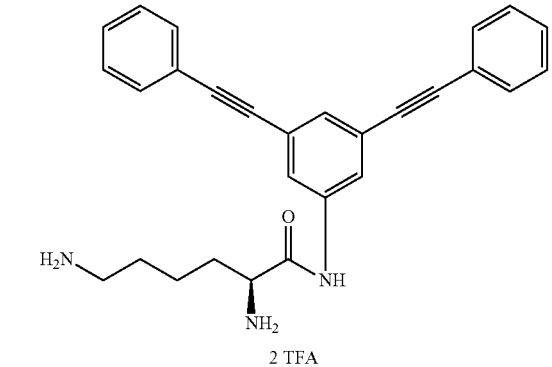 [SMILES: NCCCC[C@H](N)C(=O)Nc1cc(C#Cc2ccccc2)cc(C#Cc2ccccc2)c1]

(S)-di-tert-butyl (6-((3,5-bis(phenylethynyl) phenyl) amino)-6-oxohexane-1,5-diyl)dicarbamate (0.35 g, 0.56 mmol) was reacted with neat TFA (10 mL) and the solution was stirred for 5 hours at room temperature. TFA was evaporated and the product (0.34 mg, 93%) was purified by recrystallization with ethanol: $^1$H-NMR (400 MHz, CD$_3$OD) δ 7.80 (d, J=1.4 Hz, 2H), 7.52-7.55 (m, 4H), 7.45 (t, J=1.4 Hz, 1H), 7.38-7.41 (m, 6H), 4.06 (t, J=6.5 Hz, 1H), 2.96 (t, J=15.4 Hz, 2H), 1.96-2.06 (m, 2H), 1.70-1.78 (m, 2H), 1.50-1.60 (m, 2H).

Plasmid Relaxation Assays

Figure 10A:
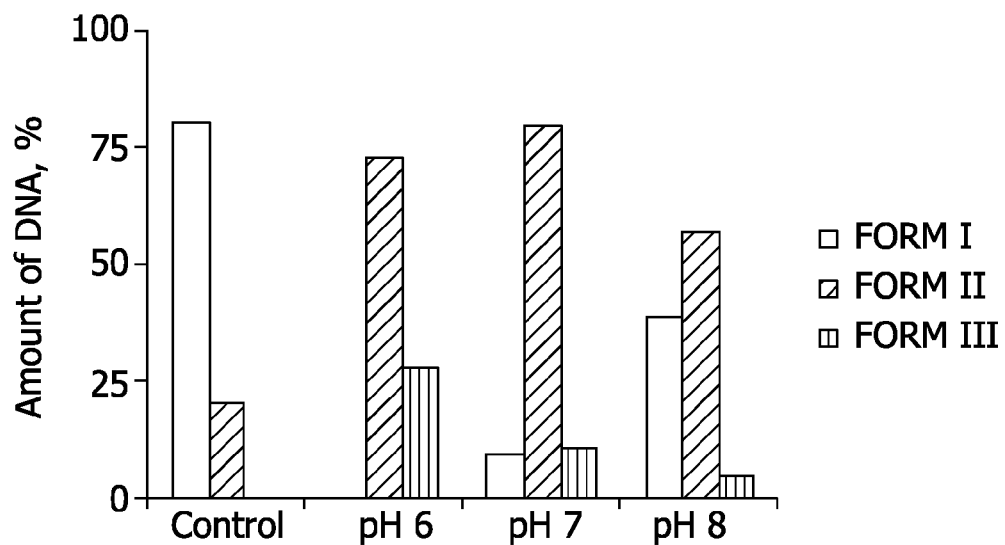
FIGS. 10A and 10B depict quantified plasmid relaxation assays with 30 μM/b.p. pBR322 plasmid DNA for (15) (15 μM, FIG. 10A) and (18) (15 μM, FIG. 10B) after 10 min of UV irradiation. Reported values represent the average of four experiments. White Bar: Form I DNA, Partially Shaded Bar: Form II DNA, black BAR: Form III DNA.
Figure 10B:
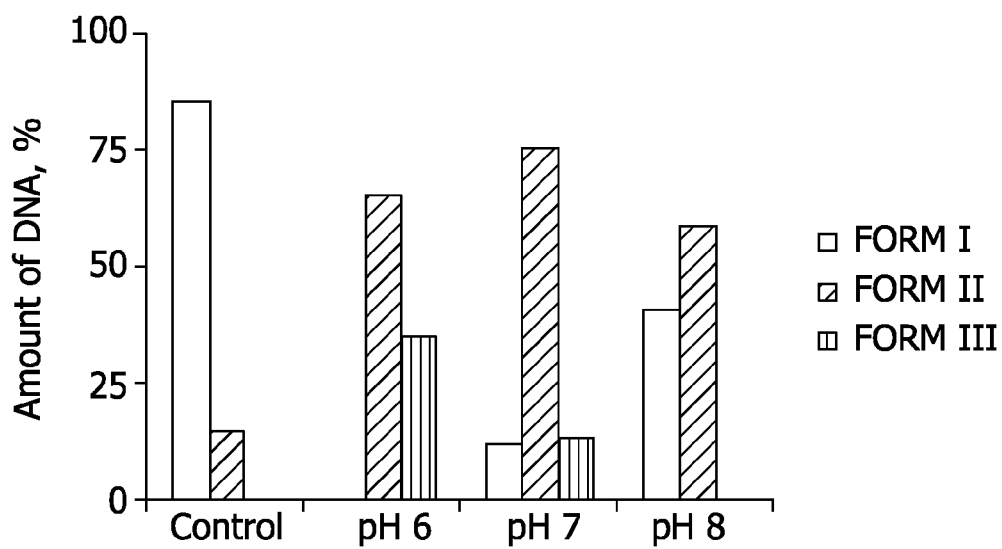

Plasmid relaxation assays were performed on pBR322 plasmid DNA using (S)-2,5-Diamino-N-(4-((perfluoropyridin-4-yl)ethynyl)phenyl)pentanamide Dihydrochloride (15) and (S)-2,5-Diamino-N-(3,4-bis((perfluoropyridin-4-yl)phenyl)pentanamide Dihydrochloride (18). The concentration of each was 15 mM. FIG. 10 depicts the percent DNA in each of Forms I, II, and III after 10 minutes UV irradiation. In this and each of the below relaxation experiments, the reported values represent the average of four experiments. In each of FIGS. 10 through 15: white bar: Form I DNA; partially shaded bar: Form II DNA; black bar: Form III DNA.

Figure 11:
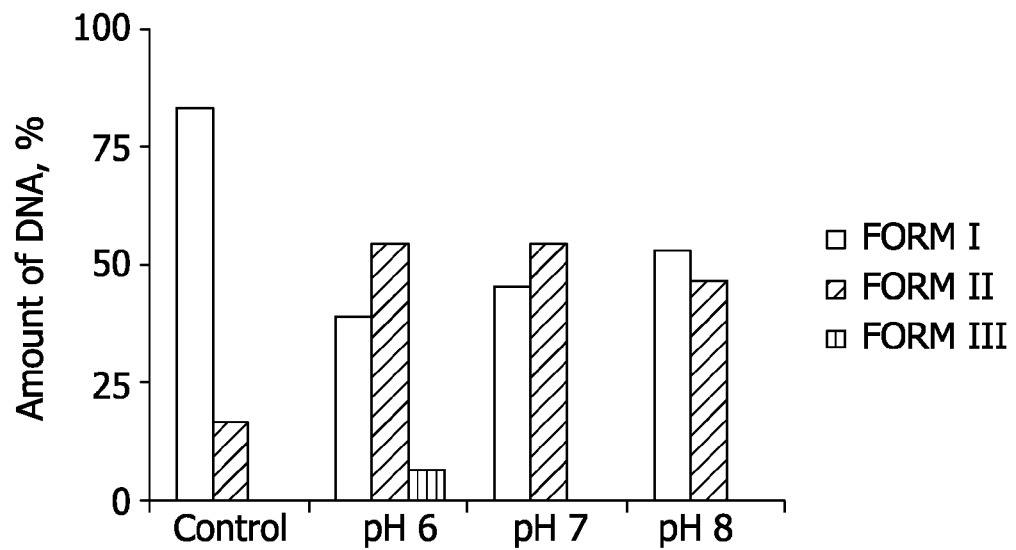
FIG. 11 depicts quantified plasmid relaxation assays with 30 μM/b.p. pBR322 plasmid DNA for (20) (15 μM). Reported values represent the average of four experiments. White Bar: Form I DNA, Partially Shaded Bar: Form II DNA, black BAR: Form III DNA.

Plasmid relaxation assays were performed on pBR322 plasmid DNA using 2,6-Diamino-N-(2,3-bis((perfluoropyridin-4-yl)ethynyl)phenyl)hexanamide Dihydrochloride (20). The concentration of the cleavage compound was 15 mM. FIG. 11 depicts the percent DNA in each of Forms I, II, and III after 10 minutes UV irradiation.

Figure 12:
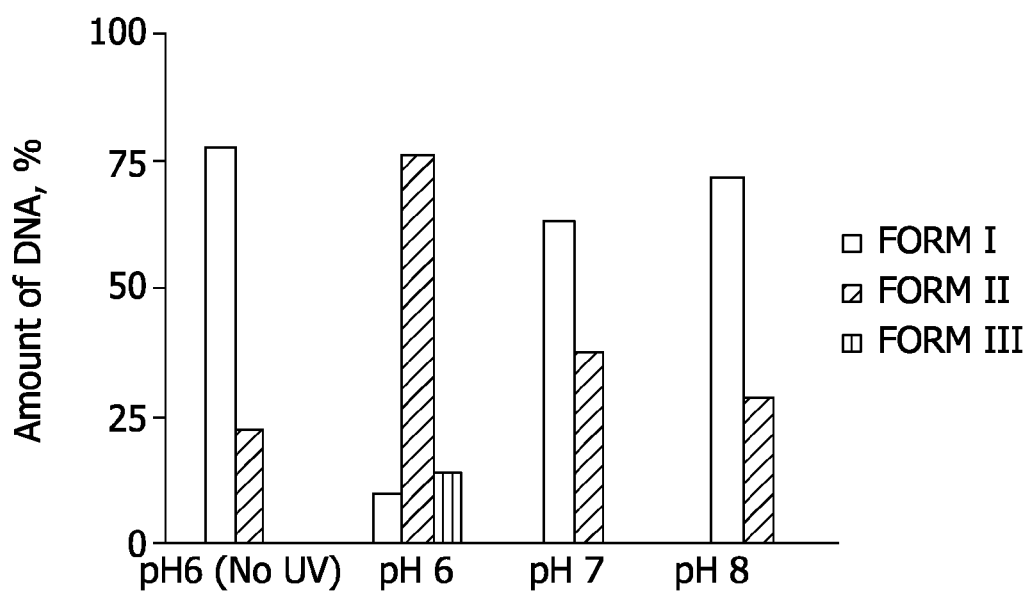
FIG. 12 depicts quantified plasmid relaxation assays with 30 μM/b.p. pBR322 plasmid DNA for (23) (15 μM). Reported values represent the average of four experiments. White Bar: Form I DNA, Partially Shaded Bar: Form II DNA, black BAR: Form III DNA.

Plasmid relaxation assays were performed on pBR322 plasmid DNA using (S)-6-amino-2-((S)-2-aminopropanamido)-N-(4-((perfluoropyridin-4-yl)ethynyl)phenyl) hexanamide (23). The concentration of the cleavage compound was 15 mM. FIG. 12 depicts the percent DNA in each of Forms I, II, and III after 10 minutes UV irradiation.

Figure 13:
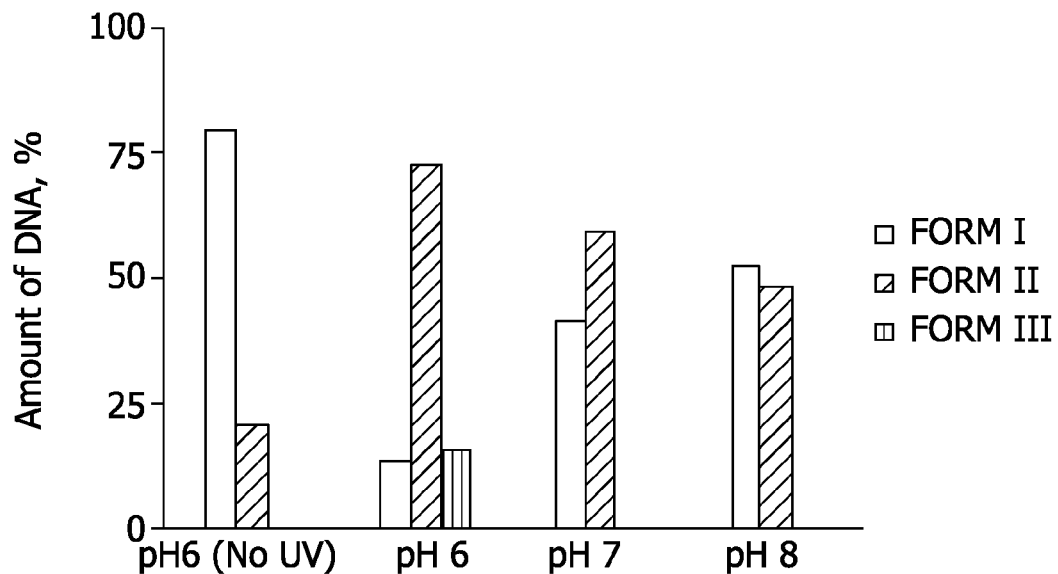
FIG. 13 depicts quantified plasmid relaxation assays with 30 μM/b.p. pBR322 plasmid DNA for (26) (15 μM). Reported values represent the average of four experiments. White Bar: Form I DNA, Partially Shaded Bar: Form II DNA, black BAR: Form III DNA.

Plasmid relaxation assays were performed on pBR322 plasmid DNA using (S)-2-amino-6-((S)-2-aminopropanamido)-N-(4-((perfluoropyridin-4-yl)ethynyl)phenyl) hexanamide (26). The concentration of the cleavage compound was 15 mM. FIG. 13 depicts the percent DNA in each of Forms I, II, and III after 10 minutes UV irradiation.

Figure 14:
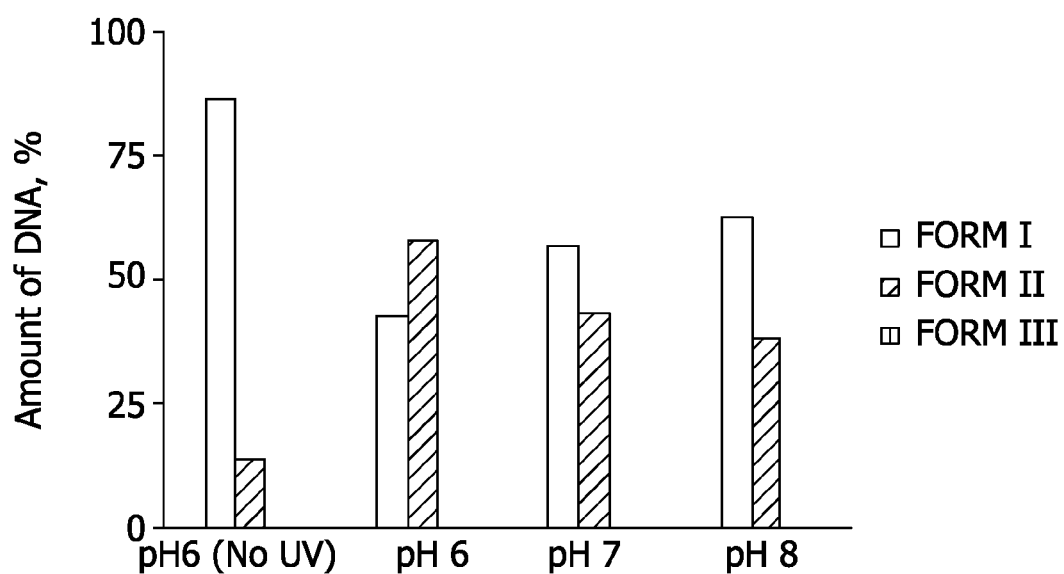
FIG. 14 depicts quantified plasmid relaxation assays with 30 μM/b.p. pBR322 plasmid DNA for (29) (15 μM). Reported values represent the average of four experiments. White Bar: Form I DNA, Partially Shaded Bar: Form II DNA, black BAR: Form III DNA.

Plasmid relaxation assays were performed on pBR322 plasmid DNA using (S)-2,3-diamino-N-(4-((perfluoropyridin-4-yl)ethynyl)phenyl)propanamide (29). The concentration of the cleavage compound was 15 mM. FIG. 14 depicts the percent DNA in each of Forms I, II, and III after 10 minutes UV irradiation.

Figure 15A:
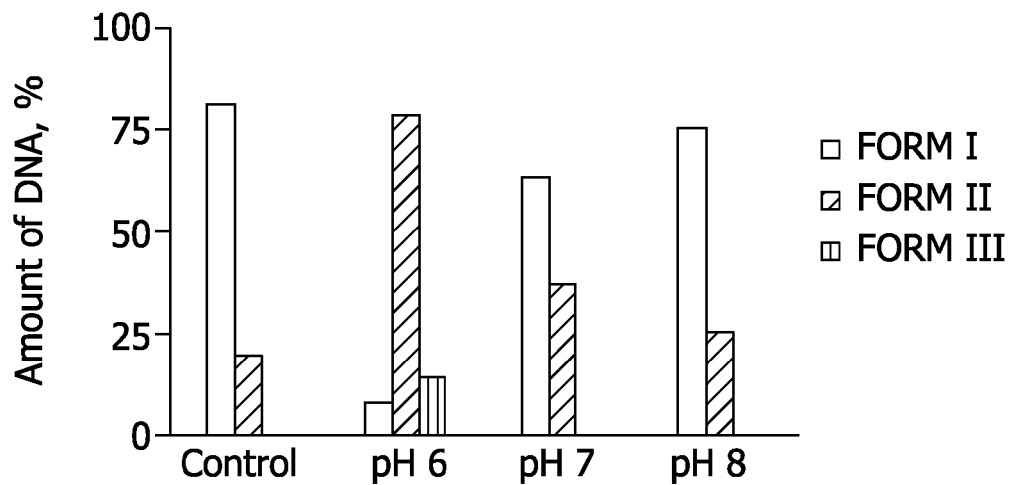
FIGS. 15A and 15B depict quantified plasmid relaxation assays with 30 μM/b.p. pBR322 plasmid DNA for (34a) (15 μM, FIG. 15A) and (34b) (15 μM, FIG. 15B) after 10 min of UV irradiation. Reported values represent the average of four experiments. White Bar: Form I DNA, Partially Shaded Bar: Form II DNA, black BAR: Form III DNA.
Figure 15B:
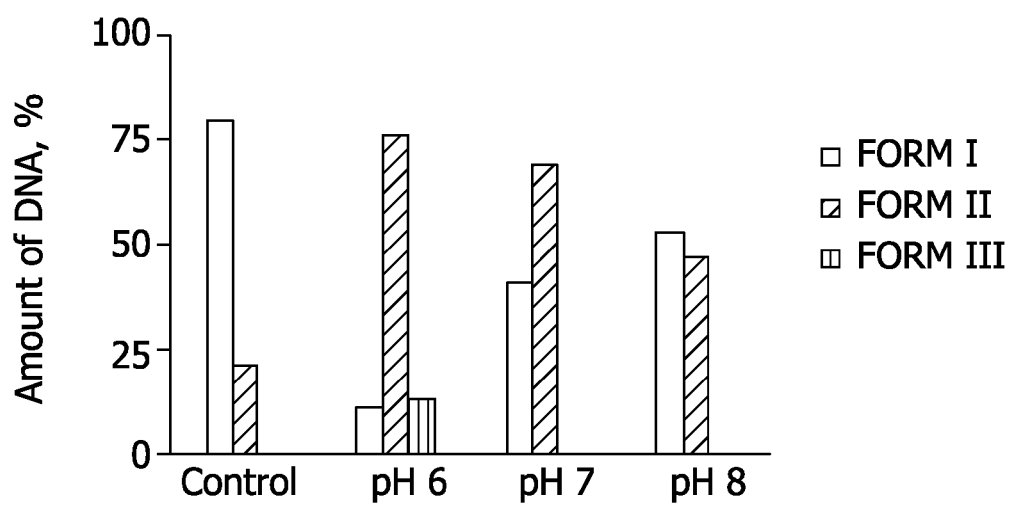

Plasmid relaxation assays were performed on pBR322 plasmid DNA using (S)-2,6-diamino-N-(3,5-bis((perfluoropyridin-4-yl)ethynyl)phenyl)hexanamide (34a) and (S)-2,6-diamino-N-(3,5-bis(phenylethynyl) phenyl)hexanamide (34b). The concentration of the cleavage compound was 15 mM. FIG. 15A and 15B depict the percent DNA in each of Forms I, II, and III after 10 minutes UV irradiation.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A compound having the structure:

Structure (Xa)

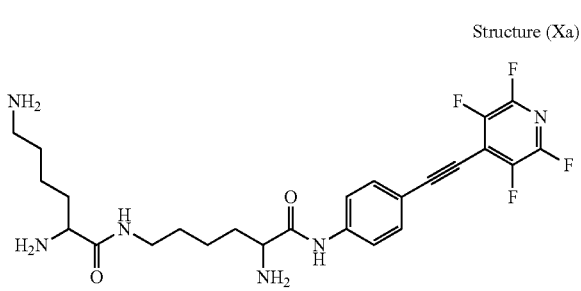 [SMILES: NCCCCC(N)C(=O)NCCCCC(N)C(=O)Nc1ccc(C#Cc2c(F)c(F)nc(F)c2F)cc1]

or a HCl salt of the compound or a trifluoroacetic acid salt of the compound.

2. A method of forming a double strand cleavage in DNA, the method comprising:

contacting the compound of claim 1 with double stranded DNA to thereby bind the compound of claim 1 with the double stranded DNA.

3. The method of claim 2 further comprising irradiating the double stranded DNA having the compound bound thereto.

4. The method of claim 2 wherein the contact occurs in a cellular environment having a pH sufficient to protonate one or more amino groups the compound.

5. A compound having the structure:

Structure (XIa)

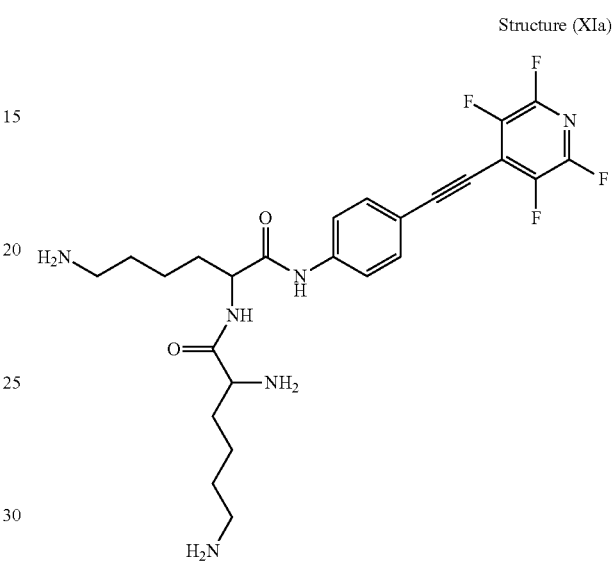

or a HCl salt of the compound or a trifluoroacetic acid salt of the compound.

6. A method of forming a double strand cleavage in DNA, the method comprising:

contacting the compound of claim 5 with double stranded DNA to thereby bind the compound of claim 5 with the double stranded DNA.

7. The method of claim 6 further comprising irradiating the double stranded DNA having the compound bound thereto.

8. The method of claim 6 wherein the contact occurs in a cellular environment having a pH sufficient to protonate one or more amino groups in the compound.

* * * * *